United States Patent
Singh

(10) Patent No.: US 9,682,093 B2
(45) Date of Patent: Jun. 20, 2017

(54) COMPOSITIONS AND METHODS FOR TREATING OR PREVENTING METABOLIC SYNDROME DISORDERS

(71) Applicant: CHARLES R. DREW UNIVERSITY OF MEDICINE AND SCIENCE, Los Angeles, CA (US)

(72) Inventor: Rajan Singh, Los Angeles, CA (US)

(73) Assignee: Charles R. Drew University of Medicine and Science, Los Angeles, CA (US)

( * ) Notice: Subject to any disclaimer, the term of this patent is extended or adjusted under 35 U.S.C. 154(b) by 0 days.

(21) Appl. No.: 14/389,374

(22) PCT Filed: Apr. 1, 2013

(86) PCT No.: PCT/US2013/034855
§ 371 (c)(1),
(2) Date: Sep. 29, 2014

(87) PCT Pub. No.: WO2013/149258
PCT Pub. Date: Oct. 3, 2013

(65) Prior Publication Data
US 2016/0120890 A1    May 5, 2016

Related U.S. Application Data

(60) Provisional application No. 61/618,603, filed on Mar. 30, 2012.

(51) Int. Cl.
| | | |
|---|---|---|
| A61K 31/7034 | (2006.01) | |
| A61K 45/06 | (2006.01) | |
| A61K 31/417 | (2006.01) | |
| A61K 31/05 | (2006.01) | |
| A61K 31/352 | (2006.01) | |
| A61K 31/095 | (2006.01) | |
| A61K 31/12 | (2006.01) | |

(52) U.S. Cl.
CPC .......... *A61K 31/7034* (2013.01); *A61K 31/05* (2013.01); *A61K 31/095* (2013.01); *A61K 31/12* (2013.01); *A61K 31/352* (2013.01); *A61K 31/417* (2013.01); *A61K 45/06* (2013.01)

(58) Field of Classification Search
CPC .. A61K 31/7034; A61K 31/05; A61K 31/352; A61K 31/417; A61K 45/06
USPC ................... 514/385, 456, 35, 733
See application file for complete search history.

(56) References Cited

FOREIGN PATENT DOCUMENTS

| WO | 2006013602 A1 | 2/2006 |
|---|---|---|
| WO | 2013001270 A1 | 1/2013 |

OTHER PUBLICATIONS

Schneider et al. Resveratrol Inhibits Intestinal Tumorigenesis and Modulates Host-Defense-Related Gene Expression in an Animal Model of Human Familial Adenomatous Polyposis. Nutrition and Cancer, 39(1), 102-107, 2001.*
Glossary of medical education terms, Institute of International Medical Education. http://www.iime.org/glossary.htm Accessed in Mar. 2013.*
Grundy et al. Diagnosis and Management of the Metabolic Syndrome an American Heart Association/National Heart, Lung, and Blood Institute Scientific Statement. Circulation 112:2735-2752, 2005.*
Nakatani et al. Follistatin-derived peptide expression in muscle decreases adipose tissue mass and prevents hepatic steatosis. Am J Physiol Endocrinol Metab 300: E543-E553, 2011. First published Jan. 4, 2011.*
Iezzi et al. Deacetylase Inhibitors Increase Muscle Cell Size by Promoting Myoblast Recruitment and Fusion through Induction of Follistatin. Developmental Cell, vol. 6, 673-684, May 2004.*
Pfützner et al. Pioglitazone: an antidiabetic drug with cardiovascular therapeutic effects. Expert Rev. Cardiovasc. Ther. 4(4), 445-459 (2006).*
Guo et al. Overexpression of Mouse Follistatin Causes Reproductive Defects in Transgenic Mice. Molecular Endocrinology 12: 96-106, 1998.*
Szkudelska, K., et al., Resveratrol, Obesity and Diabetes, Eur. J. Pharmacol., 2010, 635:1-8.
Jeong, G-S, et al., Butein from Rhus verniciflua Protects Pancreatic Beta Cells Against Cytokine-Induced Toxicity Mediated by Inhibition of Nitric Oxide Formation, Biol. Pharm. Bull., 2011, 34(1):97-102.
Hwank, J-T, et al., Genistein, EGCG, and Capsaicin Inhibit Adipocyte Differentiation Process Via Activating AMP-Activated Protein Kinase, Biochem. Biophys. Res. Comm., 2005, 338:694-699.
Prasath, G.S., et al., Modulatory Effects of Fisetin, a Bioflavonoid, on Hyperglycemia by Attenuating the Key Enzymes of Carbohydrate Metabolism in Hepatic and Renal Tissues in Streptozotocin-Induced Diabetic Rats, Eur. J. Pharmacol., 2011, 668(3):492-496.
Venkatesan, B., et al., Resveratrol Inhibits PDGF Receptor Mitogenic Signaling in Mesangial Cells: Role of PTP1B, FASEB J., 2008, 22(10):3469-3482.
Brown, M.L., et al., Follistatin and Follistatin Like-3 Differentially Regulate Adiposity and Glucose Homeostasis, Obesity, 2011, 19(10):1940-1949.

* cited by examiner

*Primary Examiner* — Clinton Brooks
*Assistant Examiner* — Yih-Horng Shiao
(74) *Attorney, Agent, or Firm* — Pillsbury Winthrop Shaw Pittman LLP

(57) ABSTRACT

The invention provides methods, compositions, uses of compositions, assays and kits for modulating brown adipose tissue (BAT) in animals and patients with obesity, insulin resistance and perturbed glucose homeostasis are disclosed. Accordingly, methods, compositions, uses of compositions, and kits are useful for the amelioration of pathological conditions characterized by storage of excess energy, insulin resistance and related metabolic syndromes often associated with obesity.

13 Claims, 31 Drawing Sheets

FIG. 2A
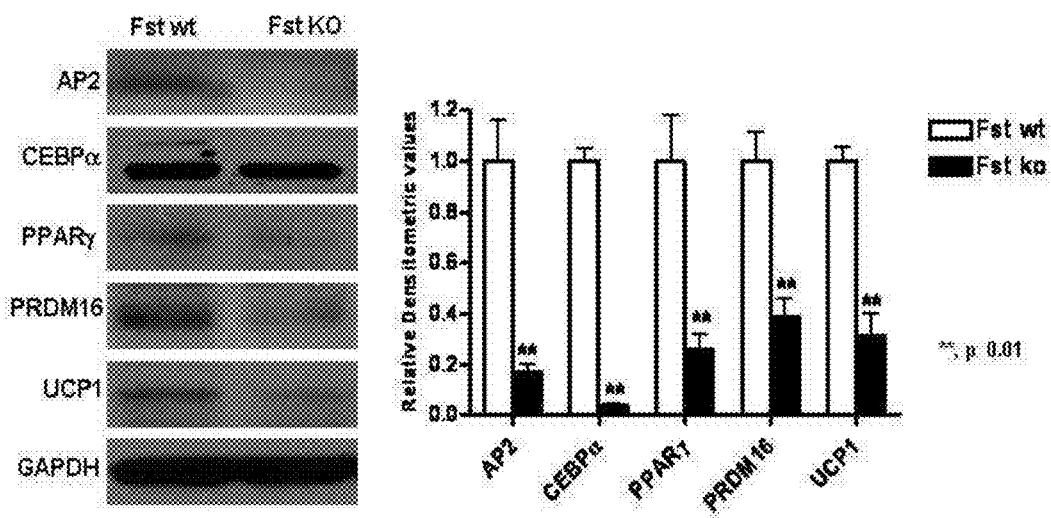
FIG. 2B
FIG. 2C

COMPOSITIONS AND METHODS FOR TREATING OR PREVENTING METABOLIC SYNDROME DISORDERS

CROSS-REFERENCE TO RELATED APPLICATIONS

This application is a National Stage application under 35 U.S.C. 371 of International Application No. PCT/US2013/034855 filed Apr. 1, 2013, which claims priority to U.S. Patent Application No. 61/618,603 filed Mar. 30, 2013, the contents of which are incorporated herein by reference in their entireties.

FIELD OF THE INVENTION

The present invention relates to follistatin modulating agents and methods of using the same.

BACKGROUND

Obesity is occurring at epidemic rates not only in United States of America but all around the World. According to the World Health Organization report, more than one billion adults (~15% of world population) are overweight (body mass index (BMI>25), over 300 million adults are truly obese (BMI>30) and these numbers are expected to increase by more than half again by the year 2025 (Tseng et al. Nat Rev Drug Discov. 2010; 9(6): 465-482). Obesity represents a major risk factor for the development of many of our most common medical conditions, including diabetes, insulin resistance, dyslipidemia, non-alcoholic fatty liver, cardiovascular disease and even some cancers (Haslam et al. Lancet. 2005; 366(9492):1197-209; Bhatia et al. Curr Opin Cardiol. 2012; 27(4):420-8). Accordingly, the economic impact of obesity continues to rise steeply. Obesity develops from perturbation of cellular bioenergetics, when energy uptake exceeds energy expenditure (Kajimura et al. Cell Metab. 2010; 11(4):257-62; Nedergaard et al. Cell Metab. 2011; 13(3):238-40). While most obesity therapies are focused on reducing caloric intake and exercise (Isidro et al. Mini Rev Med Chem. 2009; 9(6):664-73; Grundy, Nat Rev Drug Discov. 2006; 5(4):295-309), recent studies suggest that increasing cellular energy expenditure is an attractive alternative approach (Whittle et al. Trends Mol Med. 2011; 17(8):405-11; Boss et al. Front Endocrinol (Lausanne); 2012; 3:14).

Several biological mechanisms have been implicated in the development of obesity. For instance, the hormone leptin has been shown to regulate fat accumulation and eating behavior and numerous animal models of obesity have been established based on mutations in the leptin and leptin receptor genes. Obesity in turn has been implicated as a risk factor in diseases ranging from insulin resistance, type II diabetes, to metabolic syndrome, hypertension, cardiovascular disease, hyperlipidemia, sleep apnea, coronary artery disease, knee osteoarthritis, gout, infertility, breast cancer, endometrial cancer, gallbladder disease, colon cancer and lower back pain.

Currently available treatments for obesity are generally directed to suppressing appetite (diethylpropion tenuate, mazindol, orlistat, phendimetrazine, phentermine, and sibutramine), however these compounds may not be effective or appropriate in all subjects. Accordingly, new modes of treatment are needed and desirable. Treatments for diabetes are well known and include oral hypoglycemic agents such as sulfonylureas (tolbutamide, chlorpropamide and glibenclamide, biguanides (metformin and buformin), and α-glucosidase inhibitors (acarbose and voglibose). In addition, thiazolidinediones (troglitazone, rosiglitazone and pioglitazone), are commonly used to reduce insulin-resistance. However, thiazolidinediones are commonly associated with a weight gain and all anti-diabetic medications are associated with side effects. Thus, there is a still a need for more effective therapies for diabetes. We propose herein, agents and compounds modulating the expression of follistatin as therapeutics for the treatment or prevention of obesity, insulin resistance disorders and metabolic syndrome related disorders.

Follistatin binds to several members of the transforming growth factor-beta (TGF-β) family and blocks the interaction of these cytokines with their cognate receptors. Follistatin was first identified as a factor that could inhibit the release of follicle-stimulating hormone from pituitary cells (Ueno et al., 1987). It binds activins A, B and AB with high affinity and was also reported to bind activin E but not activin C (Nakamura et al., 1990; Schneider et al., 1994; Hashimoto et al., 2002; Wada et al., 2004). Follistatin-bound activin is unable to initiate signal transduction and consequently follistatin is a potent antagonist of physiological activin signals. Of the three follistatin domains present in all follistatin isoforms, (Shimasaki et al., 1988) the first two, but not the third, are necessary for activin A binding (Keutmann et al., 2004; Harrington et al., 2006). Aside from activins, follistatin also binds several bone morphogenetic proteins (BMP) including BMP2, BMP4, BMP6 and BMP7 (Iemura et al., 1998; Glister et al., 2004). In 2004 it was shown that follistatin binds myostatin (also known as growth and differentiation factor 8, GDF8) with high affinity and thereby is able to antagonize the inhibitory effect of myostatin on muscle growth (Amthor et al., 2004). Activin A is a critical component of the inflammatory response and follistatin can be used to block Activin A (Jones. et al. PNAS 2007).

The functional significance of the interaction between follistatin and angiogenin, a pro-angiogenic factor unrelated to the TGF-β family, remains to be determined (Gao, et al., 2007). The interaction of follistatin with heparin and heparin sulfates is isoform specific. For example, follistatin 288 binds to heparin sulfate, whereas this binding is blocked by the acidic tail of follistatin 315 (Sugino et al., 1993). Furthermore, myocytes and brown adipocyte cell lineages are interlinked, and this relationship between the cell lineages confirms a distinct origin of brown versus white adipose tissue. The relationship also provides an explanation, concerning the reason why brown adipocytes are connected with lipid metabolism rather than with energy storage. In that respect, brown adipose acts much like oxidative skeletal muscular tissue (Timmons, et al., PNAS, 2006). It has been determined that genes, including the muscle specific basic helix-loop-helix (bHLH) myogenic regulator myogenin, have been expressed in brown preadipocytes at a level which is comparable with differentiating confluent C2C12 myoblasts (Fulco et al. (2003) Mol Cell 12:51-62).

Brown adipose tissue (BAT) not only has a remarkable energy dissipating capacity but is also the most active tissue for promoting triglyceride clearance and glucose disposal and generates heat for thermogenic purposes (Bartelt et. al. Nat Med. 2011; 17(2):200-5). This specialized function of brown fat cells derives from high mitochondrial content and ability to uncouple cellular respiration through uncoupling protein-1 (UCP1) (Nedergaard et al. Cell Metab. 2011; 13(3):238-40.) The balance between white adipose tissue (WAT) and BAT affects systemic energy balance and is widely believed to be the key determinant during development of obesity and related metabolic syndrome (Kajimura et al. Cell Metab. 2010; 11(4):257-62; Nedergaard et al. Cell Metab. 2011; 13(3):238-40). Several lines of evidences suggest that BAT has anti-obesity function and that it protects from metabolic syndrome. Transgenic mice expressing UCP1 (a key BAT specific protein) under the control of fatty acid binding protein 4 (FABP4/AP2) promoter are resistant to genetic and diet-induced obesity (Hansen et al. Biochem J. 2006; 398(2):153-68). Targeted disruption of Cidea, which inhibits the uncoupling activity of UCP1, results in lean mice that are resistant to diet induced obesity (Zhou et al. Nat Genet. 2003; 35(1):49-56). Ectopic levels of BAT in mouse skeletal muscle have been shown to protect mice from high fat diet-induced metabolic syndrome with obesity, hyperglycemia, and insulin resistance (Almind et al. Proc Natl Acad Sci USA. 2007; 104(7):2366-71).

The prototypic androgens testosterone (T) and dihydrotestosterone (DHT) have been shown to up-regulate follistatin (Fst), an extracellular protein that binds activins and myostatin (Mst) with high affinity and inhibits TGF-β signaling in a variety of cell lines (Braga et al. Obesity, 2012 doi: 10.1038/oby.20117; Singh et al. Endocrinology. 2009; 150(3):1259-68; Braga et. al. Mol Cell Endo, 2012; 350(1): 39-52). Considerable evidence indicates that inhibition of TGF-β/Mst/Smad3 signaling promotes a WAT to BAT phenotype change, mitochondrial biogenesis and protects experimental mice from diet-induced obesity (Braga et al. Obesity, 2012 doi: 10.1038/oby.20117; Yadav et al. Cell Metab. 2011; 14(1):67-79; Zhang et al. Diabetologia. 2012; 55(1):183-93).

Previous studies have suggested blocking preadipocyte to adipocyte conversion as an effective approach to regulate adipose tissue growth (Wu et al 2010). While differential screening was used to identify follistatin-like 1 (Fstl1) as a potential target in the adipocyte differentiation pathway, it was suggested that blocking Fstl1 expression would block adipocyte differentiation.

In contrast to such teachings, it is disclosed herein that up regulation of a follistatin domain containing protein (follistatin) is positively associated with brown adipose tissue differentiation and that compounds increasing follistatin expression can be utilized to treat or prevent an obesity related disorder. Therefore, the present invention is surprising and unexpected in view of the prior art and addresses the need for novel compositions, medicinal formulations, uses, methods, kits, and combination therapies capable of preventing or safely treating serious chronic diseases, and assays for identifying further compounds and compositions useful for the same.

SUMMARY

Provided herein are methods and assays for screening compounds, agents, proteins, nucleic acids, and amino acids for follistatin modulating activity. In preferred embodiments, test cells are assessed for expression and/or activity of follistatin using RNA expression assays, PCR, microarray, northern blot, nucleic acid hybridization-based methods, rapid typing methods, according to expression of a reporter gene, of a marker gene, of a transgenic gene, of a fluorescent protein, of an antibiotic resistance protein, or using FACS sorting. Methods for screening for compounds, agents, proteins, nucleic acids, and amino acids for follistatin modulating activity include steps of contacting a cell lacking a functional follistatin gene (FST KO gene) with a compound, agent, protein, nucleic acid, or amino acid to be tested for follistatin modulating activity, and measuring the activity follistatin activity in the cell, where a difference in the measured follistatin activity in the cell and that of follistatin activity measured in a control cell indicates that the compound, agent, protein, nucleic acid, or amino acid modulated follistatin activity. Methods for screening for compounds, agents, proteins, nucleic acids, and amino acids for follistatin modulating activity include steps of contacting a FST KO animal, such as a FST KO mouse, with a compound, agent, protein, nucleic acid, or amino acid to be tested for follistatin modulating activity, and measuring the activity follistatin activity in the FST KO animal, where a difference in the measured follistatin activity in the FST KO and that of follistatin activity measured in a control animal indicates that the compound, agent, protein, nucleic acid, or amino acid modulated follistatin activity.

Also provided herein are methods wherein the cells are assessed for expression of follistatin using RNA expression assays, polymerase chain reaction (PCR), microarray, northern blot, nucleic acid hybridization-based methods, rapid typing methods, according to expression of a reporter gene, of a marker gene, of a transgenic gene, of a fluorescent protein, of an antibiotic resistance protein, or using fluorescence-activated cell sorting (FACS).

Provided herein are also methods of increasing the activity and/or protein level of follistatin in a subject are recited herein comprising administering to the subject a therapeutically effective amount of a compound that increases the activity and/or protein level of Fst and/or UCP-1. In certain embodiments the method comprises identifying agents for modulating the activity of follistatin by contacting a cell with a test agent and measuring one or more of the activity of follistatin, the level of follistatin protein, and the expression of genetic message encoding follistatin in a cell. In another embodiment, the method comprises identifying an agent for modulating the activity of UCP1 by contacting a cell with a test agent and measuring one or more of the activity of UCP-1, the level of UCP-1 protein, and the expression of genetic message encoding UCP-1 in a cell.

Further provided herein are methods for treating or preventing metabolic syndrome related disorders, and/or insulin resistance disorders, such as diabetes in a subject. In one embodiment, the method comprises administering to a subject in need thereof a therapeutically effective amount of an agent that increases the activity and/or protein level of a follistatin (GenBank Accession Number NG_028911) (SEQ ID NO: 1). The agent may be a follistatin-modulating compound, or prodrug thereof. The follistatin-modulating compound preferably stimulates human FST, i.e., FST, protein activity. The follistatin-modulating compound preferably is a compound, which has a formula selected from the group consisting of but not limited to, for example, single chain, soluble, gonadal proteins comprising between 288 and 315 amino acids with a molecular weight between 30,000 and 60,000 Daltons, or a prodrug thereof.

Follistatin-modulating compounds may be flavones, stilbenes, flavanones, isoflavones, catechins, chalcones, tannins and anthocyanidins or analogs or derivatives thereof. Further, histone deacetylase (HDAC) inhibitors such as trichostatin or valproic acid display an increased production of follistatin. Likewise, follistatin-modulating compounds may be selected from the group consisting of resveratrol, butein, piceatannol, isoliquiritgenin, fisetin, luteolin, 3,6,3',4'-tetrahydroxyfalvone, quercetin, nitric oxide and analogs and derivatives thereof. Preferred follistatin activating compounds also increase the activity and/or protein level of UCP-1.

Methods for reducing weight or preventing weight gain in a subject are recited herein, comprising administering to the subject a therapeutically effective amount of a compound that increases the activity and/or protein level of Fst and/or UCP-1. In certain embodiments, the compositions and methods comprise use of follistatin, its analogs and derivatives to reduce a subject's high fat food cravings and consumption.

Methods for promoting weight gain in a subject (e.g., a cachectic patient) are also recited herein, comprising administering to a subject in need thereof a therapeutically effective amount of an agent that decreases the activity and/or protein level of a follistatin. Preferably, the follistatin-inhibitory compound is a compound selected from the group of compounds, or a prodrug thereof. Preferred follistatin inhibitory compounds also decrease or inhibit the activity and/or protein level of UCP-1. In certain embodiments, the method further comprises administering to the subject a therapeutically effective amount of a second agent that: (i) decreases the activity and/or protein level of a follistatin; (ii) decreases the activity and or protein level of UCP-1; or (iii) is an agent for promoting weight gain.

In certain embodiments, the method further comprises administering to the subject a therapeutically effective amount of a second agent that: (i) increases the activity and/or protein level of UCP-1; (ii) increases the activity and/or protein level of a follistatin; (iii) is an anti-diabetic agent; or (iv) is an anti-obesity agent. In certain embodiments, the compositions and methods further comprise claim combinations involving folistatin modulating compounds and current FDA approved drugs. FDA approved drugs may include those of the antihypertensive, anti-glycemic, anti-lipidemic, or a cholesterol-lowering class of drugs.

Use of a follistatin-modulating compound, alone or in conjunction with a second agent, for treating or preventing a metabolic syndrome related disorder and/or an insulin resistance disorder is also recited herein. In addition, the use of a follistatin inhibitory compound, alone or in conjunction with a second agent, for promoting weight gain in a subject is provided herein.

In this study, we assessed the role of Fst during BAT differentiation, energy metabolism and diet-induced obesity using both in vitro and in vivo models. We report here that Fst is a novel inducer of BAT differentiation and BAT mass. Since Fst KO mice are not viable (Matzuk et al. Nature. 1995; 374(6520):360-3), we isolated primary MEF cultures from both Fst KO and WT embryos and allowed them to differentiate under BAT-specific conditions. Our data provides a clear evidence that Fst loss of function is associated with a significant down-regulation of UCP1, PRDM16, PGC-1α and several markers implicated in BAT differentiation as well as energy and lipid metabolism. On the other hand, our in vivo data obtained from Fst-transgenic (Fst-Tg) mice suggest increased expression of these BAT-specific proteins in muscle as well as in both WAT and BAT tissues compared to their expression in similar tissues obtained from WT mice. Fst-Tg mice are resistant to diet-induced increase in body weight and fat mass as well as increase in triglyceride (TG) and free-fatty acids (FFA) levels. Furthermore, glucose clearance rate of these Fst-Tg mice were significantly higher compared to the age-matched WT mice. Thus, our data provide clear evidence regarding the novel role of Fst in BAT differentiation and lipid metabolism and reveals a translational potential for developing therapeutic interventions for obesity and related metabolic disorders.

In one aspect, the present invention provides a method of increasing follistatin activity that leads to improved glucose handling, an improved lipid profile, reduced food intake, and reduced body fat.

In another aspect, the present invention provides a method of treating a metabolic syndrome like disorder or an insulin resistance disorder in a subject in need thereof, comprising administering to the subject a therapeutically effective amount of a compound that increases the activity and/or protein level of follistatin (Fst) and/or uncoupling protein 1 (UCP-1).

In one embodiment of the treatment method, the compound used in the method is a UCP-1-activating compound, or a salt thereof. In another embodiment, the compound used in the method is an Fst-activating compound, or salt thereof. In another embodiment, the compound is selected from the group consisting of resveratrol, butein, fisetin, piceatannol, quercetin and 3,5-dihydroxy-4-'-thiomethyl-trans-stilbene. In another embodiment, the compound is selected from the group of compounds consisting of stilbenes, chalcones, flavanones, isoflavanones, and anthocyanidins. In other embodiments, the disease is an insulin resistance disorder such as diabetes, obesity, or a metabolic syndrome related disorder.

In a particular embodiments of the method, the compound activates UCP-1 by a factor of at least about 1.5, 2, 2.5, 3, 3.5, 4, 4.5 or 5, Fst by a factor of at least about 1.5, 2, 2.5, 3, 3.5, 4, 4.5 or 5 and/or adiponectin by a factor of at least about 1.5, 2, 4, 5, 10, 15 or 20. In other embodiments of the method, the compound has an $EC_{50}$ for activating UCP1 that is less than about 100 μM and/or an $EC_{50}$ for activating adiponectin that is less than about 10 μM.

In another aspect of the present invention, the method of treatment further comprises administering to the subject a second agent that: increases the activity or protein level of adiponectin in a cell; increases the activity or protein level of 5'-AMP-activated protein kinase (AMPK) in a cell; is an anti-diabetic agent; or is an anti-obesity agent. In certain embodiments of the method, the compound does not substantially inhibit the catalytic activity of cyclooxygenase, PI3-kinase, and/or tyrosine protein kinase.

Another aspect of the present invention are methods of reducing weight and/or preventing weight gain in a subject in need thereof, comprising administering to the subject a therapeutically effective amount of a compound that increases the activity and/or protein level of UCP-1 and/or increases the activity and/or protein level of Fst.

Another aspect of the present invention is a method of increasing the activity and/or protein level of follistatin in a subject in need thereof, comprising administering to the subject a therapeutically effective amount of a compound that increases the activity and/or protein level of UCP-1 and/or increases the activity and/or protein level of Fst. In one embodiment, the method of increasing the activity and/or protein level of UCP-1 in a subject in need thereof, comprises administering to the subject a therapeutically effective amount of a compound selected from the group of compounds consisting of resveratrol (3,5,4'-Trihydroxy-trans-stilbene, butein (3,4,2',4' Tetrahydroxychalcone), piceatannol (3,5,3',4'-Tetrahydroxy-trans-stilbene), isoliquiritigenin (4,2',4'-Trihydroxychalcone), fisetin (3,7,3', 4'-Tetrahydroxyflavone), quercetin (3,5,7,3'4'-Pentahydroxyflavone), Deoxyrhaponticin (3,5-Dihydroxy-4'-methoxystilbene 3-O-β-D-glucoside), trans-Stilbene, Rhapontin (3,3',5,3-Trihydroxy-4'-methoxystilbene, cyaniding 3-O-β-D-glucoside), cis-Stilbene, Dehydroabietic acid (DAA), 5,7,3',4'-Tetrahydroxyflavone, 4'-Hydroxyflavone, 5,7-Dihydroxyflavone, chrysin, Morin (3,5,7,2',4'-Pentahydroxyflavone), Flavone, 5-Hydroxyflavone, (−)-Epicatechin, (−)-Catechin, (−)-Gallocatechin, (+)-Catechin, 5,7,3',4',5'-pentahydroxyflavone, Luteolin (5,7,3',4'-Tetrahydroxyflavone), 7,3',4',5'-Tetrahydroxyflavone; Kaempferol (3,5,7,4'-Tetrahydroxyflavone), 6-Hydroxyapigenin (5,6,7,4'-Tetrahydoxyflavone) (Scutellarein), Apigenin (5,7,4'-Trihydroxyflavone), 3,6,2',4'-Tetrahydroxyflavone, 7,4'-Dihydroxyflavone, Daidzein (7,4'-Dihydroxyisoflavone), Genistein (5,7,4'-Trihydroxyflavanone), Naringenin (5,7,4'-Trihydroxyflavanone), 3,5,7,3',4'-Pentahydroxyflavanone (Flavanone); Pelargonidin chloride (3,5,7,4'-Tetrahydroxyflavylium chloride), Hinokitiol (b-Thujaplicin; 2-hydroxy-4-isopropyl-2,4,6-cycloheptatrien-1-one), L-(+)-Ergothioneine ((S)-a-Carboxy-2,3-dihydro-N,N,N-trimethyl-2-thioxo-1H-imidazole-4-ethanaminium inner salt), Caffeic Acid Phenyl Ester, MCI-186 (3-Methyl-1-phenyl-2-pyrazolin-5-one), HBED (N,N'-Di-(2-hydroxybenzyl)ethylenediamine-N,N'-diacetic acid*H20), Ambroxol (trans-4-(2-Amino-3,5-dibromobenzylamino)cyclohexane-HCl, U-83836E ((−)-2-((4-(2,6-di-1-Pyrrolidinyl-4-pyrimidinyl)-1-piperzainyl)methyl)-3,4-dihydro-2,5,7,8-tetramethyl-2H-1-benzopyran-6-ol-2HCl), progesterone, epithelial Gli2, adeno-associated virus serotype 1 vector, AAV1-FS344, guaifenesin dinitrate (GDN), nitric oxide donors, deacetylase inhibitors, and HDAC inhibitor trichostatin A (TSA).

In particular aspects of the claimed methods the subject is a human.

Additional aspects of the invention comprise use of a compound that increases the activity and/or protein level of uncoupling protein 1 (UCP-1) for treating a metabolic syndrome related disorder or an insulin resistance disorder. In one embodiment, the compound is a UCP-1-activating compound, or a salt thereof. In another embodiment, the compound is an Fst-activating compound, or salt thereof. In another embodiment of the claimed use, the compound is selected from the group consisting of resveratrol, butein, fisetin, piceatannol, quercetin and 3,5-dihydroxy-4-'-thiomethyl-trans-stilbene. In another embodiment of the claimed use, the compound is selected from the group of compounds consisting of stilbenes, chalcones, flavanones, isoflavanones, and anthocyanidins. In specific embodiments of the use, the disease can be an insulin resistance disorder such as diabetes, obesity or a metabolic syndrome related disorder. In particular embodiments, the compound activates UCP-1 by a factor of at least about 1.5, 2, 2.5, 3, 3.5, 4, 4.5 or 5, Fst by a factor of at least about 1.5, 2, 2.5, 3, 3.5, 4, 4.5 or 5 and/or adiponectin by a factor of at least about 1.5, 2, 4, 5, 10, 15 or 20. In other embodiments of the compound has an $EC_{50}$ for activating UCP-1 that is less than about 100 μM, an $EC_{50}$ for activating Fst that is less than about 100 μM, and/or an $EC_{50}$ for activating adiponectin that is less than about 10 μM.

In another aspect of the invention, the use further comprises administering to the subject a second agent that: increases the activity or protein level of adiponectin in a cell; increases the activity or protein level of 5'-AMP-activated protein kinase (AMPK) in a cell; is an anti-diabetic agent; or is an anti-obesity agent. In particular embodiments of the invention, the compound does not substantially inhibit the catalytic activity of cyclooxygenase, PI3-kinase, and/or tyrosine protein kinase.

In another aspect of the invention, the use of a compound increases the activity and/or protein level of UCP-1 for reducing weight and/or the activity and/or protein level of Fst for reducing weight.

In another aspect of the invention, the use of a compound increases the activity and/or protein level of UCP-1 for preventing weight gain and/or the activity and/or protein level of Fst for preventing weight gain.

In another aspect of the invention, the use of a compound increases the activity and/or protein level of UCP-1 for increasing the activity and/or protein level of follistatin; and/or the activity and/or protein level of Fst for increasing the activity and/or protein level of UCP-1.

In another aspect of the invention, the use of a compound increases the activity and/or protein level of UCP-1 for increasing the activity and/or protein level of UCP1 and/or Fst, wherein the compound is selected from the group of compounds resveratrol, butein, fisetin, piceatannol, quercetin and 3,5-dihydroxy-4-'-thiomethyl-trans-stilbene; and/or increases the activity and/or protein level of Fst for increasing the activity and/or protein level of UCP1 and/or Fst, wherein the compound is selected from the group of compounds resveratrol, butein, fisetin, piceatannol, quercetin and 3,5-dihydroxy-4-'-thiomethyl-trans-stilbene. In certain embodiments, the use of a compound that increases the activity and/or protein level of UCP-1 for increasing the activity and/or protein level of UCP-1 is selected from the group of compounds consisting of resveratrol (3,5,4'-Trihydroxy-trans-stilbene, butein (3,4,2',4' Tetrahydroxychalcone), piceatannol (3,5,3',4'-Tetrahydroxy-trans-stilbene), isoliquiritigenin (4,2',4'-Trihydroxychalcone), fisetin (3,7,3',4'-Tetrahydroxyflavone), quercetin (3,5,7,3'4'-Pentahydroxyflavone), Deoxyrhaponticin (3,5-Dihydroxy-4'-methoxystilbene 3-O-β-D-glucoside), trans-Stilbene, Rhapontin (3,3',5,3-Trihydroxy-4'-methoxystilbene, cyaniding 3-O-β-D-glucoside), cis-Stilbene, Dehydroabietic acid (DAA), 5,7,3',4'-Tetrahydroxyflavone, 4'-Hydroxyflavone, 5,7-Dihydroxyflavone, chrysin, Morin (3,5,7,2',4'-Pentahydroxyflavone), Flavone, 5-Hydroxyflavone, (−)-Epicatechin, (−)-Catechin, (−)-Gallocatechin, (+)-Catechin, 5,7,3',4',5'-pentahydroxyflavone, Luteolin (5,7,3',4'-Tetrahydroxyflavone), 7,3',4',5'-Tetrahydroxyflavone; Kaempferol (3,5,7,4'-Tetrahydroxyflavone), 6-Hydroxyapigenin (5,6,7,4'-Tetrahydoxyflavone) (Scutellarein), Apigenin (5,7,4'-Trihydroxyflavone), 3,6,2',4'-Tetrahydroxyflavone, 7,4'-Dihydroxyflavone, Daidzein (7,4'-Dihydroxyisoflavone), Genistein (5,7,4'-Trihydroxyflavanone), Naringenin (5,7,4'-Trihydroxyflavanone), 3,5,7,3',4'-Pentahydroxyflavanone (Flavanone); Pelargonidin chloride (3,5,7,4'-Tetrahydroxyflavylium chloride), Hinokitiol (b-Thujaplicin; 2-hydroxy-4-isopropyl-2,4,6-cycloheptatrien-1-one), L-(+)-Ergothioneine ((S)-a-Carboxy-2,3-dihydro-N,N,N-trimethyl-2-thioxo-1H-imidazole-4-ethanaminium inner salt), Caffeic Acid Phenyl Ester, MCI-186 (3-Methyl-1-phenyl-2-pyrazolin-5-one), HBED (N,N'-Di-(2-hydroxybenzyl)ethylenediamine-N,N'-diacetic acid*H20), Ambroxol (trans-4-(2-Amino-3,5-dibromobenzylamino)cyclohexane-HCl, U-83836E ((−)-2-((4-(2,6-di-1-Pyrrolidinyl-4-pyrimidinyl)-1-piperzainyl)methyl)-3,4-dihydro-2,5,7,8-tetramethyl-2H-1-benzopyran-6-ol-2HCl), progesterone, epithelial Gli2, adeno-associated virus serotype 1 vector, AAV1-FS344, guaifenesin dinitrate (GDN), nitric oxide donors, deacetylase inhibitors, and HDAC inhibitor trichostatin A (TSA).

Another aspect of the invention is a method for identifying an agent for modulating the activity of follistatin, comprising contacting a cell with a test agent and measuring one or more of the activity of follistatin, the level of follistatin protein, and the expression of genetic message encoding follistatin in said cell. In one embodiment, the method for identifying an agent for modulating the activity of uncoupling protein 1 (UCP1) comprises contacting a cell with a test agent and measuring one or more of the activity of UCP-1, the level of UCP-1 protein, and the expression of genetic message encoding UCP-1 in said cell.

Yet another aspect of the present invention is a pharmaceutical composition for treating a metabolic syndrome related disorder or insulin resistance in a subject. In one embodiment, the compound is selected from the group consisting of resveratrol, butein, fisetin, piceatannol, quercetin and 3,5-dihydroxy-4-'-thiomethyl-trans-stilbene, and a pharmaceutically acceptable carrier. In another embodiment, the compound is selected from the group consisting of stilbenes, chalcones, flavanones, isoflavanones, and anthocyanidins, and a pharmaceutically acceptable carrier. In yet another embodiment, the pharmaceutical composition for treating a metabolic syndrome related disorder or insulin resistance in a subject, is a compound selected from the group consisting of resveratrol (3,5,4'-Trihydroxy-trans-stilbene, butein (3,4,2',4' Tetrahydroxychalcone), piceatannol (3,5,3',4'-Tetrahydroxy-trans-stilbene), isoliquiritigenin (4,2',4'-Trihydroxychalcone), fisetin (3,7,3',4'-Tetrahydroxyflavone), quercetin (3,5,7,3'4'-Pentahydroxyflavone), Deoxyrhaponticin (3,5-Dihydroxy-4'-methoxystilbene 3-O-β-D-glucoside), trans-Stilbene, Rhapontin (3,3',5,3-Trihydroxy-4'-methoxystilbene, cyaniding 3-O-β-D-glucoside), cis-Stilbene, Dehydroabietic acid (DAA), 5,7,3',4'-Tetrahydroxyflavone, 4'-Hydroxyflavone, 5,7-Dihydroxyflavone, chrysin, Morin (3,5,7,2',4'-Pentahydroxyflavone), Flavone, 5-Hydroxyflavone, (–)-Epicatechin, (–)-Catechin, (–)-Gallocatechin, (+)-Catechin, 5,7,3',4',5'-pentahydroxyflavone, Luteolin (5,7,3',4'-Tetrahydroxyflavone), 7,3',4',5'-Tetrahydroxyflavone; Kaempferol (3,5,7,4'-Tetrahydroxyflavone), 6-Hydroxyapigenin (5,6,7,4'-Tetrahydoxyflavone) (Scutellarein), Apigenin (5,7,4'-Trihydroxyflavone), 3,6,2',4'-Tetrahydroxyflavone, 7,4'-Dihydroxyflavone, Daidzein (7,4'-Dihydroxyisoflavone), Genistein (5,7,4'-Trihydroxyflavanone), Naringenin (5,7,4'-Trihydroxyflavanone), 3,5,7,3',4'-Pentahydroxyflavanone (Flavanone); Pelargonidin chloride (3,5,7,4'-Tetrahydroxyflavylium chloride), Hinokitiol (b-Thujaplicin; 2-hydroxy-4-isopropyl-2,4,6-cycloheptatrien-1-one), L-(+)-Ergothioneine ((S)-a-Carboxy-2,3-dihydro-N,N,N-trimethyl-2-thioxo-1H-imidazole-4-ethanaminium inner salt), Caffeic Acid Phenyl Ester, MCI-186 (3-Methyl-1-phenyl-2-pyrazolin-5-one), HBED (N,N'-Di-(2-hydroxybenzyl)ethylenediamine-N,N'-diacetic acid*H20), Ambroxol (trans-4-(2-Amino-3,5-dibromobenzylamino)cyclohexane-HCl, U-83836E ((–)-2-((4-(2,6-di-1-Pyrrolidinyl-4-pyrimidinyl)-1-piperzainyl)methyl)-3,4-dihydro-2,5,7,8-tetramethyl-2H-1-benzopyran-6-ol-2HCl), progesterone, epithelial Gli2, adeno-associated virus serotype 1 vector, AAV1-FS344, guaifenesin dinitrate (GDN), nitric oxide donors, deacetylase inhibitors, and HDAC inhibitor trichostatin A, and a pharmaceutically acceptable carrier.

Additional aspects of the invention are pharmaceutical compositions for reducing weight or preventing weigh gain in a subject. In one embodiment, the compound is selected from the group consisting of resveratrol, butein, fisetin, piceatannol, quercetin and 3,5-dihydroxy-4-'-thiomethyl-trans-stilbene, and a pharmaceutically acceptable carrier. In another embodiment, the compound is selected from the group consisting of stilbenes, chalcones, flavanones, isoflavanones, and anthocyanidins, and a pharmaceutically acceptable carrier. In yet another embodiment, the compound is selected from the group consisting of resveratrol (3,5,4'-Trihydroxy-trans-stilbene, butein (3,4,2',4' Tetrahydroxychalcone), piceatannol (3,5,3',4'-Tetrahydroxy-trans-stilbene), isoliquiritigenin (4,2',4'-Trihydroxychalcone), fisetin (3,7,3',4'-Tetrahydroxyflavone), quercetin (3,5,7,3'4'-Pentahydroxyflavone), Deoxyrhaponticin (3,5-Dihydroxy-4'-methoxystilbene 3-O-β-D-glucoside), trans-Stilbene, Rhapontin (3,3',5,3-Trihydroxy-4'-methoxystilbene, cyaniding 3-O-β-D-glucoside), cis-Stilbene, Dehydroabietic acid (DAA), 5,7,3',4'-Tetrahydroxyflavone, 4'-Hydroxyflavone, 5,7-Dihydroxyflavone, chrysin, Morin (3,5,7,2',4'-Pentahydroxyflavone), Flavone, 5-Hydroxyflavone, (–)-Epicatechin, (–)-Catechin, (–)-Gallocatechin, (+)-Catechin, 5,7,3',4',5'-pentahydroxyflavone, Luteolin (5,7,3',4'-Tetrahydroxyflavone), 7,3',4',5'-Tetrahydroxyflavone; Kaempferol (3,5,7,4'-Tetrahydroxyflavone), 6-Hydroxyapigenin (5,6,7,4'-Tetrahydoxyflavone) (Scutellarein), Apigenin (5,7,4'-Trihydroxyflavone), 3,6,2',4'-Tetrahydroxyflavone, 7,4'-Dihydroxyflavone, Daidzein (7,4'-Dihydroxyisoflavone), Genistein (5,7,4'-Trihydroxyflavanone), Naringenin (5,7,4'-Trihydroxyflavanone), 3,5,7,3',4'-Pentahydroxyflavanone (Flavanone); Pelargonidin chloride (3,5,7,4'-Tetrahydroxyflavylium chloride), Hinokitiol (b-Thujaplicin; 2-hydroxy-4-isopropyl-2,4,6-cycloheptatrien-1-one), L-(+)-Ergothioneine ((S)-a-Carboxy-2,3-dihydro-N,N,N-trimethyl-2-thioxo-1H-imidazole-4-ethanaminium inner salt), Caffeic Acid Phenyl Ester, MCI-186 (3-Methyl-1-phenyl-2-pyrazolin-5-one), HBED (N,N'-Di-(2-hydroxybenzyl)ethylenediamine-N,N'-diacetic acid*H20), Ambroxol (trans-4-(2-Amino-3,5-dibromobenzylamino)cyclohexane-HCl, U-83836E ((–)-2-((4-(2,6-di-1-Pyrrolidinyl-4-pyrimidinyl)-1-piperzainyl)methyl)-3,4-dihydro-2,5,7,8-tetramethyl-2H-1-benzopyran-6-ol-2HCl), progesterone, epithelial Gli2, adeno-associated virus serotype 1 vector, AAV1-FS344, guaifenesin dinitrate (GDN), nitric oxide donors, deacetylase inhibitors, and HDAC inhibitor trichostatin A, and a pharmaceutically acceptable carrier.

Another aspect of the invention is a pharmaceutical composition for increasing the activity and/or protein level of follistatin in a subject. In one embodiment, the compound is selected from the group consisting of resveratrol, butein, fisetin, piceatannol, quercetin and 3,5-dihydroxy-4-'-thiomethyl-trans-stilbene, and a pharmaceutically acceptable carrier. In another embodiment the compound is selected from the group consisting of stilbenes, chalcones, flavanones, isoflavanones, and anthocyanidins, and a pharmaceutically acceptable carrier. In yet another embodiment, the compound is selected from the group consisting of resveratrol (3,5,4'-Trihydroxy-trans-stilbene, butein (3,4,2',4' Tetrahydroxychalcone), piceatannol (3,5,3',4'-Tetrahydroxy-trans-stilbene), isoliquiritigenin (4,2',4'-Trihydroxychalcone), fisetin (3,7,3',4'-Tetrahydroxyflavone), quercetin (3,5,7,3'4'-Pentahydroxyflavone), Deoxyrhaponticin (3,5-Dihydroxy-4'-methoxystilbene 3-O-β-D-glucoside), trans-Stilbene, Rhapontin (3,3',5,3-Trihydroxy-4'-methoxystilbene, cyaniding 3-O-β-D-glucoside), cis-Stilbene, Dehydroabietic acid (DAA), 5,7,3',4'-Tetrahydroxyflavone, 4'-Hydroxyflavone, 5,7-Dihydroxyflavone, chrysin, Morin (3,5,7,2',4'-Pentahydroxyflavone), Flavone, 5-Hydroxyflavone, (–)-Epicatechin, (–)-Catechin, (–)-Gallocatechin, (+)-Catechin, 5,7,3',4',5'-pentahydroxyflavone, Luteolin (5,7,3',4'-Tetrahydroxyflavone), 7,3',4',5'-Tetrahydroxyflavone; Kaempferol (3,5,7,4'-Tetrahydroxyflavone), 6-Hydroxyapigenin (5,6,7,4'-Tetrahydoxyflavone) (Scutellarein), Apigenin (5,7,4'-Trihydroxyflavone), 3,6,2',4'-Tetrahydroxyflavone, 7,4'-Dihydroxyflavone, Daidzein (7,4'-Dihydroxyisoflavone), Genistein (5,7,4'-Trihydroxyflavanone), Naringenin (5,7,4'-Trihydroxyflavanone), 3,5,7,3',4'-Pentahydroxyflavanone (Flavanone); Pelargonidin chloride (3,5,7,4'-Tetrahydroxyflavylium chloride), Hinokitiol (b-Thujaplicin; 2-hydroxy-4-isopropyl-2,4,6-cycloheptatrien-1-one), L-(+)-Ergothioneine ((S)-a-Carboxy-2,3-dihydro-N,N,N-trimethyl-2-thioxo-1H-imidazole-4-ethanaminium inner salt), Caffeic Acid Phenyl Ester, MCI-186 (3-Methyl-1-phenyl-2-pyrazolin-5-one), HBED (N,N'-Di-(2-hydroxybenzyl)ethylenediamine-N,N'-diacetic acid*H20), Ambroxol (trans-4-(2-Amino-3,5-dibromobenzylamino)cyclohexane-HCl, U-83836E ((−)-2-((4-(2,6-di-1-Pyrrolidinyl-4-pyrimidinyl)-1-piperzainyl)methyl)-3,4-dihydro-2,5,7,8-tetramethyl-2H-1-benzopyran-6-ol-2HCl), progesterone, epithelial Gli2, adeno-associated virus serotype 1 vector, AAV1-FS344, guaifenesin dinitrate (GDN), nitric oxide donors, deacetylase inhibitors, and HDAC inhibitor trichostatin A, and a pharmaceutically acceptable carrier.

Another aspect of the invention is a pharmaceutical composition for increasing the activity and/or protein level of UCP1 in a subject. In one embodiment the compound is selected from the group consisting of resveratrol, butein, fisetin, piceatannol, quercetin and 3,5-dihydroxy-4-'-thiomethyl-trans-stilbene, and a pharmaceutically acceptable carrier. In another embodiment the compound is selected from the group consisting of stilbenes, chalcones, flavanones, isoflavanones, and anthocyanidins, and a pharmaceutically acceptable carrier. In yet another embodiment the compound is selected from the group consisting of resveratrol (3,5,4'-Trihydroxy-trans-stilbene, butein (3,4,2',4' Tetrahydroxychalcone), piceatannol (3,5,3',4'-Tetrahydroxy-trans-stilbene), isoliquiritigenin (4,2',4'-Trihydroxychalcone), fisetin (3,7,3',4'-Tetrahydroxyflavone), quercetin (3,5,7,3'4'-Pentahydroxyflavone), Deoxyrhaponticin (3,5-Dihydroxy-4'-methoxystilbene 3-O-β-D-glucoside), trans-Stilbene, Rhapontin (3,3',5,3-Trihydroxy-4'-methoxystilbene, cyaniding 3-O-β-D-glucoside), cis-Stilbene, Dehydroabietic acid (DAA), 5,7,3',4'-Tetrahydroxyflavone, 4'-Hydroxyflavone, 5,7-Dihydroxyflavone, chrysin, Morin (3,5,7,2',4'-Pentahydroxyflavone), Flavone, 5-Hydroxyflavone, (−)-Epicatechin, (−)-Catechin, (−)-Gallocatechin, (+)-Catechin, 5,7,3',4',5'-pentahydroxyflavone, Luteolin (5,7,3',4'-Tetrahydroxyflavone; 7,3',4',5'-Tetrahydroxyflavone; Kaempferol (3,5,7,4'-Tetrahydroxyflavone), 6-Hydroxyapigenin (5,6,7,4'-Tetrahydoxyflavone) (Scutellarein), Apigenin (5,7,4'-Trihydroxyflavone), 3,6,2',4'-Tetrahydroxyflavone, 7,4'-Dihydroxyflavone, Daidzein (7,4'-Dihydroxyisoflavone), Genistein (5,7,4'-Trihydroxyflavanone), Naringenin (5,7,4'-Trihydroxyflavanone), 3,5,7,3',4'-Pentahydroxyflavanone (Flavanone); Pelargonidin chloride (3,5,7,4'-Tetrahydroxyflavylium chloride), Hinokitiol (b-Thujaplicin; 2-hydroxy-4-isopropyl-2,4,6-cycloheptatrien-1-one), L-(+)-Ergothioneine ((S)-a-Carboxy-2,3-dihydro-N,N,N-trimethyl-2-thioxo-1H-imidazole-4-ethanaminium inner salt), Caffeic Acid Phenyl Ester, MCI-186 (3-Methyl-1-phenyl-2-pyrazolin-5-one), HBED (N,N'-Di-(2-hydroxybenzyl)ethylenediamine-N,N'-diacetic acid*H20), Ambroxol (trans-4-(2-Amino-3,5-dibromobenzylamino)cyclohexane-HCl, U-83836E ((−)-2-((4-(2,6-di-1-Pyrrolidinyl-4-pyrimidinyl)-1-piperzainyl)methyl)-3,4-dihydro-2,5,7,8-tetramethyl-2H-1-benzopyran-6-ol-2HCl), progesterone, epithelial Gli2, adeno-associated virus serotype 1 vector, AAV1-FS344, guaifenesin dinitrate (GDN), nitric oxide donors, deacetylase inhibitors, and HDAC inhibitor trichostatin A, and a pharmaceutically acceptable carrier.

Another aspect of the invention is a kit for treating insulin resistance or a metabolic syndrome like disorder in a subject, comprising a pharmaceutical composition of a compound that increases the activity and/or protein level of UCP1, and instructions for its use.

Another aspect of the invention is kit for reducing weight or preventing weight gain in a subject, comprising a pharmaceutical composition of compound that increases the activity and/or protein level of UCP1, and instructions for its use.

Another aspect of the invention is a kit for increasing the activity and/or protein level of follistatin in a subject, comprising a pharmaceutical composition of a compound that increases the activity and/or protein level of UCP1, and instructions for its use. Another aspect of the invention is a kit for screening a compound, agent, nucleic acid or protein for the ability to increase Fst and/or UCP-1 activity and/or protein level.

Another aspect of the invention is a method of treating a metabolic syndrome related disorder or an insulin resistance disorder in a subject in need thereof, comprising 1) administering to the subject a therapeutically effective amount of a compound that increases the activity and/or protein level of uncoupling protein 1 (UCP1), and 2) administering to the subject a therapeutically effective amount of a second agent that: (i) increases the activity and/or protein level of uncoupling protein 1 (UCP1); (ii) increases the activity and/or protein level of a follistatin; (iii) is an anti-diabetic agent; or (iv) is an anti-obesity agent.

Another aspect of the method for reducing weight or preventing weight gain in a subject comprises administering to the subject a therapeutically effective amount of a second agent that: (i) increases the activity and/or protein level of uncoupling protein 1 (UCP1); (ii) increases the activity and/or protein level of a follistatin; (iii) is an anti-diabetic agent; or (iv) is an anti-obesity agent.

Another aspect of the various uses of the present invention is the further use of a second agent that: (i) increases the activity and/or protein level of uncoupling protein 1 (UCP-1); (ii) increases the activity and/or protein level of a follistatin; (iii) is an anti-diabetic agent; or (iv) is an anti-obesity agent.

Another aspect of the present invention is a method for the treatment or prevention of a disease related to a metabolic syndrome in a subject in need thereof, comprising administering to the subject a therapeutically effective amount of a compound that increases the activity and/or protein level of folistatin.

In one embodiment a pharmaceutical composition is used for treating or preventing a metabolic syndrome in a subject that comprises a compound that modulates the activity and/or protein level of folistatin, and a pharmaceutically acceptable carrier. In another embodiment, the pharmaceutical composition for treating or preventing a metabolic syndrome in a subject, is a compound that modulates nitric oxide production, and a pharmaceutically acceptable carrier. In yet another embodiment, the pharmaceutical composition for treating or preventing a metabolic syndrome in a subject is a compound that modulates histone deacetylase activity, and a pharmaceutically acceptable carrier. In another aspect of the invention, the composition further comprises the use of one or more FDA approved drugs in combination with folistatin modulating compounds. In one embodiment, the FDA approved drug is selected from a class of drugs including antihypertensive, anti-glycemic, anti-lipidemic, and cholesterol-lowering drugs.

Another aspect of the invention is a method for reducing high fat food cravings and consumption in a subject, comprising administering to the subject a therapeutically effective amount of a compound that increases the activity and/or protein level of folistatin. In another aspect of the invention a pharmaceutical composition is used for treating or preventing a metabolic syndrome in a subject, comprising a compound that modulates the activity and/or protein level of folistatin, and a pharmaceutically acceptable carrier. In one embodiment the pharmaceutical composition for treating or preventing a metabolic syndrome in a subject comprises a compound that modulates nitric oxide production, and a pharmaceutically acceptable carrier. In another embodiment, the pharmaceutical composition for treating or preventing a metabolic syndrome in a subject comprises a compound that modulates histone deacetylase activity, and a pharmaceutically acceptable carrier. In yet another embodiment, the method f or reducing high fat food cravings and consumption further comprises the use of one or more FDA approved drugs in combination with folistatin modulating compounds. In another embodiment, the FDA approved drug is selected from a class of drugs including antihypertensive, anti-glycemic, anti-lipidemic, and cholesterol-lowering drugs.

Additional aspects of the invention include a method for identifying, method of treatment and/or use of an agent, or a pharmaceutical composition of an agent, that modulates a common subset of genes that are reciprocally regulated via the Fst/Mst axis. In additional embodiments, the method or use is capable of identifying an agent that upregulates one or more of 17 genes selected from olfactory receptor 1509 (Olfr 1509); RIO kinase 3 (Riok3; yeast); kinesin family member 5B; ribosomal protein S25 (Rps25); UDP-N-acetyl-alpha-D-galactosamine:polypeptide N-Galnt14; acetylgalactosaminyltransferase; microtubule-associated protein 2 (Mtap2); RIKEN cDNA D230004N17 gene (D230004N17R1); integrin binding sialoprotein (Ibsp); laminin B1 subunit 1 (Lamb1-1); troponin C, cardiac/slow skeletal (Tnnc1); titin (Ttn); ADAM-like, decysin 1 (Adamdec1); and calcium/calmodulin-dependent protein kinase II, delta (Camk2d); while downregulating one or more of 27 genes selected from acireductone dioxygenase 1 (Adl1); keratinocyte differentiation associated protein (Krtdap); major urinary protein 1 (Mup1); cytochrome P450, family 2, subfamily j, polypeptide 6 (Cyp2j6); hydroxy-delta-5-steroid dehydrogenase, 3 beta- and steroid delta-isomerase 1 (Hsd3b1); G2/M-phase specific E3 ubiquitin ligase (G2e3); C130009A20R RIKEN cDNA C130009A20 gene; keratocan (Keral); growth arrest specific 5 (Gas5); cytochrome P450, family 11, subfamily b, polypeptide 1 (Cyp11b1); coagulation factor XIII, A1 subunit (F13a1); purinergic receptor P2Y, G-protein coupled, 14 (P2ry14); peroxisome proliferative activated receptor, gamma, coactivator 1 alpha (PGC1α); Gm2785, Ifi203 Mnda predicted gene 2785; Mnda interferon activated gene 205 (Ifi205), Mnda; interferon activated gene 203 (Ifi203); vitronectin (Vtn); interferon, alpha-inducible protein 27 like 2A (Ifi2712a); ATPase, Na+/K+ transporting, alpha 2 polypeptide (Atp1a2); apolipoprotein A-II (Apoa2); apolipoprotein H (Apoh); sulfotransferase family 1A, phenol-preferring, member 1 (Sult1a1); and flavin containing monooxygenase 2 (Fmo2) in said cell.

BRIEF DESCRIPTION OF THE DRAWINGS

FIG. 2 shows (A) real time quantitative PCR analysis to confirm the absence of Fst gene in Fst KO mouse embryonic fibroblast (MEF) primary culture; (B) western blot analysis showing the down-regulation of key BAT differentiation markers in Fst KO cultures undergoing adipogenic differentiation for 5 days; and (C) quantitative densitometric analysis.

DETAILED DESCRIPTION OF EMBODIMENTS OF THE INVENTION

I. Definitions

Figure 1:
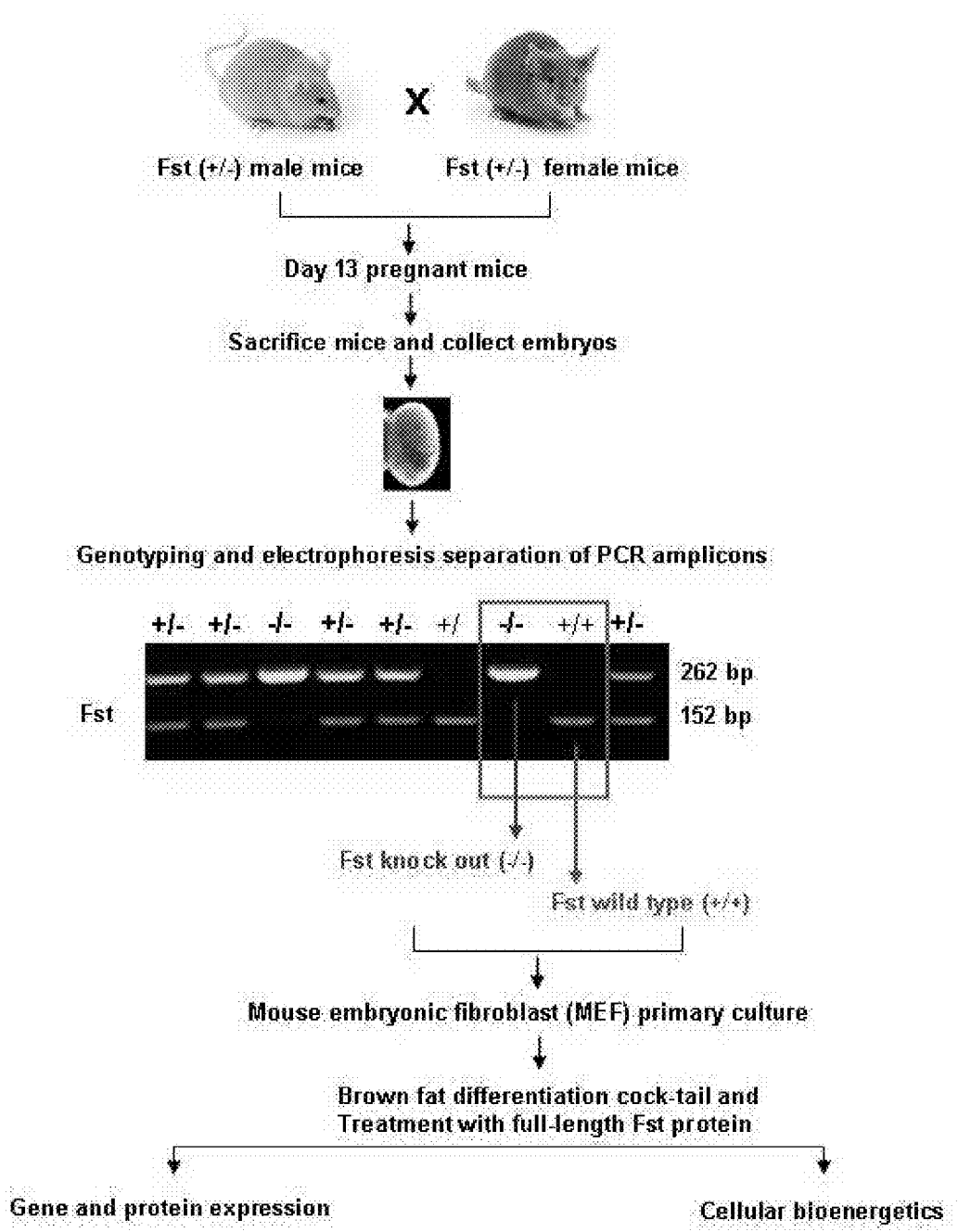
FIG. 1 illustrates the genetic approach taken for the isolation of Fst KO and WT embryos, culture of mouse embryonic fibroblasts (MEFs) and their differentiation.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted. Before the present methods, kits and uses therefore are described, it is to be understood that this invention is not limited to the particular methodology, protocols, cell lines, animal species or genera, constructs, and reagents described as such may, of course, vary. It is also to be understood that the terminology used herein is for the purpose of describing particular embodiments only, and is not intended to limit the scope of the present invention which will be limited only by the appended claims.

Throughout this specification and claims, the word "comprise," or variations such as "comprises" or "comprising," will be understood to imply the inclusion of a stated integer or group of integers but not the exclusion of any other integer or group of integers.

Terms and acronyms used herein are given their commonly accepted meanings. Thus, for example, DNA means deoxyribonucleic acid, and RNA means ribonucleic acid.

As used herein, "WT" means wild-type.

As used herein, "KO" means knock-out and refers to an animal or animals' cells in which a gene has been deleted, disrupted, or otherwise inactivated.

As used herein, "BAT" means brown adipose tissue.

As used herein, "MEF" means mouse embryonic fibroblast.

As used herein, "PVDF" means polyvinylidene difluoride.

As used herein, "PGC1-α" means peroxisome proliferator-activated receptor gamma, coactivator 1 alpha.

As used herein, "PGC1-β" means peroxisome proliferator-activated receptor gamma, coactivator 1 beta.

As used herein, "AP2" means adipocyte fatty acid binding protein 2

As used herein, "CEBPα" means CCAAT-enhancer binding protein-alpha

As used herein, "PPARγ" means peroxisome proliferator-activated receptor gamma

As used herein, "PRDM16" means PR domain containing 16

As used herein, "UCP-1" and "UCP1" refer to uncoupling protein-1

As used herein, "FST," "Fst," and "fst" refer to follistatin. "uncoupling protein 1 (UCP-1) or UCP1"

As used herein, "GAPDH" means glyceraldehyde 3 phosphate dehydrogenase

As used herein, "HRP" means horseradish peroxidase

As used herein, "ECL" means enhanced chemiluminiscence

The term "primer" refers to a single stranded polynucleotide that is capable of hybridizing to a nucleic acid and allowing the polymerization of a complementary nucleic acid, generally by providing a free 3'-OH group.

As used herein, the term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

The term "array" or "microarray" refers to an ordered arrangement of hybridizable array elements, preferably polynucleotide probes (e.g., oligonucleotides), on a substrate. The substrate can be a solid substrate, such as a glass slide, or a semi-solid substrate, such as nitrocellulose membrane.

The term "amplification" refers to the process of producing one or more copies of a reference nucleic acid sequence or its complement. Amplification may be linear or exponential (e.g., the polymerase chain reaction (PCR)). A "copy" does not necessarily mean perfect sequence complementarity or identity relative to the template sequence. For example, copies can include nucleotide analogs such as deoxyinosine, intentional sequence alterations (such as sequence alterations introduced through a primer comprising a sequence that is hybridizable, but not fully complementary, to the template), and/or sequence errors that occur during amplification.

The term "detection" includes any means of detecting, including direct and indirect detection.

The term "metabolic syndrome" or "metabolic syndrome related disorder" refer to or describe the physiological condition in mammals that is typically characterized by obesity, insulin resistance, hyperlipidemia, and hypertension. It may further encompass vascular abnormalities such as endothelial dysfunction, vascular pro-inflammatory condition, and vascular pro-coagulative conditions. Metabolic syndromes also refer to syndromes accompanied by health risk factors such as hypertriglyceridemia, hypertension, glycometabolism disorders, blood coagulation disorders and obesity. Metabolic Syndrome and Related Disorders may also include Insulin resistance, Central obesity, Glucose intolerance, Dyslipidemia with elevated triglycerides, Low HDL-cholesterol, Microalbuminuria, Predominance of small dense LDL-cholesterol particles, Hypertension, Endothelial dysfunction, Oxidative stress, Inflammation, and related disorders of polycystic ovarian syndrome, fatty liver disease (NASH), and gout. Metabolic disorders are a suspected precursor to a wide range of diseases, including type 2 diabetes, cardiovascular disease, stroke, cancer, polycystic ovary syndrome, gout, and asthma.

As used herein, "insulin resistance" refers to a phenomenon wherein, even though insulin is normally secreted in the body, "supply of glucose into cells" performed by insulin does not work properly. Therefore, glucose in the blood cannot enter cells, thus causing hyperglycemia, and further, cells themselves cannot perform normal functions thereof due to a shortage of glucose, leading to the manifestation of metabolic syndrome.

As used herein, a subject "at risk" of developing a metabolic syndrome related disorder may or may not have detectable disease or symptoms of disease, and may or may not have displayed detectable disease or symptoms of disease prior to the diagnostic methods described herein. "At risk" denotes that a subject has one or more risk factors, which are measurable parameters that correlate with development of cancer, as described herein and known in the art. A subject having one or more of these risk factors has a higher probability of developing a metabolic syndrome related disorder than a subject without one or more of these risk factor(s).

The term "diagnosis" is used herein to refer to the identification or classification of a molecular or pathological state, disease or condition, for example, a metabolic syndrome related disorder. "Diagnosis" may also refer to the classification of a particular sub-type of metabolic syndrome related disorder, e.g., by molecular features (e.g., a patient subpopulation characterized by differential expression or activity of certain biomarkers).

The term "prognosis" is used herein to refer to the prediction of the likelihood of developing a metabolic syndrome related disorder. The term "prediction" is used herein to refer to the likelihood that a patient will respond either favorably or unfavorably to a drug or set of drugs. In one embodiment, the prediction relates to the extent of those responses. In one embodiment, the prediction relates to whether and/or the probability that a patient will improve following treatment, for example treatment with a particular therapeutic agent, and for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, steroid treatment, etc., or whether long-term survival of the patient, following a therapeutic regimen is likely.

As used herein, "treatment" refers to clinical intervention in an attempt to alter the natural course of the individual or cell being treated, and can be performed before or during the course of clinical pathology. Desirable effects of treatment include preventing the occurrence or recurrence of a disease or a condition or symptom thereof, alleviating a condition or symptom of the disease, diminishing any direct or indirect pathological consequences of the disease, decreasing the rate of disease progression, ameliorating or palliating the disease state, and achieving improved prognosis. In some embodiments, methods and compositions of the invention are useful in attempts to delay development of a disease or disorder.

A "therapeutic agent", a "therapeutic agent effective to treat a metabolic syndrome related disorder", and grammatical variations thereof, as used herein, refer to an agent that when provided in an effective amount is known, clinically shown, or expected by clinicians to provide a therapeutic benefit in a subject who has a metabolic syndrome related disorder. In one embodiment, the phrase includes any agent that is marketed by a manufacturer, or otherwise used by licensed clinicians, as a clinically-accepted agent that when provided in an effective amount would be expected to provide a therapeutic effect in a subject who has a metabolic syndrome related disorder.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

An "effective amount" refers to an amount effective, at dosages and for periods of time necessary, to achieve the desired therapeutic or prophylactic result. A "therapeutically effective amount" of a therapeutic agent may vary according to factors such as the disease state, age, sex, and weight of the individual, and the ability of the antibody to elicit a desired response in the individual. A therapeutically effective amount is also one in which any toxic or detrimental effects of the therapeutic agent are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

An "individual," "subject" or "patient" is a vertebrate. In certain embodiments, the vertebrate is a mammal. Mammals include, but are not limited to, primates (including human and non-human primates) and rodents (e.g., mice and rats). In certain embodiments, a mammal is a human.

The term "sample", as used herein, refers to a composition that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized.

By "tissue or cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as serum, urine, sputum, or saliva. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like. A "reference sample", "reference cell", "reference tissue", "control sample", "control cell", or "control tissue", as used herein, refers to a sample, cell or tissue obtained from a source known, or believed, not to be afflicted with the disease or condition for which a method or composition of the invention is being used to identify. In one embodiment, a reference sample, reference cell, reference tissue, control sample, control cell, or control tissue is obtained from a healthy part of the body of the same subject or patient in whom a disease or condition is being identified using a composition or method of the invention. In one embodiment, a reference sample, reference cell, reference tissue, control sample, control cell, or control tissue is obtained from a healthy part of the body of an individual who is not the subject or patient in whom a disease or condition is being identified using a composition or method of the invention.

By "correlate" or "correlating" is meant comparing, in any way, the performance and/or results of a first analysis or protocol with the performance and/or results of a second analysis or protocol. For example, one may use the results of a first analysis or protocol in carrying out a second protocol and/or one may use the results of a first analysis or protocol to determine whether a second analysis or protocol should be performed. With respect to the embodiment of gene expression analysis or protocol, one may use the results of the gene expression analysis or protocol to determine whether a specific therapeutic regimen should be performed.

For purposes of the present invention, the terms "administer," "administering," and "administration" in reference to a composition, compound or drug mean taking, placing, putting, etc., the composition, compound or drug into the body of an individual by any method and by any route of administration. Such "administering" or "administration" may be performed by the individual, a health care provider or any other person.

As used herein, the term "EC50" refers to the concentration (measured in molarity) of a given preparation required to elicit a half-maximal response in a particular enzymatic assay.

The term "anti-diabetic agent" shall mean any drug that is useful in treating, preventing, or otherwise reducing the severity of any glucose metabolism disorder, or any complications thereof, including any of the conditions, disease, or complications described herein. Anti-diabetic agents include insulin, thiazolidinediones, sulfonylureas, benzoic acid derivatives, alpha-glucosidase inhibitors, or the like.

The terms "anti-glycemic activity" and "anti-glycemic agent" refer to an activity or agent that reduces blood glucose level, while the terms "anti-diabetic activity" and "anti-diabetic agent" refer to an activity or agent that treats diabetes mellitus by lowering glucose levels in the blood.

The term "anti-obesity agent" as used herein includes, but is not limited to, any currently known weight loss agent or drug. See Remington's Pharmaceutical Sciences, $16^{th}$ Ed., Arthur Osol (Editor), Mack Publishing Co., Easton, Pa. (1980) and each and every subsequent edition to date thereof. See also The Merck Index, $12^{th}$ Edition, S. Budavari (Editor), Merck & Co., Inc., Whitehouse Station, N.J. (1996) and each and every subsequent edition to date thereof.

As used herein, the term "anti-hypertensive agent" refers to any compound that when administered to a subject reduces blood pressure. In medicine, anti-hypertensive drugs are used to treat hypertension. There are several classes of anti-hypertensive drugs, including diuretics, adrenergic receptor antagonists, adrenergic receptor agonists, calcium channel blockers, ACE inhibitors, angiotensin II receptor antagonists, aldosterone antagonists, vasodilators, and renin inhibitors. Each of these groups of anti-hypertensive drugs acts to reduce blood pressure through a different mechanism.

As used herein, the terms "lipid-lowering agent" or "anti-lipidemic agent" refer to a pharmaceutical agent provided to a individual to achieve a lowering of lipids in the individual. For example, in certain embodiments, a lipid-lowering agent is provided to an individual to reduce one or more of ApoB, LDL-C, total cholesterol, and triglycerides.

The terms "cholesterol-lowering agent" and "cholesterol-lowering drug" as used herein refer to a pharmacologically active, pharmaceutically acceptable agent that, when administered to a human subject who has hypercholesterolemia, has the effect of beneficially modifying serum cholesterol levels. More particularly, the cholesterol-lowering agent lowers serum low density lipoprotein (LDL) cholesterol levels, or inhibits oxidation of LDL cholesterol, whereas high density lipoprotein (HDL) serum cholesterol levels may be lowered, remain the same, or be increased. Preferably, the cholesterol-lowering agent brings the serum levels of LDL cholesterol and HDL cholesterol (and, more preferably, triglyceride levels) to normal or nearly normal levels. "substantially inhibit"

The term "agent" refers to an active agent, drug, compound, composition of matter or mixture thereof which provides some pharmacologic, often beneficial, effect. This includes foods, food supplements, nutrients, drugs, vitamins, and other beneficial agents. As used herein, the terms further include any physiologically or pharmacologically active substance that produces a localized or systemic effect in a patient. The active drug that can be delivered includes antibiotics, antiviral agents, anepileptics, analgesics, antiasthmatics, anti-inflammatory agents and bronchodilators, and may be inorganic and organic compounds.

The terms "modulation," "modulating the activity," modulates" or "modulating compound", as used herein, means a positive or negative regulatory effect on the expression of a gene or activity of a protein.

As used herein the term "expression" or "expression of genetic message" means the conversion of genetic information encoded in a gene into mRNA, transfer RNA (tRNA) or ribosomal RNA (rRNA) through transcription. As used herein, the term "upregulate" means a positive regulatory effect on the expression of a gene. The term "downregulate" means a negative regulatory effect on the expression of a gene.

The terms "activator" or "activating compound" refer to a compound that increases the level of a specific protein and/or increases at least one activity of a that protein. In an exemplary embodiment, a follistatin activator may increase at least one biological activity of a follistatin protein by at least about 10%, 25%, 50%, 75%, 100%, or more.

Reference to "about" a value or parameter herein includes (and describes) embodiments that are directed to that value or parameter per se. For example, description referring to "about X" includes description of "X."

For use in the applications described or suggested herein, kits or articles of manufacture are provided which may comprise a carrier means being compartmentalized to receive in close confinement one or more container means such as vials, tubes, and the like, each of the container means comprising one of the separate elements to be used in the method. In one embodiment, one of the container means may comprise a probe that is or can be detectably labeled and utilizes nucleic acid hybridization to detect a target nucleic acid. The kit may also have containers containing nucleotide(s) for amplification of the target nucleic acid sequence and/or a container comprising a reporter means, such as a biotin-binding protein, such as avidin or streptavidin, bound to a reporter molecule, such as an enzymatic, florescent, or radioisotope label.

In other embodiments, the kit may comprise a labeled agent capable of detecting a polypeptide. Such agent may be an antibody which binds the polypeptide. Such agent may be a peptide which binds the polypeptide. The kit may comprise, for example, a first antibody (e.g., attached to a solid support) which binds to a polypeptide comprising a genetic variant as disclosed herein; and, optionally, a second, different antibody which binds to either the polypeptide or the first antibody and is conjugated to a detectable label.

In a specific embodiment, the kits of the present invention comprise one or more Fst or UCP-1 detecting agents. In another embodiment, the kit further comprises a therapeutic agent.

The term "package insert" is used to refer to instructions customarily included in commercial packages of therapeutic products, that contain information about the indications, usage, dosage, administration, combination therapy, contraindications and/or warnings concerning the use of such therapeutic products.

The term "prevention" refers to stopping or delaying of symptoms of disease onset, when the drug is used in the subject exhibiting no symptoms of disease onset but having high risk of disease onset.

As used herein, "nationally approved drugs" refers to a drug, compound, agent or preparation that has been validated for a therapeutic use by a ruling authority of a government. In the United States, the ruling authority is the FDA and in the European Union, it is the European Medicines Agency (EMA) that evaluates medicinal products.

The term "high fat food" refers generally to a food comprising at least 20 g of fat, or at least 25, 30, 35, 40, 45, or 50 g of fat, and/or at least about 45% or 50% fat. One FDA Guidance defines a "high-fat meal" as approximately 50% of total caloric content of the meal, whereas a "high-calorie meal" is approximately 800 to 1000 calories.

The term "food craving" refers to an intense and prolonged desire or yearning for food frequently in response to environmental cues. A priming dose of a food substance can trigger relapse in mammals whose food-seeking behavior previously had been extinguished II. Compositions and Methods In the present application, the role of Fst during BAT differentiation, energy metabolism and diet-induced obesity is demonstrated using both in vitro and in vivo models. We report here that Fst is a novel inducer of BAT differentiation and BAT mass. Since Fst KO mice are not viable (Matzuk et al. Nature. 1995; 374(6520):360-3), we isolated primary MEF cultures from both Fst KO and WT embryos and allowed them to differentiate under BAT-specific conditions. Our data provides a clear evidence that Fst loss of function is associated with a significant down-regulation of UCP1, PRDM16, PGC-1α and several markers implicated in BAT differentiation as well as energy and lipid metabolism. On the other hand, our in vivo data obtained from Fst-transgenic (Fst-Tg) mice suggest increased expression of these BAT-specific proteins in muscle as well as in both WAT and BAT tissues compared to their expression in similar tissues obtained from WT mice. Fst-Tg mice are resistant to diet-induced increase in body weight and fat mass as well as increase in triglyceride (TG) and free-fatty acids (FFA) levels. Furthermore, glucose clearance rates of these Fst-Tg mice were significantly higher compared to the age-matched WT mice. Thus, our data provide clear evidence regarding the novel role of Fst in BAT differentiation and lipid metabolism and supports a translational utility for therapeutic interventions in obesity and related metabolic disorders. Accordingly, we propose a novel induced follistatin assay for the identification of natural and non-natural compounds capable of increasing follistatin expression and thereby promoting brown fat differentiation as well as thermogenesis via UCP-1.

Exemplary Follistatin-Modulating Compounds and Methods of Use

The following examples show that potential modulators of follistatins such as resveratrol, butein, fisetin, piceatannol, quercetin and 3,5-dihydroxy-4-'-thiomethyl-trans-stilbene stimulates fat metabolism by reducing fat accumulation as well as inhibit adipogenesis; that FST and UCP-1 are necessary for resveratrol mediated fat mobilization; that resveratrol stimulates UCP-1 and ACC phosphorylation; that resveratrol boosts insulin sensitivity of adipocytes and that resveratrol, like other UCP-1 activators, can stimulate fatty acid oxidation in lipogenic cells.

Follistatin-modulating compounds may include for example, resveratrol (3,5,4'-Trihydroxy-trans-stilbene, butein (3,4,2',4' Tetrahydroxychalcone), progesterone, epithelial Gli2, adeno-associated virus serotype 1 vector, AAV1-FS344, induced transgene (See Kota, et al., Sci Transl. Med, 2009) guaifenesin dinitrate (GDN) (Wang, et al., Mol. Pharmaceuticals, 2009), and similar nitric oxide donors, deacetylase inhibitors, HDAC inhibitor trichostatin A.

3,5,4'-Trihydroxy-trans-stilbene (resveratrol), butein (3,4,2'4'-Tetrahydroxychalcone), piceatannol (3,5,3',4'-Tetrahydroxy-trans-stilbene), isoliquiritigenin (4,2',4'-Trihydroxychalcone), a flavonoid with chalcone structure, fisetin (3,7,3',4'-Tetrahydroxyflavone), which interacts with D-type G1 cyclins, quercetin (3,5,7,3'4'-Pentahydroxyflavone) (e.g., vitamin P and vitamin C2), Deoxyrhaponticin (3,5-Dihydroxy-4'-methoxystilbene 3-O-β-D-glucoside) a rhubarb extract which can inhibit glucose uptake; trans-Stilbene, which can inhibit or enhance the TPA-induced up-regulation of activator-1 protein; Rhapontin (3,3',5,3-Trihydroxy-4'-methoxystilbene, (see Anticancer Research 26: 3541-3546 (2006), cyaniding 3-O-β-D-glucoside), isolated from the skin of red grapes; cis-Stilbene, which can be employed in a reporter assay; Dehydroabietic acid (DAA) a food-derived terpenoid with various bioactivities; 5,7,3',4'-Tetrahydroxyflavone, Inhibits LPS-induced TNF-α, IL-6 and inducible nitric oxide production and blocks NF-κB and AP-1 activation; 4'-Hydroxyflavone, alters distribution of cholesterol among lipoproteins; 5,7-Dihydroxyflavone, chrysin (an aromatase inhibitor; chrysin-treated rats were considerably fatter than the controls); Morin (3,5,7,2',4'-Pentahydroxyflavone), inhibits P-gp-mediated cellular efflux of P-gp-substrate and could modulate the activity of metabolic enzyme, including cytochrome P450-3A4 (CYP3A4); Flavone, an anti-obesity compound; 5-Hydroxyflavone, an inhibitor; (−)-Epicatechin, a promoter of insulinogenesis, (Hydroxy Sites: 3,5,7,3',4'); (−)-Catechin (Hydroxy Sites: 3,5,7,3',4'), an insulinogenesis promoter; (−)-Gallocatechin (Hydroxy Sites: 3,5,7,3',4',5'), significantly decreases BMI; (+)-Catechin (Hydroxy Sites: 3,5,7,3',4'), decreases body fat and BMI; 5,7,3',4',5'-pentahydroxyflavone, an anti-glycation compound; Luteolin (5,7,3',4'-Tetrahydroxyflavone), enhances insulin sensitivity via activation of PPAR; transcriptional activity in adipocytes; 7,3',4',5'-Tetrahydroxyflavone; Kaempferol (3,5,7,4'-Tetrahydroxyflavone), improves glucose uptake of 3T3-L1 cells without adipogenesis activity; 6-Hydroxyapigenin (5,6,7,4'-Tetrahydoxyflavone) (Scutellarein), derived from flower petals [C. tinctorious]; Apigenin (5,7,4'-Trihydroxyflavone), enhances the expression of TGF-beta; 3,6,2',4'-Tetrahydroxyflavone, a soybean metabolite; 7,4'-Dihydroxyflavone bayin which suppresses eotaxin secretion; Daidzein (7,4'-Dihydroxyisoflavone), daidzein, a soybean isoflavone; Genistein (5,7,4'-Trihydroxyflavanone), narirutin a flavone derived from oranges; Naringenin (5,7,4'-Trihydroxyflavanone), an orange juice antioxidant; 3,5,7,3',4'-Pentahydroxyflavanone; Flavanone; Pelargonidin chloride (3,5,7,4'-Tetrahydroxyflavylium chloride), an anti-carcinogen; Hinokitiol (b-Thujaplicin; 2-hydroxy-4-isopropyl-2,4,6-cycloheptatrien-1-one), a natural tropolone, an anti-oxidant; L-(+)-Ergothioneine ((S)-a-Carboxy-2,3-dihydro-N,N,N-trimethyl-2-thioxo-1H-imidazole-4-ethanaminium inner salt), a physiologic cytoprotectant; Caffeic Acid Phenyl Ester; MCI-186 (3-Methyl-1-phenyl-2-pyrazolin-5-one), an aldose derivative; HBED (N,N'-Di-(2-hydroxybenzyl)ethylenediamine-N,N'-diacetic acid*H20), an iron chelator and anti-oxidant; Ambroxol (trans-4-(2-Amino-3,5-dibromobenzylamino)cyclohexane-HCl, an anti-poptotic agent; and U-83836E ((−)-2-((4-(2,6-di-1-Pyrrolidinyl-4-pyrimidinyl)-1-piperzainyl)methyl)-3,4-dihydro-2,5,7,8-tetramethyl-2H-1-benzopyran-6-ol-2HCl), an antioxidant which inhibits iron-dependent lipid peroxidation, and additional compounds that are available, or become available, utilized individually or in conjunction with one another. Analogs and derivatives thereof can also be used.

Follistatin-modulating compounds may include for example, histone deacetylase (HDAC) inhibitors, such as Hydroxamic acids (or hydroxamates), Trichostatin A (TSA), Phenyl butyrate and Valproic Acid, Cyclic tetrapeptides (trapoxin B) and depsipeptides, Vironostat (SAHA), Belinostat, LAQ824, Panobinostat (LBH589), Benzamides, Entinostat (MS-2750), Mocetinostat (MGCD0103), Abexinostat (PC1-24781), Resminostat (4SC-201), Givinostat (ITF2357), Quisinostat (JNJ-26481585).

Follistatin-modulating compounds may include for example, nitric oxide (NO) donors, such as the following Diazeniumdiolate (NONOate) class, S-nitrosothiols class and the NO donor hybrid drugs containing a nitro-oxy moiety. Examples of the Diazeniumdiolate (NONOate) class of NO donor drugs include:

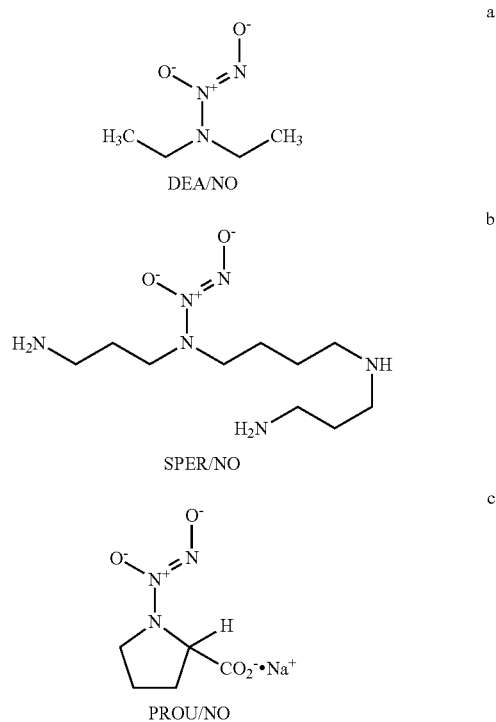

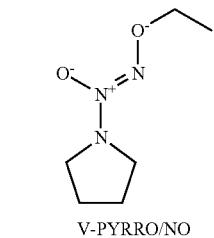

V-PYRRO/NO

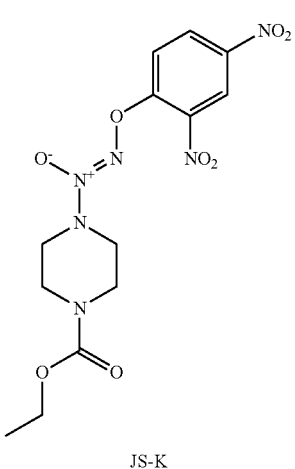

JS-K

Examples of the S-nitrosothiols class of NO donors include:

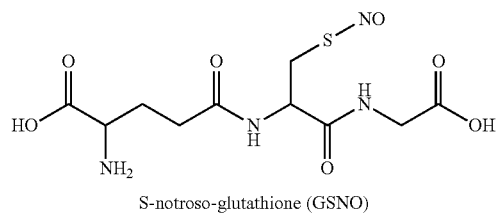

S-notroso-glutathione (GSNO)

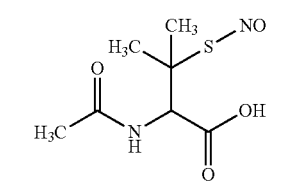

S-nitroso-N-acetylpenicillamine (SNAP)

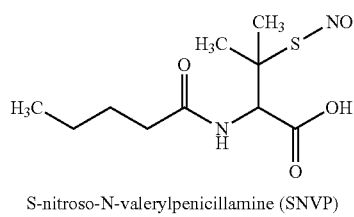

S-nitroso-N-valerylpenicillamine (SNVP)

Examples of the NO donor hybrid drugs containing a nitro-oxy moiety include:

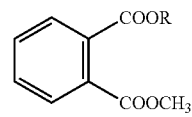

R = H
Aspirin

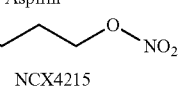

NCX4215

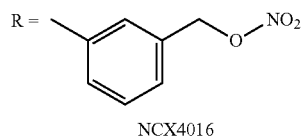

NCX4016

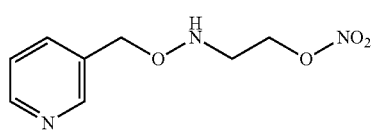

nicorandil

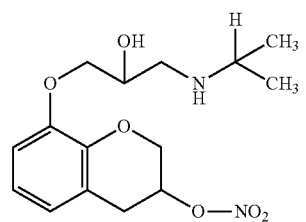

Nipradilol (K-351)

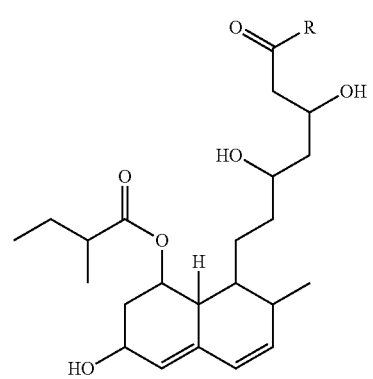

R = OH
pravastatin

R = O(CH$_2$)$_4$ONO$_2$
nitro-pravastatin

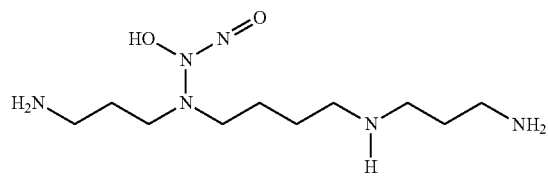

Spermin NONOate

-continued

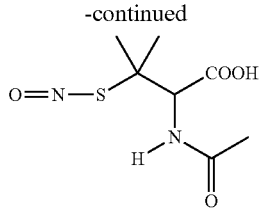

S-Nitroso-N-Acetyl-D,
L-Penicillamine (SNAP)

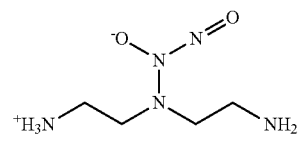

Diethylenetriamine NONOate
(DETA NONOate)

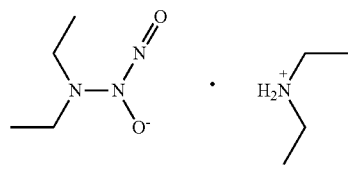

DEA/NO; Diethylamine NONOate

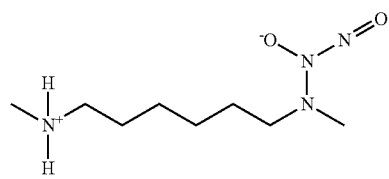

Methylamine hexamethylene methylamine
NONOate (MAHMA NONOate)

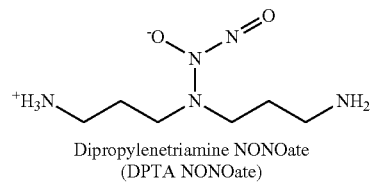

Dipropylenetriamine NONOate
(DPTA NONOate)

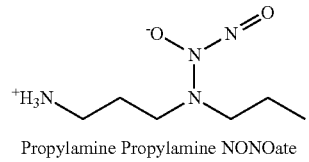

Propylamine Propylamine NONOate
(PAPA NONOate)

9-Nitrooleate

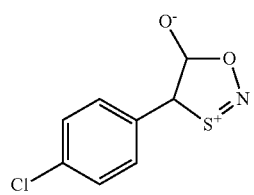

4-(p-chlorophenyl)-1,3,2-
Oxathiazolylium-5-olate

-continued

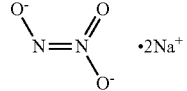

Angeli's salt

Follistatin-modulating compounds may include for example, Androgenic hormones such as:

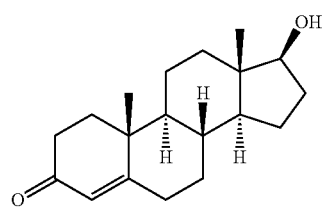

Testosterone

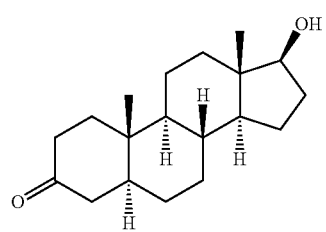

DHT

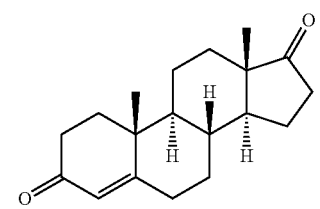

Androstenedione

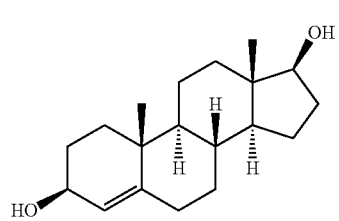

4-Androstenediol

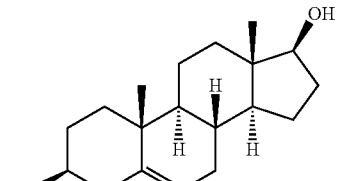

5-Androstenediol

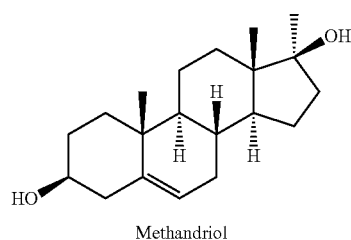

Methandriol

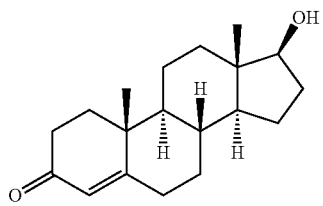

Tetrahydrogestrinone

Follistatin-modulating compounds may also include for example, Anabolic Steroids such as Anadrol, Anavar, Clenbuterol, Clomid, Cytomel, Deca Durabolin, Dianabol, Equipoise, Halotestin, Human Growth Hormone, Insulin, Lasix, Methyltestosterone, Nolvadex, Omnadren, Primobolan, Sustanon, Trenbolone, and Winstrol.

Follistatin-modulating compounds may also include for example, Selective androgen receptor modulators (SARMS) which include Hypermyoanabolic and Myoanabolic SARMs, as well as Partially Myoanabolic or CNS-Active SARMs. (Mohler et al., J. Med. Chem., 2009, 52 (12) pp 3597-3617)

I. Exemplary Hypermyoanabolic and Myoanabolic SARMs include:

| SARM |
|---|

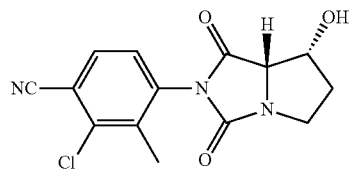

testosterone
(DHT if reduced)

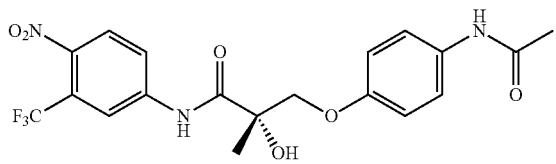 [SMILES: CC(=O)Nc1ccc(OC[C@](C)(O)C(=O)Nc2ccc([N+](=O)[O-])c(C(F)(F)F)c2)cc1]

propionamide
8 from GTx

| SARM |
|---|

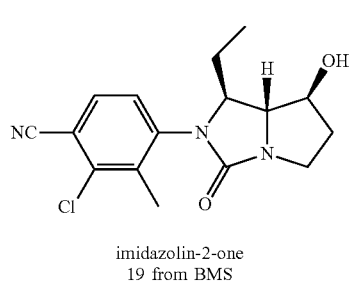

bicyclic hydantoin
18 from BMS

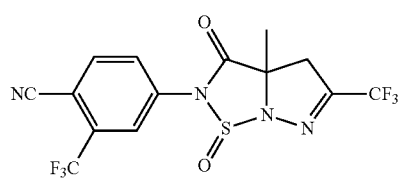

imidazolin-2-one
19 from BMS

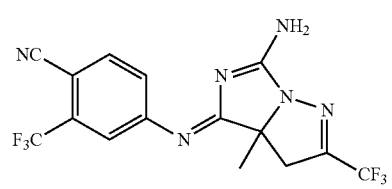 [SMILES: CC12CC(C(F)(F)F)=NN1C(N)=N/C2=N\c1ccc(C#N)c(C(F)(F)F)c1]

bicyclic thiohydantoin
S-21 from JNJ

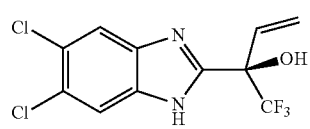 [SMILES: C=C[C@@](O)(c1nc2cc(Cl)c(Cl)cc2[nH]1)C(F)(F)F]

imidazolopyrazole
R-22 from JNJ

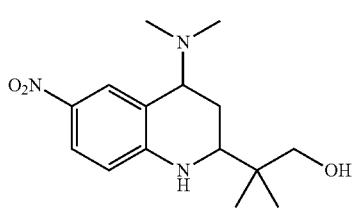 [SMILES: CN(C)C1CC(C(C)(C)CO)Nc2ccc([N+](=O)[O-])cc21]

benzimidazole
24 from JNJ tetrahydroquinoline
25 from Kaken

| SARM |
|---|
| 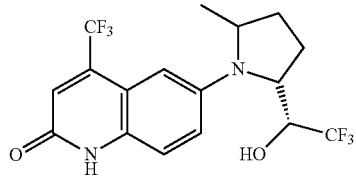 [SMILES: CC1CCC([C@@H](O)C(F)(F)F)N1c1ccc2[nH]c(=O)cc(C(F)(F)F)c2c1]
bicyclic quinolinone
26 from Ligand |
| 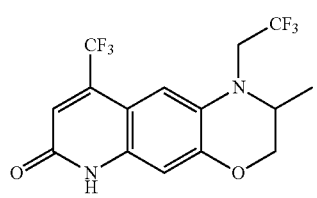 [SMILES: CC1COc2cc3[nH]c(=O)cc(C(F)(F)F)c3cc2N1CC(F)(F)F]
7H-oxazino quinolinone
11 from Ligand |
| 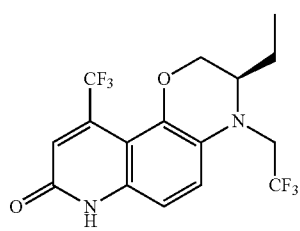 [SMILES: CC[C@@H]1COc2c(ccc3[nH]c(=O)cc(C(F)(F)F)c23)N1CC(F)(F)F]
8H-oxazino quinolinone
12 from Ligand |

II. Exemplary Partially Myoanabolic or CNS-Active SARMs include:

| SARM |
|---|
| Partial Efficacy SARMs |
| 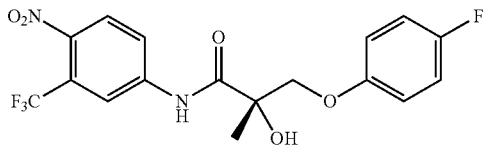 [SMILES: C[C@](O)(COc1ccc(F)cc1)C(=O)Nc1ccc([N+](=O)[O-])c(C(F)(F)F)c1]
propionamide
13 from GTx |
| 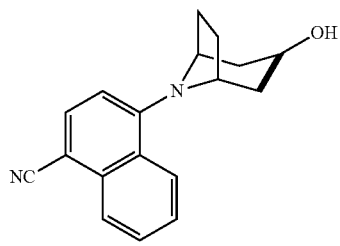
tricyclic aniline
17 from Acadia |

| SARM |
|---|
| 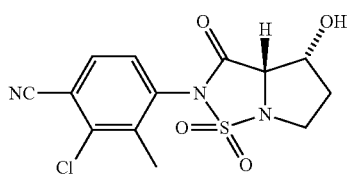 [SMILES: Cc1c(N2C(=O)[C@@H]3[C@H](O)CCN3S2(=O)=O)ccc(C#N)c1Cl]
pyrrolothiadiazolone
20 from BMS |
| 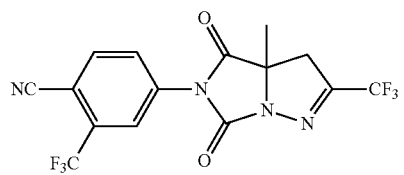
imidazopyrazole
S-23 from JNJ |
| CNS Active SARMs |
| 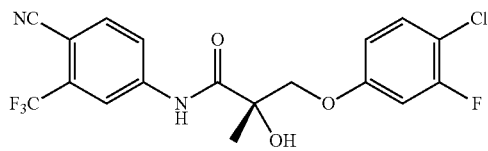 [SMILES: C[C@](O)(COc1ccc(Cl)c(F)c1)C(=O)Nc1ccc(C#N)c(C(F)(F)F)c1]
propionamide
14 from GTx |
| 
pyrazoline
16 from JNJ |
| 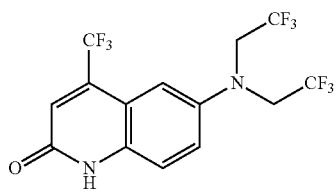 [SMILES: O=c1cc(C(F)(F)F)c2cc(N(CC(F)(F)F)CC(F)(F)F)ccc2[nH]1]
bicyclic quinolinone
15 from Ligand |

Additional selective androgen receptor modulators (SARMS) may include:

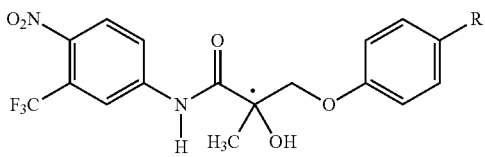

| Name | Isomer | R | Ki (nM) | Activation (% of 1 nM DHT |
|------|--------|---|---------|---------------------------|
| R-1 | R | F | 225 ± 15 | N.D. |
| S-1 | S | F | 6.1 ± 0.2 | 43 ± 2.6 |
| S-2 | S | COCH$_3$ | 37 ± 2.4 | 9.7 ± 1.5 |
| S-3 | S | COC$_2$H$_5$ | 6.1 ± 0.1 | 75 ± 11 |
| S-4 | S | NHCOCH$_3$ | 4.0 ± 0.7 | 93 ± 7.0 |

(Chen et al., J Pharmacol Exp Ther. 2005 February; 312(2):546-53.)

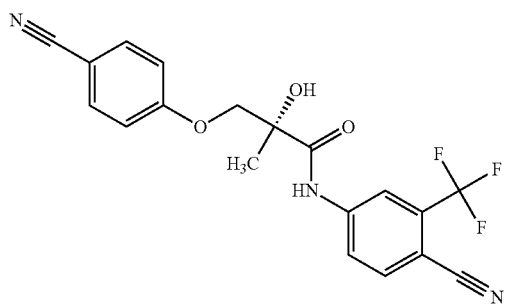

Enobosarm ((2S)-3-(4-cyanophenoxy)-N-[4-cyano-3-(trifluoromethyl)phenyl]-2-hydroxy-2-methylpropanamide) (also known as Ostarine, GTx-024 and MK-2866)

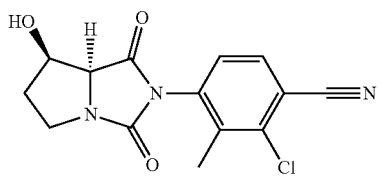

BMS-564,929 ((7R,7aS)-2-Chloro-4-(7-hydroxy-1,3-dioxotetrahydropyrrolo[1,2-c]imidazol-2-yl)-3-methylbenzonitrile)
LGD-4033

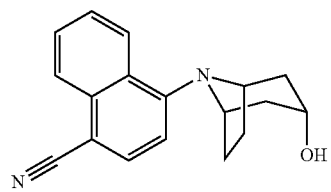

AC-262,356 (4-(3-Hydroxy-8-aza-bicyclo[3.2.1]octyl)-naphthalene-1-carbonitrile)

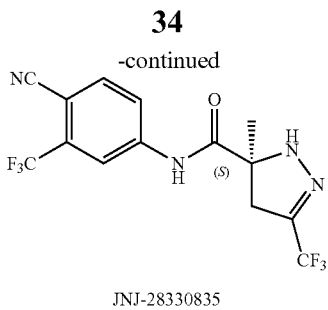

JNJ-28330835

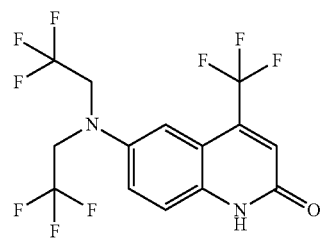

LGD-2226 (6-(bis-(2,2,2-trifluoroethyl)amino)-4-trifluoromethyl-1H-quinolin-2-one)

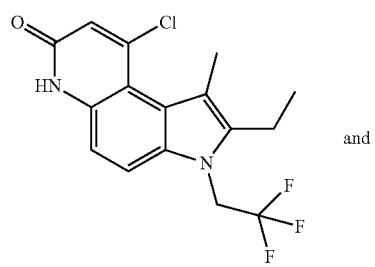

and

LGD-3303 (9-chloro-2-ethyl-1-methyl-3-(2,2,2-trifluoroethyl)-3H-pyrrolo[3,2-f]quinolin-7(6H)-one)

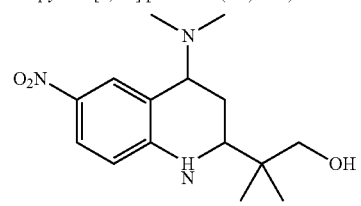

S-40503 (2-[4-(dimethylamino)-6-nitro-1,2,3,4-tetrahydroquinolin-2-yl]-2-methylpropan-1-ol)

Follistatin-modulating compounds may also include for example, plant based myostatin inhibitors such as:

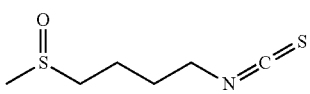

Supforaphanes (1-Isothiocyanato-4-methylsulfinylbutane)

Follistatin-modulating compounds may also include for example, PPAR-delta agonists such as:

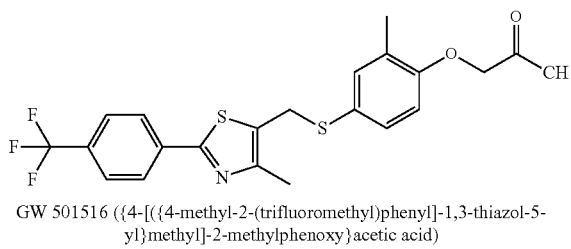 [SMILES: CC(=O)COc1ccc(SCc2sc(-c3ccc(C(F)(F)F)cc3)nc2C)cc1C]

GW 501516 ({4-[({4-methyl-2-(trifluoromethyl)phenyl]-1,3-thiazol-5-yl}methyl]-2-methylphenoxy}acetic acid)

Follistatin-modulating compounds may also include for example, Myostatin blockers including myostatin-blocking antibodies, myostatin propeptide, follistatin and follistatin-related proteins, soluble myostatin receptors, small interfering RNA and small chemical inhibitors.

Follistatin-modulating compounds may also include for example, the mammalian target of rapamycin (mTOR), Insulin growth factor 1 and Crypto.

As represented herein, the follistatin modulating compounds according to the present invention are characterized by a variety of chemical structures. However, follistatin modulating compounds may be represented by families of compounds that share a core chemical structure common to the members of each family.

In one embodiment, a follistatin-modulating compound is a stilbene or chalcone compound. In an embodiment, a follistatin-modulating compound is flavanone compound. In an embodiment, a follistatin-modulating compound is an isoflavanone compound. In an embodiment, a follistatin-modulating compound is an anthocyanidin compound. Embodiments of methods for activating a follistatin protein family member may comprise contacting a cell with a stilbene, chalcone, or flavone compound.

In another embodiment, exemplary follistatin-modulating compounds are isonicotinamide analogs, (See U.S. Pat. Nos. 5,985,848; 6,066,722; 6,228,847; 6,492,347; 6,803,455; and U.S. Patent Publication Nos. 2001/0019823; 2002/0061898; 2002/0132783; 2003/0149261; 2003/0229033; 2003/0096830; 2004/0053944; 2004/0110772; and 2004/0181063, the disclosures of which are hereby incorporated by reference in their entirety). In an exemplary embodiment, follistatin-modulating compounds may be an isonicotinamide analog.

Also included are pharmaceutically acceptable addition salts and complexes of the follistatin-modulating compounds described herein. In cases wherein the compounds may have one or mere chiral centers, unless specified, the compounds contemplated herein may be a single stereoisomer or racemic mixtures of stereoisomers.

In cases in which the follistatin-modulating compounds have unsaturated carbon-carbon double bonds, both the cis and trans isomers are contemplated herein. In cases wherein the compounds may exist in tautomeric forms, such as keto-enol tautomers, each automeric form is contemplated as being included within the methods presented herein, whether existing in equilibrium or locked in one form by appropriate substitution with R'. The meaning of any substituent at any one occurrence is independent of its meaning, or any other substituent's meaning, at any other occurrence.

Prodrugs are considered to be any covalently bonded carriers that release the active parent drug in vivo.

Analogs and derivatives of the above-follistatin-modulating compounds described herein can also be used for activating a member of the follistatin protein family. For example, derivatives or analogs may make the compounds more stable or improve their ability to traverse cell-membranes or being phagocytosed or pinocytosed. Exemplary derivatives include glycosylated derivatives, as described, e.g., in U.S. Pat. No. 6,361,815 for resveratrol. Other derivatives of resveratrol include cis- and trans-resveratrol and conjugates thereof with a saccharide, such as to form a glucoside (see, e.g., U.S. Pat. No. 6,414,037). Glucoside polydatin, referred to as piceid or resveratrol 3-O-beta-D-glucopyranoside, can also be used. Saccharides to which compounds may be conjugated include glucose, galactose, maltose, lactose and sucrose. Glycosylated stilbenes are further described in Regev-Shoshani et al. Biochemical J. (published on Apr. 16, 2003 as BJ20030141). Other derivatives of compounds described herein are esters, amides and prodrugs. Esters of resveratrol are described, e.g., in U.S. Pat. No. 6,572,882. Resveratrol and derivatives thereof can be prepared as described in the art, e.g., in U.S. Pat. Nos. 6,414,037; 6,361,815; 6,270,780; 6,572,882; and Brandolini et al. (2002) J. Agric. Food. Chem. 50:7407. Derivatives of hydroxyflavones ate described, e.g., in U.S. Pat. No. 4,591,600. Resveratrol and other activating compounds can also be obtained commercially, e.g., from Sigma.

In certain embodiments, a certain biological function, e.g., reducing body weight is modulated by any one of a follistatin-modulating compound, of a genus of compounds, with the proviso that the genus does not include one or more specific compounds. For example, in certain embodiments, a follistatin activator-activating compound may be capable of decreasing the level of expression and or activity of a follistatin protein with the exception that the compound is not resveratrol, a flavone, or any other compound specifically cited herein or any other compound that has an activating effect on a follistatin protein, prior to the priority date of this application.

In certain embodiments, the subject FST activators do not have any substantial ability to activate FST orthologs in lower eukaryotes.

In certain embodiments, the follistatin activating compounds may have the ability to activate one or more follistatin protein homologs, such as follistatin-related proteins (Tortoriello, et al., Endocrinology, 2001).

In certain embodiments, FST modulators such as fibroblast growth factor-8 (FGF8) may be used to modulate fat mobilization (Alexandre, et al., Development, 2006). For example, FST activators may be used to induce fat mobilization and may be used to treat, e.g., obesity and insulin resistance disorders.

In an exemplary embodiment, follistatin-modulating compounds may be administered as a combination therapy. For example, for reducing weight, preventing weight gain, or treatment or prevention of obesity, one or more follistatin-modulating compounds may be used in combination with "anti-obesity agents".

Alternatively, one or more follistatin-modulating compounds may be used in combination with "anti-diabetic agents."

In certain embodiments, one or more follistatin-modulating compounds may be directed specifically to a certain tissue (e.g., liver) rather than the whole body (Gressner, et al., Frontiers in Bioscience, 2002). Tissue specific treatments may be used to treat, e.g., obesity and insulin resistance disorder.

In certain embodiments the methods are useful for preventing fat accumulation in cells with lipogenic capacity, e.g. liver, pancreas and muscle cells (Nakatani, et al., Endo, 2011).

Methods for reducing or preventing fat accumulation in a cell may also comprise increasing the protein level of FST in a human cell. Increasing protein levels can be achieved by introducing into a cell follistatin protein or one or more copies of a nucleic acid that encodes a follistatin (Tsuchida, EP1748069B1). The nucleic acid may be expressed under the control of a promoter that regulates the expression of the FST nucleic acid. Alternatively, the nucleic acid may be introduced into the cell at a location in the genome that is downstream of a promoter. Methods for increasing the level of a protein by using these methods are well known in the art.

A nucleic acid that is introduced into a cell to increase the protein level of a follistatin may encode a protein that is at least about 80%, 85%, 90%, 95%, 98%, or 99% identical to the sequence of a follistatin.

The nucleic acid may also be a nucleic acid that hybridizes, preferably under stringent O-hybridization conditions, to a nucleic acid encoding a wild-type follistatin.

Stringent hybridization conditions may include hybridization and a wash in 0.2×SSC at 65° C. When using a nucleic acid that encodes a protein that is different from a wild-type follistatin protein, such as a protein that is a fragment of a wild-type follistatin, the protein is preferably biologically active, e.g., is capable of deacetylation. It is only necessary to express in a cell a portion of the follistatin that is biologically active. For example, a protein that differs from wild-type FST, preferably contains the core structure thereof. Methods for increasing follistatin protein levels also include methods for stimulating the transcription of follistatin gene.

Whether in vitro or in vivo, a follistatin inhibitory compound may also be contacted with a cell or administered either alone or in combination with other therapeutic agents. In one embodiment, more than one follistatin inhibitory compound may be contacted with a cell or administered. For example, at least 2, 3, 5, or 10 different follistatin inhibitory compounds may be contacted with a cell or administered. In another embodiment, a follistatin inhibitory compound may be administered as part of a combination therapy with another therapeutic agent. Such combination therapies may be administered simultaneously (e.g., more than, one therapeutic agent administered at the same time) or sequentially with e.g., different compounds or therapeutic agents administered at different times during a treatment regimen.

In another embodiment, one or more follistatin inhibitory compounds may be directed specifically to a certain tissue (e.g., liver) rather than the whole body. Tissue specific treatments may be used to treat, e.g., hyperglycemia.

Methods for stimulating fat accumulation in a cell may also comprise decreasing the protein level of a follistatin in the cell.

A follistatin activating compound may traverse the cytoplasmic membrane of a cell. For example, a compound may have a cell-permeability of at least about 20%, 50%, 75%, 80%, 90% or 95%.

Compounds described herein may display one or a number of the following characteristics: the compound may be essentially non-toxic to a cell or subject; the compound may be an organic molecule or a small molecule less than or equal to 2000 amu, less than or equal to 1000 amu; a compound may have a half-life under normal atmospheric conditions of at least about 30 days, 60 days, 120 days, 6 months or 1 year; the compound may have a half-life in solution of at least about 30 days, 60 days, 120 days, 6 months or 1 year; a compound may be more stable in solution than resveratrol by at least a factor of about 50%, 2 fold, 5 fold, 10 fold, 30 fold, 50 fold or 100 fold; a compound may promote deacetylation of the DNA repair factor Ku70; a compound may promote deacetylation of RelA/p65; a compound may increase general turnover rates and enhance the sensitivity of cells to TNF-induced apoptosis.

Knockout mice may be generated, for example, by methods such as those described in Wakil, et al., U.S. Pat. No. 6,548,738, hereby incorporated by reference. Such methods, in general, may include design of a forward primer and a reverse primer, and use of such primers to amplify nucleic acid molecules, such as, for example, cDNAs. The cDNA may be sequenced, and used to provide a vector, and the vector may be used to generate cells, such as KO cells, preferably KO embryonic stem (ES) cells. ES cell clones may be injected into mouse blastocysts, and the injected blastocysts implanted into female animals (e.g., into the uterine horns of pseudopregnant female mice), in order to provide transgenic (e.g., KO) mice embryos and pups, if the embryos survive until birth.

Methods for treating or preventing insulin resistance, hypercholesterolemia; obesity; high triglyceride (TG) or low high-density lipoprotein cholesterol (HDL-C); diabetes; and hypertension may also comprise inhibiting branched chain amino acids (BCAAs) and induction of omega-3 polyunsaturated fatty acids (PUFAs), that include EPA, DPA and DHA, in muscle and adipose tissues. Recent studies demonstrating strong associations of BCAA and related metabolites with disease, disease progression, and intervention outcomes suggest a possible cause/effect relationship between these metabolites and disease development (Wurtz et al., Diabetes Care 36:648-655, 2013; Newguard, Cell Metabolism, Volume 15, Issue 5, 606-614, 2 May 2012). Moreover, the large body of extant literature implicating fatty acids and other lipids in development of tissue dysfunction and metabolic disease raises the possibility that these abnormalities might be driven by combined effects of lipids and BCAA. (Wurtz et al., Diabetes Care 36:648-655, 2013; Newguard, Cell Metabolism, Volume 15, Issue 5, 606-614, 2 May 2012; Saito et al., Atherosclerosis 200 (2008) 135-140)

Additional Exemplary Methods

Methods for treating or preventing obesity or weight gain, in a subject, such as to reduce the subject's weight or to diminish weight gain. A method may comprise administering a pharmaceutically effective amount of an agent that increases the activity or protein level of a follistatin. Likely subjects are obese, or becoming obese. The subject would have a propensity to gain excess weight, due to family history predicting that outcome. Exemplary agents are those described herein, Treatment may encompass administering combination of agents. Monitoring part of the method may include monitoring the subject's weight and/or follistatin activation, for example, in adipose tissue.

Methods for treating or preventing a metabolic disorder, insulin-resistance or other precursor symptoms of type II diabetes or complications thereof comprise an embodiment of this invention. Administering treatment according to methods herein recited may increase insulin sensitivity or decrease insulin levels in a subject. A method may comprise administering a pharmaceutically effective amount of an agent to a subject that increases the activity or protein level of follistatin, such as FST. A subject who has insulin resistance or other precursor symptom of type II diabetes, who has type II diabetes, or who is likely to develop any of these conditions would benefit from such treatment. For example, the subject may be a subject having insulin resistance, e.g., having high circulating levels of insulin and/or associated conditions, such as hyperlipidemia, dyspogenesis, hypercholesterolemia, impaired glucose tolerance, high blood glucose sugar level, and other manifestations of syndrome X, hypertension, atherosclerosis and lipodystrophy. Exemplary agents are those described herein. In a further aspect, the invention relates to compositions and formulations for improving ovulatory function (and thus fertility) in a female in need of such improvement, regularizing her menstrual cycle, and reducing hirsutism, Such activity represents organismal responses that may be assayed as a means of identifying compounds, drugs, and medicinal formulations suitable for preventing or treating Centers for Disease Control and Prevention (CDCP), diseases related to CDCP, and/or chemotherapeutic resistance. Likewise, these organismal responses may be assayed to measure the efficacy of such compounds, drugs, and medicinal formulations.

In a further aspect, the invention relates to compositions and formulations for lowering levels of circulating carbohydrate, preventing or treating age-related obesity, preventing or treating diet-related obesity, and preventing or treating steatosis. Such activity represents organismal responses that may be assayed as a means of identifying compounds, drugs, and medicinal formulations suitable for preventing or treating metabolic syndrome, diseases related to metabolic syndrome, and/or chemotherapeutic resistance. Likewise, these organismal responses may be assayed to measure the efficacy of such compounds, drugs, and medicinal formulations.

In a further aspect, the invention relates to compositions and formulations for preventing or treating chronic hyperglycemia, and preventing or treating diet-induced diabetes. Such activity represents organismal responses that may be assayed as a means of identifying compounds, drugs, and medicinal formulations suitable for preventing or treating metabolic syndrome diseases related to metabolic syndrome, and/or chemotherapeutic resistance. Likewise, these organismal responses may be assayed to measure the efficacy of such compounds, drugs, and medicinal formulations.

In a further aspect, the invention relates to compositions and formulations of follistatin-modulating compounds in combination or conjunction with nationally approved compounds or drugs belonging to the drug classes represented by Abilify (aripiprazole), ABREVA (docosanol), Accolate, Accretropin (somatropin rDNA Original), Aciphex (rabeprazole sodium), Actemra (tocilizumab), Actiq, Activella (Estradiol/Norethindrone Acetate) Tablets, Actonel, ACTOplus met (pioglitazone hydrochloride and metformin hydrochloride), ACTOS, Acular (ketorolac tromethamine ophthalmic solution) 0.5%, Acular (ketorolac tromethamine ophthalmic solution) 0.5%, Acuvail (ketorolac tromethamine), Acyclovir Capsules, Adcirca (tadalafil), Adderall (mixed salts of a single entity amphetamine), Adderall XR, Advicor (extended-release niacin/lovastatin), Afinitor (everolimus), Agenerase (amprenavir), Aggrenox, Agrylin (anagrelide HCL), Agrylin (anagrelide HCL), AK-Con-A (naphazoline ophthalmic), Akten (lidocaine hydrochloride), Alamast, Albenza (albendazole), Aldara (imiquimod), Aldurazyme (laronidase), Alesse (100 mcg levonorgestrel/20 mcg ethinyl estradiol tablets), Alimta (pemetrexed for injection), Alinia (nitazoxanide), Allegra (fexofenadine hydrochloride), Allegra-D, Alora, Aloxi (palonosetron), Alphagan (brimonidine), AlphaNine SD Coagulation Factor IX (Human), Alrex, Altabax (retapamulin), Altocor (lovastatin) Extended-Release Tablets, Alvesco (ciclesonide), Amaryl (Glimepiride), Amerge, Amevive (alefacept), Amitiza (lubiprostone), Amoxil (amoxicillin), Ampyra (dalfampridine), Amrix (cyclobenzaprine hydrochloride extended release), Androderm (Testosterone Transdermal System), AndroGel testosterone gel, AneuVysion Assay, Anexsia, Angiomax (bivalirudin), Antizol Injection, Anzemet, Anzemet, Aphthasol, Aplenzin (bupropion hydrobromide), Apokyn (apomorphine hydrochloride), Apthasol (Amlexanox), Aptivus (tipranavir), Aptivus (tipranavir), Arava, Aredia (pamidronate disodium for injection), Arestin (minocycline hydrochloride), Argatroban Injection, ARICEPT (donepezil hydrochloride), Arimidex (anastrozole), Arixtra, Aromasin Tablets, Arranon (nelarabine), Arthrotec, Arzerra (ofatumumab), Asacol (mesalamine), Astelin nasal spray, Astepro (azelastine hydrochloride nasal spray), Atacand (candesartan cilexetil), Atacand (candesartan cilexetil), Atacand (candesartan cilexetil), Atracurium Besylate Injection, Atridox, Atridox, Atrovent (ipratropium bromide), Atryn (antithrombin recombinant lyophilized powder for reconstitution), Augmentin (amoxicillin/clavulanate), Avandamet (rosiglitazone maleate and metformin HCl), Avandia (rosiglitazone maleate), Avastin (bevacizumab), Avastin (bevacizumab), Avelox I.V. (moxifloxacin hydrochloride), Avinza (morphine sulfate), Avita Gel, Avita Gel, Avonex (Interferon Beta 1-A), Axert (almotriptan malate) tablets, Axid AR (nizatidine, Axona (caprylidene), AzaSite (azithromycin), Azmacort (triamcinolone acetonide) Inhalation Aerosol, Azor (amlodipine besylate; olmesartan medoxomil), Azulfidine EN-tabs Tablets (sulfasalazine delayed release tablets, USP), Bactroban Cream, Bactroban Nasal 2% (mupirocin calcium ointment), Banzel (rufinamide), Baraclude (entecavir), Baycol (cerivastatin sodium), Bayer Extra Strength Asprin, BeneFIX (coagulation Factor IX (recombinant)), BeneFIX (coagulation Factor IX (recombinant)), Benicar, Benzamycin (erythromycin 3%-benzoyl peroxide 5% topical gel), Bepreve (bepotastine besilate ophthalmic solution), Berinert (C1 Esterase Inhibitor (Human)), Besivance (besifloxacin ophthalmic suspension), Betapace AF Tablet, Betaxon, Bextra, Bexxar, Biaxin XL (clarithromycin extended-release tablets), BiDil (isosorbide dinitrate/hydralazine hydrochloride), Boniva (ibandronate), Botox (onabotulinumtoxinA), Botox (onabotulinumtoxinA), Botox Cosmetic (botulinum toxin type A), Bravelle (urofollitropin for injection, purified), Breathe Right, Bromfenac, Brovana (arformoterol tartrate), BSS Sterile Irrigating Solution, Busulflex, Byetta (exenatide), Caduet (amlodipine/atorvastatin), Cafcit Injection, Cambia (diclofenac potassium for oral solution), Campath, Campostar, Campral (acamprosate calcium), Camptosar, Canasa (mesalamine), Cancidas, Captopril and hydrochlorotiazide, Captopril and hydrochlorotiazide, Carbaglu (carglumic acid), Carbatrol, Cardizem® (Diltiazem HCl for injection) Monvial®, Carrington patch, Caverject (alprostadil), Cayston (aztreonam for inhalation solution), CEA-Scan, Cedax (ceftibuten), Cefazolin and Dextrose USP, Ceftin (cefuroxime axetil), Celexa, CellCept, Cenestin, Cenestin, Cernevit, Cervarix [Human Papillomavirus Bivalent (Types 16 and 18) Vaccine, Recombinant, Cetrotide, Chantix (varenicline), Children's Advil (pediatric ibuprofen), Children's Motrin Cold, Chloraprep (chlorhexidine gluconate), Cialis (tadalafil), Cimetadine Hydrochloride Oral Solution 300 mg/5 ml, Cimetidine Hydrochloride Oral Solution, Cimetidine Hydrochloride Oral Solution, Cimzia (certolizumab pegol), Cimzia (certolizumab pegol), Cinryze (C1 Inhibitor (Human)), Cipro (ciprofloxacin HCl), Cipro (ciprofloxacin HCl), Cipro (ciprofloxacin) I.V. and Cipro (ciprofloxacin HCl) tablets, Clarinex, Clarithromycin (Biaxin), Claritin RediTabs (10 mg loratadine rapidlydisintegrating tablet), Claritin Syrup (loratadine), Claritin-D 24 Hour Extended Release Tablets (10 mg loratadine, 240 mg, pseudoephedrine sulfate), Clemastine fumarate syrup, Cleocin (clindamycin phosphate), Cleocin (clindamycin phosphate), Cleviprex (clevidipine), Climara, Clindamycin phosphate topical gel, Clindamycin Phosphate Topical Solution USP 1%, Clolar (clofarabine), Clomipramine hydrochloride, Clonazepam, Coartem (artemether/lumefantrine), Colazal (balsalazide disodium), Colcrys (colchicine), Combivir, Comtan, Concerta, Condylox Gel 0.5% (pokofilox), Confide, Copaxone, Corlopam, Corvert Injection (ibutilide fumarate injection), Cosopt, Covera-HS (verapamil), Crestor (rosuvastatin calcium), Crinone 8% (progesterone gel), Crixivan (Indinavir sulfate), Curosurf, Cuvposa (glycopyrrolate), Cycloset, bromocriptine mesylate, Cylert, Cymbalta (duloxetine), Dacogen (decitabine), Daptacel, Degarelix (degarelix for injection), DentiPatch (lidocaine transoral delivery system), Depakote (divalproex sodium), Depakote (divalproex sodium), Depakote ER (divalproex sodium), Dermagraft-TC, Desmopressin Acetate (DDAVP), Desmopressin Acetate (DDAVP), Desonate (desonide), Detrol (tolterodine tartrate), Detrol LA (tolterodine tartrate), Differin (adapalene gel) Gel, 0.1%, Diltiazem HCL, Extended-Release Capsules, Diovan (valsartan), Diovan (valsartan), Diovan HCT (valsartan), Ditropan XL (oxybutynin chloride), Ditropan XL (oxybutynin chloride), Doribax (doripenem), Dostinex Tablets (cabergoline tablets), Doxil (doxorubicin HCl liposome injection), Droxia, Dulera (mometasone furoate+formoterol fumarate dihydrate), DuoNeb (albuterol sulfate and ipratropium bromide), Durezol (difluprednate), dutasteride, Dynabac, DynaCirc CR, EDEX, Edluar (zolpidem tartrate), Effexor (venlafaxin HCL), Effexor XR (venlafaxin HCl), Efient (prasugrel), Egrifta (tesamorelin for injection), Elaprase (idursulfase), Elestrin (estradiol gel), Elidel, Eligard (leuprolide acetate), Elitek (rasburicase), ella (ulipristal acetate), Ellence, Elliotts B Solution (buffered intrathecal electrolyte/dextrose injection), Elmiron (pentosan polysulfate sodium), Eloxatin (oxaliplatin/5-fluorouracil/leucovorin), Embeda (morphine sulfate and naltrexone hydrochloride), Emend (aprepitant), Enbrel (etanercept), Entereg (alvimopan), Entocort EC (budesonide), Epivir (lamivudine), Epivir (lamivudine), Epogen, Eraxis (anidulafungin), Erbitux (cetuximab), Esclim, Estradiol tablets, Estradiol tablets, Estradiol Transdermal System, Estratab (0.3 mg), EstroGel (estradiol gel 0.06%), Estrostep (norethindrone acetate and ethinyl estradiol), Estrostep (norethindrone acetate and ethinyl estradiol), Estrostep (norethindrone acetate and ethinyl estradiol), Ethyol (amifostine), Ethyol (amifostine), Etodolac, Etodolac, Etodolac, Eulexin (flutamide), Evamist (estradiol), Evista (raloxifene hydrochloride), Evista (raloxifene hydrochloride), Evista (raloxifene hydrochloride), Evoxac, Exalgo (hydromorphone hydrochloride) extended release, Excedrin Migraine, Exelon (rivastigmine tartrate), Exelon (rivastigmine tartrate), Extavia (Interferon beta-1 b), Extina (ketoconazole), Fabrazyme (agalsidase beta), Famvir (famciclovir), Famvir (famciclovir), Fanapt (iloperidone), Faslodex (fulvestrant), Femara (letrozole), Femara (letrozole), Femhrt Tablets, FemPatch, Femstat 3 (butoconazole nitrate 2%), FEMSTAT One, Fenofibrate, Feraheme (ferumoxytol), Feridex I.V., Ferrlecit, Fertinex (urofollitropin for injection, purified), Finacea (azelaic acid) Gel, 15%, Finevin, Flagyl ER, FLOMAX, Flonase Nasal Spray, Flovent Rotadisk, Floxin otic, Floxin Tablets (ofloxacin tablets), FluMist (Influenza Virus Vaccine), Fluzone Preservativefree, Focalin (dexmethylphenidate HCl), Follistim™ (follitropin beta for injection), Folotyn (pralatrexate injection), Foradil Aerolizer (formoterol fumarate inhalation powder), Forteo (teriparatide), Fortovase, Fosamax (alendronate sodium), Fosrenol, lanthanum carbonate, Fragmin, Frova (frovatriptan succinate), Fusilev (levoleucovorin), Fuzeon (enfuvirtide), Galzin (zinc acetate), Gardasil (quadrivalent human papillomavirus 52 (types 6, 11, 16, 18), recombinant vaccine), Gastrocrom Oral Concentrate (cromolyn sodium), GastroMARK, Gelnique (oxybutynin chloride), Gemzar (gemcitabine HCL), Gemzar (gemcitabine HCL), Generic Transdermal Nicotine Patch, Genotropin (somatropin) injection, Genotropin (somatropin) lyophilized powder, Geodon (ziprasidone mesylate), Geref (sermorelin acetate for injection), Gilenya (fingolimod), Gleevec (imatinib mesylate), Gleevec (imatinib mesylate), Gliadel Wafer (polifeprosan 20 with carmustine implant), Glipizide Tablets, Glucagon, Glucagon, Glyburide Tablets, Glyburide Tablets, Glyburide Tablets, Glyset (miglitol), Gonal-F (follitropin alfa for injection), Halaven (eribulin mesylate), Havrix, Hectorol (Doxercalciferol) Injection, Hepsera (adefovir dipivoxil), Herceptin, Herceptin (trastuzumab), Hiberix (*Haemophilus* b Conjugate Vaccine; Tetanus Toxoid Conjugate), Humalog (insulin lispro), Humatrope (somatropin [rDNA origin] for injection), Humira (adalimumab), Hycamtin (topotecan hydrochloride), Hycamtin (topotecan hydrochloride), Iamin, Ilaris (canakinumab), Imagent (perflexane lipid microspheres), Imitrex (sumatriptan) injection and tablets, Imitrex (sumatriptan) nasal spray, Increlex (mecasermin), INFANRIX (Diphtheria and Tetanus Toxoids and Acellular Pertussis, Vaccine Adsorbed), Infasurf, INFERGEN (interferon alfacon-1), Inform HER-2/neu breast cancer test, Innohep (tinzaparin sodium) injectable, Inspra (eplerenone tablets), Integrilin, Intelence (etravirine), Interstim Continence Control Therapy, Intron A (Interferon alfa-2b, recombinant), Intron A (interferon alfa-2b, recombinant), Intron A (interferon alfa-2b, recombinant), Intuniv (guanfacine extended-release), Invanz, Invega (paliperidone), Invirase (saquinavir), Iontocaine, Iressa (gefitinib), Isentress (raltegravir), Istodax (romidepsin), IvyBlock, Ixempra (ixabepilone), Ixiaro (Japanese Encephalitis Vaccine, Inactivated, Adsorbed), Jalyn (dutasteride+tamsulosin), Januvia (sitagliptin phosphate), Jevtana (cabazitaxel), Kadian, Kalbitor (ecallantide), Kaletra Capsules and Oral Solution, Kapvay (clonidine hydrochloride), Keppra, Ketek (telithromycin), Ketoprofen, Kineret, Klaron (sodium sulfacet amide lotion) Lotion, 10%, Kogenate FS (Antihemophilic Factor Recombinant), Krystexxa (pegloticase), Kuvan (sapropterin dihydrochloride), Kytril (granisetron) solution, Kytril (granisetron) tablets, Lamictal (lamotrigine) Chewable Dispersible Tablets, Lamictal Chewable Dispersible Tablets, Lamisil (terbinafine hydrochloride) Dermagel, 1%, Lamisil (terbinafine hydrochloride) Solution, 1%, Lamisil (terbinafine hydrochloride) Tablets, Lamisil Solution, 1%, Lantus (insulin glargine [rDNA origin] injection), Lantus (insulin glargine [rDNA origin] injection), Latuda (lurasidone), Lescol (fluvastatin sodium), Lescol (fluvastatin sodium) capsules, Rx, Lescol XL (fluvastatin sodium) tablet, extended release, Letairis (ambrisentan), Leukine (sargramostim), Leukine (sargramostim), Levaquin, Levitra (vardenafil), Levo-T (levothyroxine sodium), Levoxyl, Lexapro (escitalopram oxalate), Lexiva (fosamprenavir calcium), Lexxel (enalapril maleate-felodipine ER), Lidoderm Patch (lidocaine patch 5%), Lithobid (Lithium Carbonate), Livalo (pitavastatin), Lodine (etodolac), Lodine XL (etodolac), Lodine XL (etodolac), Lotemax, Lotrisone (clotrimazole/betamethasone dipropionate) lotion, Lotronex (alosetron HCL) Tablets, Lovenox (enoxaparin sodium) Injection, Lovenox (enoxaparin sodium) Injection, Lovenox (enoxaparin sodium) Injection, Lucentis (ranibizumab), Lumigan (bimatoprost ophthalmic solution), Lunesta (eszopiclone), Lupron Depot (leuprolide acetate for depot suspension), Lupron Depot (leuprolide acetate for depot suspension), Lupron Depot (leuprolide acetate for depot suspension), Lusedra (fospropofol disodium), Lustra, LUVOX (fluvoxamine maleate), Luxiq (betamethasone valerate) Foam, Lyrica (pregabalin), Lysteda (tranexamic acid), Macugen (pegaptanib), Malarone (atovaquone; proguanil hydrochloride) Tablet, Marplan Tablets, Mavik (trandolapril), Maxalt, Mentax (1% butenafine HCl cream), Mentax (1% butenafine HCl cream), Mentax (1% butenafine HCl cream), Menveo (meningitis vaccine), MERIDIA, Merrem I.V. (meropenem), Mesnex, Metadate CD, Metaglip (glipizide/metformin HCl), Metaprotereol Sulfate Inhalation Solution, 5%, Metozolv ODT (metoclopramide hydrochloride), MetroLotion, Mevacor (lovastatin) tablets, Miacalcin (calcitonin-salmon) Nasal Spray, Micardis (telmisartan), Micardis HCT (telmisartan and hydrochlorothiazide), Microzide (hydrochlorothiazide), Migranal, Minoxidil Topical Solution 2% for Women, Miraluma test, Mirapex, Mircera (methoxy polyethylene glycol-epoetin beta), Mircette, Mirena (levonorgestrel-releasing intrauterine system), Mobic (meloxicam) Tablets, Monistat 3 (miconazole nitrate), Monistat 3 (miconazole nitrate), Monurol, Moxatag (amoxicillin), Mozobil (plerixafor injection), Multaq (dronedarone), Muse, Mylotarg (gemtuzumab ozogamicin), Myobloc, Myozyme (alglucosidase alfa), Naglazyme (galsulfase), Naltrexone Hydrochloride Tablets, Namenda (memantine HCl), Naprelan (naproxen sodium), Nasacort AQ (triamcinolone acetonide) Nasal Spray, Nasacort AQ (triamcinolone acetonide) Nasal Spray, NasalCrom Nasal Spray, Nascobal Gel (Cyanocobalamin, USP), Nasonex Nasal Spray, Natazia (estradiol valerate+ dienogest), Natrecor (nesiritide), Neulasta, Neumega, Neupogen, Neupro (rotigotine), Neurontin (gabapentin), Neurontin (gabapentin) oral solution, Neurontin (gabapentin) oral solution, Nexavar (sorafenib), Nexium (esomeprazole magnesium), Niaspan, NicoDerm CQ, Nicorette (nicotine polacrilex), Nicotrol nasal spray, Nicotrol transdermal patch, Nitrostat (nitroglycerin) Tablets, Nolvadex, NORCO tablets (Hydrocodone Bitartrate/Acetaminophen 10 mg/325 mg), Norditropin (somatropin (rDNA origin) for injection), Noritate, Normiflo, Norvir (ritonavir), Norvir (ritonavir), Novantrone (mitoxantrone hydrochloride), NovoLog (insulin aspart), Novolog Mix 70/30, Novothyrox (levothyroxine sodium), Noxafil (posaconazole), Nplate (romiplostim), Nuedexta (dextromethorphan hydrobromide and quinidine sulfate), Nutropin (somatropin-rDNA origin), Nutropin (somatropin-rDNA origin), NuvaRing, Nuvigil (armodafinil), Ocuflox (ofloxacin opthalmic solution) 0.3%, OcuHist, Oleptro (trazodone hydrochloride), Omnicef, Onglyza (saxagliptin), Onsolis (fentanyl buccal), Oral Cytovene, Oravig (miconazole), Orencia (abatacept), Orencia (abatacept), Orfadin (nitisinone), Ortho Evra, Ortho Tri-Cyclen Tablets (norgestimate/ethinyl estradiol), Ortho-Prefest, OsmoCyte Pillow Wound Dressing, Ovidrel (gonadotropin, chorionic human recombinant), Oxycodone and Aspirin, Oxycodone with Acetaminophen 5 mg/325 mg, OxyContin (oxycodone HCl controlled-release), Oxytrol (oxybutynin-transdermal system), Ozurdex (dexamethasone), Pancreaze (pancrelipase), Panretin Gel, Patanase (olopatadine hydrochloride), Paxil (paroxetine hydrochloride), Paxil CR (paroxetine hydrochloride), Paxil CR (paroxetine hydrochloride), Pediarix Vaccine, PegIntron (peginterferon alfa-2b), Pegasys (peginterferon alfa-2a), Pennsaid (diclofenac sodium topical solution), Pentoxifylline, Pepcid Complete, Periostat (doxycycline hyclate), Periostat (doxycycline hyclate), PhosLo, Photodynamic Therapy, Photofrin, Pindolol, Plavix (clopidogrel bisulfate), Plavix (clopidogrel bisulfate), Plenaxis (abarelix for injectable suspension), Posicor, Pradaxa (dabigatran etexilate mesylate), Pramipexole, Prandin, Pravachol (pravastatin sodium), Pravachol (pravastatin sodium), Precose (acarbose), Premarin (conjugated estrogens), Prempro, Prempro & Premphase (conjugated estrogens/medroxyprogesterone acetate tablets), PREVACID® (lansopraxole), PREVEN; Emergency Contraceptive Kit, Prevnar 13 (Pneumococcal 13-valent Conjugate Vaccine), Prevpac, Prevpac, Prezista (darunavir), Priftin, Prilosec (omeprazole), Prilosec (omeprazole), Prilosec (omeprazole), Prilosec (omeprazole)/Biaxin (clarithromycin) Combination Therapy, Prinivil or Zestril (Lisinopril), ProAmatine (midodrine), Procanbid (procainamide hydrochloride extended-release tablets), Prochloroperazine, Prochlorperazine, Prograf, Proleukin, Prolia (denosumab), Promacta (eltrombopag), Prometrium, Prometrium, Propecia, Proscar, Protonix (pantoprazole sodium) Delayed Release Tablets, Protonix (pantoprazole sodium) Delayed-Release Tablets, Protonix (pantoprazole sodium) Intravenous Formulation, Protopic (tacrolimus) ointment, Provenge (sipuleucel-T), Proventil HFA Inhalation Aerosol, Prozac Weekly (fluoxetine HCl), Pulmozyme (dornase alfa), Pulmozyme (dornase alfa), Quadramet (Samarium Sm 153 Lexidronam Injection), Quixin (levofloxacin), Qutenza (capsaicin), Qvar (beclomethasone dipropionate), Ranexa (ranolazine), Ranitidine Capsules, Ranitidine Tablets, Rapamune (sirolimus) oral solution, Rapamune (sirolimus) Tablets, Raplon, Raxar (grepafloxacin), Rebetol (ribavirin), REBETRON™ Combination Therapy, Rebif (interferon beta-1a), Reclast (zoledronic acid), Reclast (zoledronic acid), Redux (dexfenfluramine hydrochloride), Refludan, REGRANEX (becaplermin) Gel, Relenza, Relpax (eletriptan hydrobromide), Remeron (Mirtazapine), Remeron SolTab (mirtazapine), Remicade (infliximab), Remicade (infliximab), Reminyl (galantamine hydrobromide), Remodulin (treprostinil), Renagel (sevelamer hydrochloride), Renagel (sevelamer hydrochloride), RenaGelRenagel (sevelamer hydrochloride), Renova (tretinoin emollient cream), Renvela (sevelamer carbonate), ReoPro, REPRONEX (menotropins for injection, USP), Requip (ropinirole hydrochloride), Rescriptor Tablets (delavirdine mesylate tablets), Rescula (unoprostone isopropyl ophthalmic solution) 0.15%, RespiGam (Respiratory Syncitial Virus Immune Globulin Intravenous), Restasis (cyclosporine ophthalmic emulsion), Retavase (reteplase), Retin-A Micro (tretinoin gel) microsphere, 0.1%, Revlimid (lenalidomide), Reyataz (atazanavir sulfate), Rhinocort Aqua Nasal Spray, Rid Mousse, Rilutek (riluzole), Risperdal Oral Formulation, Ritalin LA (methylphenidate HCl), Rituxan, Rocephin, Rocephin, Rotarix (Rotavirus Vaccine, Live, Oral), Rotateq (rotavirus vaccine, live oral pentavalent), Rozerem (ramelteon), Rythmol, Sabril (vigabatrin), Saizen, Salagen Tablets, Samsca (tolvaptan), Sanctura (trospium chloride), Sancuso (granisetron), Saphris (asenapine), Savella (milnacipran hydrochloride), Sclerosol Intrapleural Aerosol, Seasonale, Lo Seasonale, Seasonique (ethinylestradiol+levonorgestrel), SecreFlo (secretin), Selegiline tablets, Self-examination breast pad, Selzentry (maraviroc), Sensipar (cinacalcet), Seprafilm, Serevent, Seroquel® (quetiapine fumarate) Tablets, Silenor (doxepin), Simponi (golimumab), Simulect, Singulair, Skelid (tiludronate disodium), Skin Exposure Reduction Paste Against Chemical Warfare Agents (SER-PACWA), Soliris (eculizumab), Somatuline Depot (lanreotide acetate), Somavert (pegvisomant), Sonata, Spectracef, Spiriva HandiHaler (tiotropium bromide), SPORANOX (itraconazole), Sprix (ketorolac tromethamine), Sprycel (dasatinib), Stavzor (valproic acid delayed release), Stelara (ustekinumab), Strattera (atomoxetine HCl), Stromectol (ivermectin), Subutex/Suboxone (buprenorphine/naloxone), Sulfamylon, Supartz, Supprelin LA (histrelin acetate), Sustiva, Sutent (sunitinib), Symlin (pramlintide), Synagis, Synercid I.V., Synthroid 58 (levothyroxine sodium), Synvisc, Synvisc-One (Hylan GF 20), Tamiflu capsule, Tarceva (erlotinib, OSI 774), Tasigna (nilotinib hydrochloride monohydrate), Tasmar, Tavist (clemastine fumarate), Tavist (clemastine fumarate), Taxol, Taxotere (Docetaxel), Tazorac topical gel, Teczem (enalapril maleate/diltiazem malate), Teflaro (ceftaroline fosamil), Tegretol (carbamazepine), Tegretol XR (carbamazepine), Tekamlo (aliskiren+amlodipine), Tekturna (aliskiren), Temodar, Tequin, Testim, Testoderm TTS CIII, Teveten (eprosartan mesylate plus hydrochlorothiazide), Teveten (eprosartan mesylate), Thalomid, Tiazac (diltiazem hydrochloride), Tiazac (diltiazem hydrochloride), Tiazac (diltiazem hydrochloride), Tikosyn Capsules, Tilade (nedocromil sodium), Tilade (nedocromil sodium), Tilade (nedocromil sodium), Timentin, Timentin, Tindamax, tinidazole, Tobi, Tolmetin Sodium, Topamax (topiramate), Topamax (topiramate), Toprol-XL (metoprolol succinate), Torisel (temsirolimus), Toviaz (fesoterodine fumarate), Tracleer (bosentan), Travatan (travoprost ophthalmic solution), Trazadone 150 mg, Treanda (bendamustine hydrochloride), Trelstar Depot (triptorelin pamoate), Trelstar LA (triptorelin pamoate), Tri-Nasal Spray (triamcinolone acetonide spray), Tribenzor (olmesartan medoxomil+amlodipine+hydrochlorothiazide), Tricor (fenofibrate), Tricor (fenofibrate), Trileptal (oxcarbazepine) Tablets, Trilipix (fenofibric acid), Tripedia (Diptheria and Tetanus Toxoids and Acellular Pertussis, Vaccine Absorbed), Trisenox (arsenic trioxide), Trivagizole 3 (clotrimazole) Vaginal Cream, Trivora-21 and Trivora-28, Trizivir (abacavir sulfate; lamivudine; zidovudine AZT) Tablet, Trovan, Twinrix, Tygacil (tigecycline), Tykerb (lapatinib), Tysabri (natalizumab), Tysabri (natalizumab), Tyvaso (treprostinil), Tyzeka (telbivudine), Uloric (febuxostat), Ultracet (acetaminophen and tramadol HCl), UltraJect, UroXatral (alfuzosin HCl 59 extended-release tablets), Urso, UVADEX Sterile Solution, Valcyte (valganciclovir HCl), Valstar, Valtrex (valacyclovir HCl), Vancenase AQ 84 mcg Double Strength, Vanceril 84 mcg Double Strength (beclomethasone dipropionate, 84 mcg), Inhalation Aerosol, Vaprisol (conivaptan), Vectibix (panitumumab), Velcade (bortezomib), Veltin (clindamycin phosphate and tretinoin), Venofer (iron sucrose injection), Ventolin HFA (albuterol sulfate inhalation aerosol), Veramyst (fluticasone furoate), Verapamil, Verdeso (desonide), Veregen (kunecatechins), VERSED (midazolam HCl), Vesicare (solifenacin succinate), Vfend (voriconazole), Viadur (leuprolide acetate implant), Viagra, Vibativ (telavancin), Victoza (liraglutide), Vidaza (azacitidine), Videx (didanosine), Vimovo (naproxen+esomeprazole), Vimpat (lacosamide), Vioxx (rofecoxib), VIRACEPT (nelfinavir mesylate), Viramune (nevirapine), Viread (tenofovir disoproxil fumarate), Viread (tenofovir disoproxil fumarate), Viroptic, Visicol Tablet, Visipaque (iodixanol), Vistide (cidofovir), Vistide (cidofovir), Visudyne (verteporfin for injection), Vitrasert Implant, Vitravene Injection, Vivelle (estradiol transdermal system), Vivelle (estradiol transdermal system), Vivelle-Dot (estradiol transdermal system), Vivitrol (naltrexone for extended-release injectable suspension), Vivitrol (naltrexone for extended-release injectable suspension), Votrient (pazopanib), Vpriv (velaglucerase alfa for injection), Vyvanse (Lisdexamfetamine Dimesylate), Warfarin Sodium tablets, Welchol (colesevelam hydrochloride), Western blot confirmatory device, Wilate (von Willebrand Factor/Coagulation Factor VIII Complex (Human), Xeloda, Xeloda, Xenazine (tetrabenazine), Xenical/Orlistat Capsules, Xeomin (incobotulinumtoxinA), Xgeva (denosumab), Xiaflex (collagenase *clostridium histolyticum*), Xifaxan (rifaximin), Xifaxan (rifaximin), Xigris (drotrecogin alfa [activated]), Xolair (omalizumab), Xopenex, Xyrem 60 (sodium oxybate), Xyzal (levocetirizine dihydrochloride), Yasmin (drospirenone/ethinyl estradiol), ZADITOR, Zagam (sparfloxacin) tablets, Zanaflex (tizanidine hydrochloride) Zantac 75 Efferdose, Zelnorm (tegaserod maleate) Tablets, Zelnorm (tegaserod maleate) Tablets, Zemaira (alpha1-proteinase inhibitor), Zemplar, Zenapax, Zenpep (pancrelipase), Zerit (stavudine), Zerit (stavudine), Zevalin (ibritumomab tiuxetan), Ziprasidone (ziprasidone hydrochloride), Zipsor (diclofenac potassium), Zirgan (ganciclovir ophthalmic gel), Zithromax (azithromycin), Zocor, Zofran, Zofran, Zoladex (10.8 mg goserelin acetate implant), Zoloft (sertraline HCl), Zoloft (sertraline HCl), Zoloft (sertraline HCl), Zometa (zoledronic acid), Zometa (zoledronic acid), Zomig (zolmitriptan), Zomig (zolmitriptan), Zonegran (zonisamide) Capsules, Zortress (everolimus), Zosyn (sterile piperacillin sodium/tazobactam sodium), Zuplenz (ondansetron oral soluble film), Zyban Sustained-Release Tablets, Zyclara (imiquimod), Zyflo (Zileuton), Zymaxid (gatifloxacin ophthalmic solution), Zyprexa, and Zyrtec (cetirizine HCl).

A useful measure of the efficacy of a compound (or, e.g., drug, medicinal formulation, or composition) is the "$EC_{50}$" which is the concentration at which the compound has half its maximal effect. For compounds whose effects re inhibitory, a similar measure that is often used is termed the "$IC_{50}$" which is the concentration at which the compound has half its maximal inhibitory effect.

In further embodiments, the compositions and formulations comprising follistatin modulating compound and an approved drug further comprise reduced glutathione.

In further embodiments, the compositions and formulations comprising follistatin modulating compound and an approved drug further comprise vitamin D.

In further embodiments, the compositions and formulations comprising follistatin modulating compound and an approved drug further comprise a B vitamin.

In a preferred embodiment, a compound or a drug of the classes exemplified herein, are combined with glutathione or an antioxidant in a nanoemulsion, nanoparticle, nanovault, nanofiber, or other nanostructure.

In a preferred embodiment, follistatin modulating compound is provided at a dosage suitable to achieve a plasma concentration of between 1 and 1000 uM.

In a further preferred embodiment, follistatin modulating compound is provided at a dosage suitable to achieve a plasma concentration of between 5 and 500 uM.

In a further preferred embodiment, follistatin modulating compound is provided at a dosage suitable to achieve a plasma concentration of between 15 and 100 uM.

In a preferred embodiment, follistatin modulating compound is provided in 250 mg, 500 mg, or 1000 mg doses at a frequency suitable to maintain a desirable plasma concentration.

In preferred embodiments, the ratio of follistatin modulating compound to other active compounds or agents in the compositions or formulations ranges from 1:50 to 50:1 based upon dry weight.

In further preferred embodiments, the ratio of follistatin modulating compound to other active compounds or agents in the compositions or formulations ranges from 1:10 to 10:1.

In a preferred embodiment, the ratio of follistatin modulating compound to glutathione is 1:1.

In a preferred embodiment, the ratio of follistatin modulating compound to glutathione is 1:4 to 1:10.

A combination of agents may also be administered. A method may further comprise monitoring in the subject the state of any of these conditions and/or the level of activation of follistatins, for example, in adipose tissue testing.

The present invention calls for the administration of a follistatin modulating agent, compound, or drug to a human in an amount effective for achieving its benefit. Typical daily doses of compounds comprising the formulation vary approximately in the range of 0.5 mg to 5000 mg. The effective amount of the compound to be administered can be readily determined by those skilled in the art, for example, through pre-clinical trials, clinical trials, and by methods known to scientists, physicians and clinicians.

A subject may undergo treatment utilizing a combination of an agent that increases the activity or protein level of a follistatin and an agent that increases the activity or protein level of UCP-1: e.g., an agent other than one that activates a follistatin. Activators of UCP1 include 5-amino-1-β-D-ribofuranosyl-imidazole-4-carboxamide (AICAR) or N,N-dimethylimidodicarbonimidic diamide (Metformin). Alternatively, the protein level of UCP-1 may be increased cellular infiltration, injection, or other means of transfection, with a nucleic acid encoding UCP-1. To increase the protein level of human UCP-1 in a cell, it may be necessary to introduce nucleic acids encoding each of the subunits of the protein; Nucleic acid sequences encoding the different subunits may be contained on the same or separate nucleic acid molecules.

Other diseases may subside after administering an agent that increases the activity or protein level of follistatin and/or UCP-1. Those diseases include certain renal diseases such as glomerulonephritis, glomerulosclerosis, nephrotic syndrome, and hypertensive nephrosclerosis. The aforementioned agents may also be useful for improving cognitive functions, treating diabetes, psoriasis, polycystic ovarian syndrome (PCOS), and preventing and treating bone loss.

High blood pressure, hypertension, high blood cholesterol, dyslipidemia, type 2 diabetes, insulin resistance, glucose intolerance, hyperinsulinemia, coronary heart disease, angina pectoris, congestive heart failure, stroke, gallstones, cholecystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), bladder control problems (such as stress incontinence); uric acid nephrolithiasis; psychological disorders (such as depression, eating disorders (see Yasuda, et al., Exp. Biol Med 2004), distorted body image, and low self-esteem) are all examples of diseases that would benefit from agents that contribute to weight loss. See Stunkard A J, Wadden T A. (Editors) Obesity: theory and therapy, Second Edition. New York: Raven Press, 1993. Finally, patients with AIDS are prone to developing lipodystrophy in response to AIDS combination therapies. Therefore, any of the aforementioned conditions can be treated or prevented by using weight gain preventative methods described herein.

Also provided herein are methods that would result in weight gain. A method may comprise administering a pharmaceutically effective amount of an agent that decreases the activity or protein level of a follistatin, or related compounds such as FST1 or FST2 (e.g., XM_003276522.1 and XM_003276523.1, respectively). A subject who has cachexia or would likely to develop cachexia would benefit from such treatment methods (see Acharyya, Am Assoc for Cancer Res (2006). Agents described herein would be effective. Administering a combination of agents would also be beneficial in causing weight gain. Monitoring the subject, the state of the disease or activation of follistatin in adipose tissue or other tissues might also be employed.

Methods that stimulate fat accumulation in cells may be used in vitro, to establish cellular weight gain models. The aforementioned models may be used for identifying additional drugs or substances that prevent weight gain.

Weight gain or fat accumulation in a cell or subject may further comprise decreasing the activity or protein level of an UCP-1. This can be achieved, e.g., by inhibiting the expression, transcription, translation or posttranslational modification of at least one of the three subunits of UCP-1, such as the catalytic subunit. Techniques known in the art, such as RNAi, antisense and ribozyme can be used. In addition, dominant negative mutants may be expressed in the cell.

Methods for modulating adipogenesis or fat cell differentiation, whether in vitro or in vivo, are recited herein. Modulating obesity may comprise utilizing high circulating levels of insulin and/or insulin like growth factor (IGF) 1 to prevent preadipocytes from differentiating to adipocytes. Follistatin activating compound contacting a cell would inhibit adipogenesis by increasing the protein level of a follistatin. Subcutaneous WAT mRNA levels of follistatin are inversely associated with obesity (Flanagan, et al., Endo Res, 2009). Contacting a cell with an agent that decreases the activity or protein level of a follistatin, such as a follistatin inhibiting compound, would be another method for stimulating adipogenesis.

Resveratrol activates UCP-1. Therefore, resveratrol and other follistatin activating compounds, in addition to those described above, may be used for treating or preventing conditions that can benefit from UCP-1 modulation.

Similarly, a compound or compounds that activate UCP1 may be used for the same purposes as follistatin activating compounds to extend lifespan, to make cells more resistant to stress and to protect cells against apoptosis (Yun, Phytochem, 2010).

Other methods provided herein reduce appetite, or increase satiety As a result; those methods cause weight loss or avoidance of weight gain. Methods may include administrating an amount of a follistatin activator or an agent that increases the protein level of a follistatin in the subject. A subject who is overweight, obese or a subject likely to become overweight or obese would benefit from such treatment. The method may comprise periodically administering a dose, e.g., in the form of a pill, to a subject. The dose may be an "appetite reducing dose."

This application recites assays for determining the likelihood that a subject has or will develop weight gain, obesity, insulin resistance, diabetes or precursor symptoms or resulting conditions. Such assays may comprise determining the level activity or expression (e.g., mRNA, pre-mRNA or protein) of a FST, such as FST1, or UCP-1 in a subject. A low level of follistatin activity or expression in a subject is likely to indicate that the subject has or is likely to develop weight gain, obesity, insulin resistance, diabetes, precursor symptoms thereof or secondary conditions thereof. Alternatively, a higher level of FST activity or expression in a subject is likely to indicate that the subject has or is likely to develop weight loss and be protected from developing high weight associated diseases, such as insulin resistance and diabetes. Other assays include determining the activity or level of expression of a follistatin and UCP-1.

Also disclosed herein are methods for identifying compounds that modulate weight gain and/or treat or prevent insulin resistance (or sensitivity) or diabetes. A method for identifying compounds that modulate weight gain and/or treat or prevent insulin resistance (or sensitivity) or diabetes may comprise identifying an agent that modulates the activity or protein level of a follistatin and testing whether the test agent modulates weight gain and/or can be used for treating or preventing insulin resistance or diabetes. The first step of the method may comprise contacting a FST with a test agent and determining the effect of the test agent on the activity of the follistatin, e.g., FST1, as described, e.g., in Howitz et al., supra. The first step of the method may also comprise contacting a cell comprising a follistatin with a test agent and determining the effect of the test agent on the activity of or expression level of the follistatin. Expression levels of a follistatin may be determined by measuring the mRNA, pre-mRNA or protein level of the follistatin (Froguel, Exp Biol Med, 2001). The second step of the method may comprise testing the agent in an animal model for obesity, insulin resistance and/or diabetes. Such animal models are well known in the art. Screening methods may further comprise a step to determine the toxicity or adverse effects of the agents.

Other screening assays comprise identifying agents that modulate UCP-1 activity or protein levels. There is a need for compounds that activate UCP-1 but do not have the toxicities or adverse effects of known UCP-1 activators, such as metformin/phenformin, pharmaceutical formulations, and administration modes.

With respect to the present invention, these methods may vary and are not limited to those described herein.

Within the pre-clinical and clinical period, any method known to the art may be employed for contacting a cell, organ or tissue with an agent, compound, or drug. Suitable methods include in vitro, ex vivo, or in vivo methods. In vitro methods include cultured samples. For example, a cell can be placed in medium and incubated with a compound, agent or drug under conditions suitable for assaying its activity (especially follistatin-like activity). Appropriate incubation conditions may be readily determined by those skilled in the art.

An effective amount of a compound, agent or drug useful in the methods of the present invention, may be administered to an animal by known methods. The compound may be administered systemically or locally.

Administration

With respect to the present invention, an agent, compound, or drug may, for example, be administered orally, parenterally (e.g. intravenously, intramuscularly, subcutaneously), intranasally, topically, or transdermally (e.g. Cevc and Blume, 2001). Other routes of administration include rectal administration, intrathecal administration, administration involving mucosal absorption, and administration in aerosolized form (e.g. U.S. Pat. No. 5,126,123; U.S. Pat. No. 5,544,646).

The present invention covers the administration of compositions or formulations useful in the methods of the invention to an animal by sustained release. Such administration is selected when it is considered beneficial to achieve a certain level of the drug in a body compartment over a longer period of time (e.g. serum or plasma concentration).

In alternate embodiments, the compositions and formulations of the present invention are suitable for oral administration including extended release formulations (e.g. Pouton, 2000; Prasad et al., 2003; WO/2010/137027; WO/2020/129337; WO/2010/127100; WO/2010/127191; WO/2010/119300; WO/2010/114801; WO/2010/103544), and controlled release formulations (WO 02/083106; U.S. Pat. No. 5,567,439; U.S. Pat. No. 6,838,094; U.S. Pat. No. 6,863,902; U.S. Pat. No. 6,905,708).

The present invention includes any formulation known to the art that is suitable for administration of the agents, drugs, and compositions useful in the methods of the present invention. Examples include tablets (U.S. Pat. No. 4,209,513), capsules (e.g. US 2010/0021535; U.S. Pat. No. 7,011,846), such as gelatin capsules (e.g. U.S. Pat. No. 5,698,155), pills, troches (e.g. U.S. Pat. No. 3,312,594), elixirs, suspensions, syrups (e.g. U.S. Pat. No. 6,790,837), wafers (e.g. Wen and Park, 2010), chewing gum (e.g. Chaudhary and Shahiwala, 2010; Semwal et al. 2010); U.S. Pat. No. 6,531,114; Surana et al, 2010), etc.

The present compositions and formulations therefore, can take the form of solutions, suspensions, emulsion, tablets, pills, pellets, capsules, capsules containing liquids, powders, sustained-release formulations, suppositories, emulsions, aerosols, sprays, suspensions, or any other form suitable for use. Examples of suitable pharmaceutical vehicles are also described in Remington's Pharmaceutical Sciences, Alfonso R. Gennaro ed., Mack Publishing Co. Easton, Pa., 19th ed., 1995, pp. 1447 to 1676, incorporated herein by reference.

The compositions or formulations of the present invention can be mixed with suitable pharmaceutical carriers (vehicles) or excipients known to the art (e.g. Kumar et al., 1996; Akers et al., 2002; Strickley et al., 2004; Jacob et al., 2010; Siddiqui et al., 2010; Pilcer et al., 2010) (Burns, et al., U.S. Pat. No. 7,388,112, 2008). Examples include water-soluble organic solvents, nonionic surfactants, water-insoluble lipids, organic liquids/semi-solids, cyclodextrins and phospholipids. They may also include gelatin, lactic acid, stearic acid or salts thereof, starch, milk, sugar, certain types of clay, including magnesium or calcium stearate, talc, oils, gums, vegetable fats or and glycols. The use of lipid based drug delivery systems enhances bioavailability of compounds. Self-emulsifying drug delivery systems (SEDDS) are a class of lipid based delivery systems, prepared in liquid dosage form and delivered by way of soft gelatin capsules. A form of solid-SEDDS may also be employed to deliver such compounds, whereby the SEDDS ingredients are solidified and the self-emulsifying ingredients are in powder form (Rajesh, et al., JGPT, 2010).

The buffering agents of the present invention may be any salt or buffering agent. Examples include sodium chloride, potassium chloride, or sodium phosphate or potassium phosphate.

In alternate embodiments, the compositions and formulations of the present invention are the product of mixing compounds, agents and drugs in their dry or solid forms and subsequently loading those compounds, agents and drugs into liposomes (e.g. see Langer, 1990. Science 249:1527-1533; Treat et al, in Liposomes in the Therapy of Infectious Disease and Cancer, Lopez-Berestein and Fidler (eds), Liss, N.Y., pp. 353-365 (1989); Lopez-Berestein, ibid., pp. 317-327).

In alternate embodiments, the compositions and formulations of the present invention are the product of mixing compounds, agents and drugs in their dry or solid forms and subsequently loading those compounds, agents and drugs into solid lipid nanoparticles. The ability to incorporate drugs into nanocarriers offers a new prototype in drug delivery that could be used for secondary and tertiary levels of drug targeting (Mukerjee, et al., IJPS, 2009).

In alternate embodiments, the compositions and formulations of the present invention are the product of mixing compounds, agents and drugs in their dry or solid forms followed by loading those compounds, agents and drugs into solid lipid nanoparticles and/or liposomes followed by drying or lyophilizing the mixture.

In a further alternate embodiment, the dried or lyophilized liposomes and/or solid lipid nanoparticles are encapsulated for oral administration (Wassim, et al., Advanced Drug Delivery Reviews, 2006).

In embodiments involving a stabilizer, the stabilizer may be any suitable stabilizer known to the art (e.g. Stella and Rajewski, 1997; Merisko-Liversidge and Liversidge, 2003; U.S. Pat. No. 5,376,359). The stabilizer, may for example, be an amino acid, such as for instance, glycine; or an oligosaccharide, such as for example, sucrose, tetralose, lactose or a dextran. The stabilizer may also be a sugar alcohol, such as mannitol or a combination the stabilizer types described above. The unique features of nanosuspensions have enabled their use in various dosage forms, including specialized delivery systems such as mucoadhesive hydrogels (Patravale, et al., J. of Pharm and Pharm, 2003).

In an alternate embodiment, a stabilizer or stabilizers constitute approximately 0.1% to about 10% weight for weight of the compound.

In an alternate embodiment, the surfactant is a nonionic surfactant (e.g. polysorbate or Tween20).

In an alternate embodiment, Tween80; a polyethylene glycol or a polyoxyethylene polyoxypropylene glycol is included at approximately 0.001% (w/v) to about 10% (w/v).

In an alternate embodiment, the formulations of the compositions or formulations useful in the methods of the present invention contain one or more conventional additives.

Additives include a solubilizer (e.g. US20070021325; U.S. Pat. No. 6,669,964). Additives may comprise glycerol or an antioxidant such as for example, benzalkonium chloride, benzyl alcohol, chloretone or chlorobutanol. Additives may also include an anesthetic.

To reduce oxidation and spoilage, the pharmaceutical compositions and formulations may be stored under nitrogen gas or argon gas in sealed vials. In some embodiments, an increase in FST expression is detected by methods analogous to those of US.

U.S. Pat. No. 5,532,127 (Assay for 1-CAM related protein expression); U.S. Pat. No. 7,091,046 (Multiplexed protein expression and activity assay; U.S. Pat. No. 5,506,121 (Fusion peptides with binding activity for streptavidin); U.S. Pat. No. 6,103,493 (Use of a polypeptide in a method for the isolation, purification or determination of proteins); 5783398 (High throughput assay using fusion proteins); U.S. Pat. No. 6,576,424 (Arrays and methods for detecting nucleic acids); U.S. Pat. No. 6,919,211 (The methods make use of a plurality of sequence specific recognition reagents which can also be used for classification of biological samples, and to characterize their sources); U.S. Pat. No. 6,534,266 (An in situ hybridization method for detecting and specifically identifying transcription of a multiplicity of different target sequences in a cell is disclosed); U.S. Pat. No. 7,846,693 (Nucleic acid detection assay); U.S. Pat. No. 5,723,591 (An oligonucleotide probe is provided which includes a fluorescent reporter molecule and a quencher molecule capable of quenching the fluorescence of the reporter molecule); U.S. Pat. No. 5,741,642 (Assay for detecting the expression of a gene encoding human keratinocyte) as well as UK patent 2272698 (Strep-tag technology for protein purification and detection is covered by U.S. Pat. No. 5,506,121, UK patent 2272698 and French patent 93 13 066; Strep-Tactin is covered by U.S. Pat. No. 6,103, 493), which are each incorporated by reference in their entirety herein.

Pharmaceutical compositions for use in accordance with the present methods may be formulated in conventional manner using one or more physiologically acceptable carriers or excipients (Haile, US20020157126. Thus, follistatin-modulating or -inhibiting compounds and their physiologically acceptable salts and solvates may be formulated for administration by, for example, injection, inhalation or insufflation (either through the mouth or the nose) or oral, buccal, parenteral or rectal administration.

In one embodiment, the compound is administered locally, at the site where the target cells, e.g., fat cells, are present in adipose tissue.

Compounds can be formulated to address the need for systemic and topical administration. Techniques and formulations generally may be found in Remmington's Pharmaceutical Sciences, Meade Publishing Co., Easton, Pa. For example injection of a substance would be employed for systemic administration, including intramuscular, intravenous, intraperitoneal, and subcutaneous injection. Compounds can be titrated in liquid solutions, preferably in physiologically compatible buffers such as Hank's solution or Ringer's solution. In addition, the compounds are administered as solids that are redissolved or suspended immediately prior to use. Lyophilized forms are also included (Levin, Pharmaceutical Process Scale-Up, 2001).

Oral pharmaceutical compositions may take the form of, for example, tablets, lozanges, or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound (see Koontz, Department of Food Science and Technology, 2006).

Compounds may be conveniently delivered in the form of an aerosol spray presentation from pressurized packs or a nebuliser with the use of a suitably, commercially available propellant to permit inhalation therapy. Suitable propellants are dichlorodifluoromethane, trichlorofluoromethane, dichlorotefrafluoroethane, carbon dioxide or other non-reactive gas. In the case of a pressurized aerosol the dosage unit may be determined by providing a valve to deliver a metered amount. Capsules and cartridges of e.g., gelatin, for use in an inhaler or insufflator may be formulated containing a powder mix of the compound and a suitable powder base such as lactose or starch (Kahkashan, Pharmacopeial Forum, 2008).

Parenteral administration can be achieved by bolus injection or continuous infusion. Formulations for injection may be presented in unit dosage form, such as ampoules, or in multi-dose containers, with an added preservative. The compositions may be compounded as suspensions, solutions or emulsions in oily or aqueous vehicles, and may contain suspending, stabilizing and/or dispersing agents. Alternatively, the active ingredient may be in powder form for reconstitution with a suitable vehicle, e.g., sterile pyrogen-free water, before use.

Compounds such as rectal compositions, i.e., suppositories or retention enemas can contain conventional suppository bases such as cocoa butter or other glycerides.

In addition to the formulations described previously, the compounds may take the form of a depot preparation, which is a long acting formulation (Zhang, U.S. Pat. No. 8,093, 288). Administration by implantation (for example subcutaneously or intramuscularly) or by intramuscular injection would be the route of choice. The compounds may be formulated with suitable polymeric or hydrophobic materials, ion exchange resins (Mahore, Intl. J. Pharm. Sci. Rev. Res. 2010), or as sparingly soluble derivatives, for example, as a sparingly soluble salt (see Eberwine US20090227531). Ferrogels comprise another mode of time release delivery of compounds and cells. In addition, a new active porous scaffold can be remotely controlled by a magnetic field to deliver various biological agents on demand. The active porous scaffold, in the form of a macroporous ferrogel, gives a large deformation and volume change of over 70% under a moderate magnetic field. The deformation and volume variation allows a new mechanism to trigger and enhance the release of various compounds from the scaffold. The porous scaffold can also act as a depot of various cells, whose release can be controlled by external magnetic fields (Zhao, PNAS, 2010). Controlled release formula also includes patches.

Pharmaceutical compositions (including cosmetic preparations) may also be beneficial and may comprise from about 0.00001 to 100% such as from 0.001 to 10% or from 0.1% to 5% by weight of one or more compounds described herein.

In one embodiment, a compound described herein, is incorporated into a topical formulation containing a topical carrier that is generally suited to topical drug administration and comprising any such material known in the art. The topical carrier may be an ointment, lotion, cream, microemulsion, gel, oil, solution, or the like, and may be comprised of a naturally occurring or synthetic material. The selected carrier should not adversely affect the active agent or other components of the topical formulation. Examples of suitable topical carriers include water, alcohols and other nontoxic organic solvents, glycerin, mineral oil, silicone, petroleum jelly, lanolin, fatty acids, vegetable oils, parabens, waxes, and the like.

Formulations may be colorless, odorless ointments, lotions, creams, micro-emulsions and gels.

Ointments are generally semisolid preparations and typically based on petrolatum or other petroleum derivatives. The specific, useful ointment base is one that will provide for optimum drug delivery, and, preferably, will provide emolliency or the like. As with other carriers or vehicles, an ointment base should be inert, stable, nonirritating and nonsensitizing Ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Exemplary water-soluble ointment bases are prepared from polyethylene glycols (PEGs) of varying molecular weight; again, reference may be had to Remington's, supra, for further information.

Compounds may be compounded as lotions, to be applied to the skin surface without friction. Lotions are typically liquid or semiliquid preparations in which solid particles, including the active agent, are present in a water or alcohol base. Lotions are usually suspensions of solids, and may comprise a liquid oily emulsion of the oil-in-water type. Lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like. An exemplary lotion formulation for use in conjunction with the present method contains propylene glycol mixed with a hydrophilic petrolatum such as that which may be obtained under the trademark Aquaphor® from Beiersdorf, Inc. (Norwalk, Conn.).

Compounds may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant.

Compounds may be compounded as microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9). For the preparation of microemulsions, surfactant (emulsifier), co-surfactant (co-emulsifier), an oil phase and a water phase are necessary. Suitable surfactants include emulsifiers that are typically used in the preparation of creams. The co-surfactant (or "co-emulsifer") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

Further examples of such particulate carrier systems are the polymeric nanoparticles (Speiser, 1973; Kreuter 1978; Marty et al. 1978; Couvreur et al. 1979; Luck et al. 1998), microemulsions (Bangham 1993), liposomes (Bangham 1993), solid lipid nanoparticles (SLN) (Morel et al. 1996; Almeida et al. 1997; Garcia-Fuentes et al 2002; Muller et al 2002a, 2006; Ugazio et al 2002; Gualbert et al 2003; Carsten et al 2004; Hu et al 2004; Garcia-Fuentes, Prego et al 2005; Garcia-Fuentes, Torres et al 2005; Schubert and Muller-Goymann 2005; Pedersen et al 2006; Souto and Muller 2006; Trotta et al 2006; Zhang et al 2006), nanostructured lipid carriers (NLC) (Muller et al 2002a; Garcia-Fuentes, Prego, et al 2005; Garcia-Fuentes, Torres, et al 2005) and self-emulsified drug delivery systems (SEDDS) (Gursoy and Benita 2004; Robert 2004; Zheng and Fulu 2006). Incorporation of drugs or therapeutic substances into a particulate carrier system will protect them against degradation in vitro and in vivo. The release rate can be modified.

Compounds may be compounded as gel formulations, which generally are two-phase, semisolid systems consisting of either suspension made up of small inorganic particles or single phase gels, which incorporate large organic molecules distributed substantially uniformly throughout a carrier liquid. Single phase gels can be made, for example, by combining the active agent, a carrier liquid and a suitable gelling agent such as tragacanth (at 2 to 5%), sodium alginate (at 2-10%), gelatin (at 2-15%), methylcellulose (at 3-5%), sodium carboxymethylcellulose (at 2-5%), carbomer (at 0.3-5%) or polyvinyl alcohol (at 10-20%) together and mixing until a characteristic semisolid product is produced. Other suitable gelling agents include methylhydroxycellulose, polyoxyethylene-polyoxypropylene, hydroxyethylcellulose and gelatin. Although gels commonly employ aqueous carrier liquid, alcohols and oils can be used as the carrier liquid as well.

Various additives may be included in formulations, e.g., topical formulations. Examples of additives include, but are not limited to, solubilizers, skin permeation enhancers, opacifiers, preservatives (e.g., anti-oxidants), gelling agents, buffering agents, surfactants (particularly nonionic and amphoteric surfactants), emulsifiers, emollients, thickening agents, stabilizers, humectants, colorants, fragrance, and the like. Inclusion of solubilizers and/or skin permeation enhancers is particularly preferred, along with emulsifiers, emollients and preservatives. An optimum topical formulation comprises approximately: 2 wt. % to 60 wt. %, preferably 2 wt. % to 50 wt. %, solubilizer and/or skin permeation enhancer; 2 wt. % to 50 wt. %, preferably 2 wt. % to 20 wt. %, emulsifiers; 2 wt. % to 20 wt. % emollient; and 0.01 to 0.2 wt. % preservative, with the active agent and carrier (e.g., water) making of the remainder of the formulation.

A skin permeation enhancer facilitates passage of therapeutic levels of active agent through a reasonably sized area of unbroken skin. Suitable enhancers include, for example: lower alkanols such as methanol ethanol and 2-propanol; alkyl methyl sulfoxides such as dimethylsulfoxide (DMSO), decylmethylsulfoxide ($C_{10}$ MSO) and tetradecylmethyl sulfoxide; pyrrolidones such as 2-pyrrolidone, N-methyl-2-pyrrolidone and N-(-hydroxyethyl) pyrrolidone; urea; N,N-diethyl-m-toluamide; $C_2$-$C_6$ alkanediols; miscellaneous solvents such as dimethyl formamide (DMF), N,N-dimethylacetamide (DMA) and tetrahydrofurfuryl alcohol; and the 1-substituted azacycloheptan-2-ones, particularly 1-n-dodecylcyclazacycloheptan-2-one (laurocapram; available under the trademark Azone® from Whitby Research Incorporated, Richmond, Va.).

Examples of solubilizers include, but are not limited to, the following: hydrophilic ethers such as diethylene glycol monoethyl ether (ethoxydiglycol, available commercially as Transcutol®) and diethylene glycol monoethyl ether oleate (available commercially as Softcutol®); polyethylene castor oil derivatives such as polyoxy 35 castor oil, polyoxy 40 hydrogenated castor oil, etc.; polyethylene glycol, particularly lower molecular weight polyethylene glycols such as PEG 300 and PEG 400, and polyethylene glycol derivatives such as PEG-8 caprylic/capric glycerides (available commercially as Labrasol®); alkyl methyl sulfoxides such as DMSO; pyrrolidones such as 2-pyrrolidone and N-methyl-2-pyrrolidone; and DMA. Many solubilizers can also act as absorption enhancers. A single solubilizer may be incorporated into the formulation, or a mixture of solubilizers may be incorporated therein.

Suitable emulsifiers and co-emulsifiers include, without limitation, those emulsifiers and co-emulsifiers described with respect to microemulsion formulations. Emollients include, for example, propylene glycol, glycerol, isopropyl myristate, polypropylene glycol-2 (PPG-2) myristyl ether propionate, and the like.

Other active agents such as anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate) may also be included in formulations.

In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Topical skin treatment compositions for example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507. Accordingly, closed containers containing a cosmetically acceptable composition are provided as herein defined.

In an alternative embodiment, a pharmaceutical formulation for oral or parenteral administration is provided. The aforementioned type of formulation may comprise an activating compound-containing microemulsion as described above, and may contain alternative pharmaceutically acceptable carriers, vehicles, additives, etc. particularly suited to oral or parenteral drug administration. Alternatively, an activating compound-containing microemulsion may be administered orally or parenterally substantially as described above, without modification.

Administration of a follistatin activator or inhibitor may be followed by measuring a factor in the subject, such as measuring the activity of the follistatin. In an illustrative embodiment, a cell is obtained from a subject following administration of an activating or inhibiting compound to the subject, such as by obtaining a biopsy, and the activity of the FST or follistatin expression level is determined in the biopsy. Alternatively, biomarkers, such as plasma biomarkers may be followed. Biomarkers may be adipose cell derived secretary proteins, such as leptin, adiponectin, and resistin. The cell may be any cell of the subject, but in cases in which an activating compound is administered locally, the cell is preferably a cell that is located in the vicinity of the site of administration. The cell may be an adipocyte.

Weight, body mass, blood glucose sugar levels, blood lipid levels and any other factor may be measured for monitoring diseases or conditions described herein.

An expression vector may be employed to introduce and express a nucleic acid encoding a FST, an UCP-1 or molecules that will reduced the protein level of a follistatin or UCP-1 in a cell. Exemplary expression vectors include adenoviral vectors or adenoviral-associated viruses (AAV). These vectors, as well as others and methods for infecting target cells are well known in the art. Alternatively, nucleic acids may also be introduced into cells using liposomes or similar technologies.

Numerous chemical definitions, chemical structures, and formulae for compounds and compound classes, useful in the present invention, as well as exemplary formulations are further described in patent applications WO2005/065667 (Compositions for treating or preventing obesity and insulin resistance disorders) as well as other patent applications and articles referenced herein.

Kits

Kits for therapeutic and other purposes are also provided herein, including kits for modulating fat accumulation. A kit may comprise one or more agent that modulates follistatin or UCP1 protein activity or level, e.g., follistatin activating or inhibitory compounds, such as those described herein, and optionally devices for contacting cells with the agents. Devices include syringes, stents and other devices for introducing a compound into a subject or applying it to the skin of a subject.

Further, a kit may also contain components for measuring a factor, e.g., described above, such as the activity of follistatin proteins, e.g., in tissue samples. Cignal Reporter Assays® are a powerful tool for deciphering gene function, as well as determining the mechanisms of action of proteins, peptides, ligands, and small molecule compounds, and such kits are useful for investigative purposes stated herein.

Kits for diagnosing the likelihood of having or developing weight gain, obesity, insulin-resistance, diabetes, precursors thereof or secondary conditions thereof are recited herein. A kit may comprise an agent for measuring the activity and or expression level of a follistatin or UCP-1 (Erlich, WO 2011/107482 A2).

Kits to use as screening assays comprise one or more agents for conducting a screening assay, such as a follistatin, an UCP1 or a biologically active portion thereof, or a cell or cell extract comprising such. Any of the kits may also comprise instructions for use.

The present description is further illustrated by the following examples, which should not be construed as limiting in any way. The contents of all cited references (including literature references, issued patents, published and patent applications) are hereby expressly incorporated by reference.

The practice of the present methods will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the Treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

Equivalents

Those skilled in the art will recognize, or be able to ascertain using no more than routine experimentation, many equivalents of the specific embodiments described herein. Such equivalents are intended to be encompassed by the claims recited herein.

All patents and patent publications cited herein are incorporated by reference in their entireties.

III. Examples

The following are examples of methods and compositions of the invention. It is understood that various other embodiments may be practiced, given the general description provided above.

Applicant has discovered a novel function of follistatin (Fst), an activin binding protein for increasing the synthesis of major proteins responsible for increased energy expenditure and regulating lipid metabolism. Applicant discloses that up-regulation of a follistatin domain containing protein (follistatin) is positively associated with brown adipose tissue differentiation and that compounds increasing follistatin expression can be utilized to treat or prevent an obesity related disorder. Methods, compositions, uses of compositions, assays and kits for modulating overall brown adipose tissue (BAT) mass in animals and patients with obesity, insulin resistance and perturbed glucose homeostasis are disclosed. Accordingly, methods, compositions, uses of compositions, and kits are useful for the amelioration of pathological conditions characterized by storage of excess energy, insulin resistance and related metabolic syndromes often associated with obesity. The uses of the compositions and the methods include administration of physiologically relevant concentrations of recombinant Fst protein to promote the production of UCP1 and several other BAT specific proteins responsible for burning excess energy as well as other related proteins involved in brown fat differentiation.

Example 1—Genetic Approach for the Isolation of Fst KO and WT Embryos, Culture of Mouse Embryonic Fibroblasts (MEFs) and their Differentiation Follistatin (Fst) knockout mice die shortly after birth and have therefore not been previously well-studied. While Fst knockout mice (Fst KO mice) display multiple developmental defects, it is shown here that these animals also lack brown adipose tissue (BAT), a critical tissue for thermogenesis. It is further demonstrated that lack of follistatin is associated with a down regulation of proteins associated with brown fat differentiation including uncoupling protein 1 (UCP-1).

Generation of Fst KO and WT Embryos, Culture of Mouse Embryonic Fibroblasts (MEFs) and their Differentiation FIG. 1 depicts the genetic approach for the isolation of Fst KO and WT embryos, culture of mouse embryonic fibroblasts (MEFs) and their differentiation. Briefly, follistatin heterozygous (Fst+/−) male and female mice (obtained from Dr. Martin Matzuk, MD., PhD, Department of Human Genetics, Baylor College of Medicine, Houston, Tex.) were allowed to breed. Methods for producing KO mice are disclosed, for example, in U.S. Pat. No. 6,548,738. Day 13 pregnant female mice were sacrificed, and embryos were collected. The head, limbs, and the internal organs were removed from the embryos, and the carcasses were rinsed with 1×PBS and minced. Minced carcasses were suspended with 3 ml 0.025% trypsin/EDTA (Invitrogen) and incubated at 37° C. for 20 min. The trypsin was neutralized, after two trypsinization cycles, by adding the equal volume of cell culture media (DMEM supplemented with 10% fetal bovine serum, 20 mM glutamine, and penicillin/streptomycin). Cell suspensions were centrifuged and resuspended with cell culture media and plated out to three T-75 flasks per embryo and cultured at 37° C. with 95% air and 5% $CO_2$.

Genotyping was performed with the embryos to ascertain the specific genotype (wild type or +/+, heterozygote or +/−, or knock out (−/−) using the following primer sets—

1. 5'-ATCTATCGCCCTTGGGTCTT-3' (SEQ ID NO:40) and 5'-AAAACCTACCGCAACGAATG-3' (SEQ ID NO:41), which amplifies a 152 bp fragment in wild type (+/+) and heterozygous (+/−) littermates.
2. 5'-GGTGGGAAATGTCACCTGAT-3' (SEQ ID NO:42) and 5'-CGGTGGATGTGGAATGTGT-3' (SEQ ID NO:43), which amplified a 262 bp fragment in homozygous (KO, −/−; WT, +/+) and heterozygous (+/−) littermates.

WT and KO cultures were marked after completion of genotyping. When the cells are confluent, entire cells were split into four to five 100 mm dishes and cultured until confluent. For differentiation, 1-day post confluent cells (designated day 0) were treated with growth medium containing 1 μM dexamethasone (Sigma Chemicals), 0.5 mM methylisobutylxanthene (IBMX), 5 μg insulin/ml and 0.5 μM rosiglitazone (Sigma Chemicals) for 48 h. After 48 h, the medium contained 5 μg insulin/ml and 0.5 μM rosiglitazone and was changed every other day for up to day 6. Cells were collected and proceeded for gene and protein expression analysis as well as cellular bioenergetics assays.

Gene and Protein Expression Analysis of MEF Cultures.
i. Real Time Quantitative PCR Analysis Total cellular RNA obtained from Fst KO and Fst WT MEFs were analyzed by quantitative real-time PCR analysis using mouse Fst and β-actin primers. Real time quantitative PCR analysis confirmed the absence of Fst gene in Fst KO mouse embryonic fibroblast (MEF) primary culture. (FIG. 2A)

ii. Western Blot Analysis

Primary MEF cultures from Fst KO and Fst WT were allowed to grow in 100 mm dishes until confluence. When the cells are confluent, entire cells were split into four to five 100 mm dishes and cultured until confluent. For differentiation, 1-day post confluent cells (designated day 0) were treated with growth medium containing 1 μM dexamethasone (Sigma Chemicals), 0.5 mM methylisobutylxanthene (IBMX), 5 μg insulin/ml and 0.5 μM rosiglitazone (Sigma Chemicals) for 48 h. After 48 h, the medium contained 5 μg insulin/ml and 0.5 μM rosiglitazone and was changed every other day for up to day 5. Early passage MEFs (passage≤3) was used for each experiment in order to avoid senescence. Cells were lysed, and 50-100 μg total cell lysates were electrophoresed on 4-15% gradient gels. Gels were transferred to polyvinylidene difluoride (PVDF) membranes and probed using anti-adipocyte fatty acid binding protein 2 (AP-2), anti-CCAAT-enhancer binding protein-alpha (CEBPα), anti-peroxisome proliferator-activated receptor gamma (PPARγ), anti-PR domain containing 16 (PRDM16), anti-uncoupling protein-1 (UCP-1) or anti-glyceraldehyde 3 phosphate dehydrogenase (GAPDH) antibodies and appropriate horseradish peroxidase (HRP)-linked secondary antibodies. Immunoreactive bands were detected using enhanced chemiluminiscence (ECL) detection agents.

Western blot analysis showed the down-regulation of key BAT differentiation markers in Fst KO cultures undergoing adipogenic differentiation for 5 days. (FIG. 2B) Image Quant software was used to quantitate the relative densitometric values. Data are presented as mean±SD, and between group differences were analyzed. p values ≤0.05 were considered statistically significant. The experiments were repeated three times and data from representative experiments are shown. (FIG. 2C)

Affymetrix Gene Expression Analysis.

MEFs were cultured from Fst WT and Fst KO embryos under brown adipogenic differentiation conditions for 48 hours. Cells were collected and total cellular RNA was isolated. Integrity of the RNA was analyzed and Affymetrix gene expression analysis was performed to compare the gene expression profile of several key genes involved in energy production between the WT and Fst KO groups. The gene expression analysis demonstrated down-regulation of several key genes involved in energy production in Fst KO mouse embryonic fibroblast (MEF) cultures undergoing brown fat differentiation for 48 hours. (Table 1) Gene symbol, gene name and fold changes (Fst KO vs. WT) are presented.

TABLE 1

| Symbol | RefSeq (mRNA) ID | Entrez Gene Name | Fold Change (WT vs. KO) |
|---|---|---|---|
| ABCD2 | NM_011994 | ATP-binding cassette, sub-family D (ALD), member 2 | −1.916 |

TABLE 1-continued

| Symbol | RefSeq (mRNA) ID | Entrez Gene Name | Fold Change (WT vs. KO) |
|---|---|---|---|
| ABHD5 | NM_026179 | abhydrolase domain containing 5 | −1.556 |
| ACSL1 | NM_007981 | acyl-CoA synthetase long-chain family member 1 | −9.019 |
| ADH7 | NM_009626 | alcohol dehydrogenase 7 (class IV), mu or sigma polypeptide | −1.876 |
| ADH1C | NM_007409 | alcohol dehydrogenase 1C (class I), gamma polypeptide | −1.807 |
| ADIPOQ | NM_009605 | adiponectin, C1Q and collagen domain containing | −36.754 |
| ALB | NM_009654 | albumin | −2.854 |
| ALDOB | NM_144903 | aldolase B, fructose-bisphosphate | −1.634 |
| AOC3 | NM_009675 | amine oxidase, copper containing 3 (vascular adhesion protein 1) | −3.631 |
| APOA1 | NM_009692 | apolipoprotein A-I | −3.189 |
| APOA2 | NM_013474 | apolipoprotein A-II | −2.810 |
| APOE | NM_009696 | apolipoprotein E | −1.671 |
| C3 | NM_009778 | complement component 3 | −3.743 |
| CD36 | NM_001159555 | CD36 molecule (thrombospondin receptor) | −3.897 |
| CP | NM_001042611 | ceruloplasmin (ferroxidase) | −2.269 |
| CYP2F1 | NM_000774 | cytochrome P450, family 2, subfamily F, polypeptide 1 | −1.545 |
| CYP3A4 | NM_017460 | cytochrome P450, family 3, subfamily A, polypeptide 4 | −3.377 |
| EPAS1 | NM_010137 | endothelial PAS domain protein 1 | −1.615 |
| FABP1 | NM_017399 | fatty acid binding protein 1, liver | −2.549 |
| FMO1 | NM_010231 | flavin containing monooxygenase 1 | −1.581 |
| FMO2 | NM_018881 | flavin containing monooxygenase 2 (non-functional) | −1.635 |
| GPD1 | NM_010271 | glycerol-3-phosphate dehydrogenase 1 (soluble) | −3.453 |
| HPGD | NM_008278 | hydroxyprostaglandin dehydrogenase 15-(NAD) | −1.740 |
| LIPE | NM_001039507 | lipase, hormone-sensitive | −2.595 |
| LPL | NM_008509 | lipoprotein lipase | −2.548 |
| MAOB | NM_172778 | monoamine oxidase B | −1.517 |
| MLXIPL | NM_021455 | MLX interacting protein-like | −1.915 |
| PNPLA2 | NM_001163689 | patatin-like phospholipase domain containing 2 | −2.022 |
| PPARG | NM_001127330 | peroxisome proliferator-activated receptor gamma | −4.698 |
| PPARGC1A | NM_008904 | peroxisome proliferator-activated receptor gamma, coactivator 1 alpha | −2.164 |
| PPARGC1B | NM_133249 | peroxisome proliferator-activated receptor gamma, coactivator 1 beta | −1.702 |
| RETN | NM_022984 | resistin | −1.784 |
| SCD | NM_024450 | stearoyl-CoA desaturase (delta-9-desaturase) | −1.773 |
| SNCA | NM_001042451 | synuclein, alpha (non A4 component of amyloid precursor) | 1.595 |
| UCP2 | NM_011671 | uncoupling protein 2 (mitochondrial, proton carrier) | −2.255 |
| XDH | NM_011723 | xanthine dehydrogenase | −2.285 |

The Affymetrix gene expression analysis also demonstrated down-regulation of several key genes involved in lipid metabolism in Fst KO MEFs undergoing brown fat differentiation for 48 hours. (Table 2)

TABLE 2

| Symbol | Entrez Gene Name | Fold Change |
|---|---|---|
| A130040M12Rik | RIKEN cDNA A130040M12 gene | −1.861 |
| ABCB1 | ATP-binding cassette, sub-family B (MDR/TAP), member 1 | −1.588 |
| ABCD2 | ATP-binding cassette, sub-family D (ALD), member 2 | −1.916 |
| ABHD5 | abhydrolase domain containing 5 | −1.556 |
| ACE | angiotensin I converting enzyme (peptidyl-dipeptidase A) 1 | −1.697 |
| ACLY | ATP citrate lyase | 1.529 |
| ACSL1 | acyl-CoA synthetase long-chain family member 1 | −9.019 |
| ADH7 | alcohol dehydrogenase 7 (class IV), mu or sigma polypeptide | −1.876 |
| ADH1C | alcohol dehydrogenase 1C (class I), gamma polypeptide | −1.807 |
| ADIPOQ | Adiponectin, C1Q and collagen domain containing | −36.754 |
| ADRA2A | adrenergic, alpha-2A-, receptor | 1.614 |
| AFP | alpha-fetoprotein | −2.829 |
| AGPAT2 | 1-acylglycerol-3-phosphate O-acyltransferase 2 (lysophosphatidic acid acyltransferase, beta) | −2.327 |
| AGPAT9 | 1-acylglycerol-3-phosphate O-acyltransferase 9 | −4.863 |
| AGT | angiotensinogen (serpin peptidase inhibitor, clade A, member 8) | −2.597 |
| ALB | albumin | −2.854 |

TABLE 2-continued

| Symbol | Entrez Gene Name | Fold Change |
|---|---|---|
| AMBP | alpha-1-microglobulin/bikunin precursor | −2.955 |
| ANG | angiogenin, ribonuclease, RNase A family, 5 | 3.004 |
| ANGPTL4 | angiopoietin-like 4 | −2.405 |
| APOA1 | apolipoprotein A-I | −3.189 |
| APOA2 | apolipoprotein A-II | −2.810 |
| APOC1 | apolipoprotein C-I | −3.153 |
| APOC2 | apolipoprotein C-II | −4.251 |
| APOD | apolipoprotein D | −1.715 |
| APOE | apolipoprotein E | −1.671 |
| APOH | apolipoprotein H (beta-2-glycoprotein I) | −1.971 |
| ASPG | asparaginase homolog (S. cerevisiae) | −1.682 |
| ATP1A2 | ATPhase, Na+/K+ transporting, alpha 2 polypeptide | −4.170 |
| C3 | complement component 3 | −3.743 |
| CAV2 | caveolin 2 | −1.584 |
| CCL2 | chemokine (C—C motif) ligand 2 | −1.503 |
| CCL11 | chemokine (C—C motif) ligand 11 | −2.725 |
| CD7 | CD7 molecule | 1.540 |
| CD14 | CD14 molecule | −1.535 |
| CD36 | CD36 molecule (thrombospondin receptor) | −3.897 |
| CEBPA | CCAAT/enhancer binding protein (C/EBP), alpha | −2.151 |
| CIDEA | cell death-inducing DFFA-like effector a | −2.615 |
| CIDEC | cell death-inducing DFFA-like effector c | −2.418 |
| CLEC11A | C-type lectin domain family 11, member A | 1.697 |
| CPS1 | carbamoyl-phosphate synthase 1, motochondrial | −4.028 |
| CSF1R | colony stimulating factor 1 receptor | −1.520 |
| CYB5A | cytochrome b5 type A (microsomal) | −1.601 |
| CYP11B1 | cytochrome P450, family 11, subfamily B, polypeptide 1 | −1.621 |
| CYP2J2 | cytochrome P450, family 2, subfamily J, polypeptide 2 | −1.563 |
| CYP3A4 | cytochrome P450, family 3, subfamily A, polypeptide 4 | −3.377 |
| CYP3A43 | cytochrome P450, family 3, subfamily A, polypeptide 43 | −2.888 |
| CYP7B1 | cytochrome P450, family 7, subfamily B, polypeptide 1 | −1.798 |
| DCC | deleted in colorectal carcinoma | 1.504 |
| DGAT2 | diacylglycerol O-acyltransferase 2 | −2.645 |
| DKK1 | dickkopf homolog 1 (Xenopus laevis) | 1.541 |
| DRD1 | dopamine receptor D1 | −1.597 |
| DSP | desmoplakin | 1.519 |
| EDNRB | endothelin receptor type B | −1.791 |
| ELOVL2 | ELOVL fatty acid elongase 2 | −2.693 |
| ENPP2 | ectonucleotide pyrophosphatase/phosphodiesterase 2 | −1.549 |
| EPAS1 | endothelial PAS domain protein 1 | −1.615 |
| EPHX1 | epoxide hydrolase 1, microsomal (xenobiotic) | 1.512 |
| EPHX2 | epoxide hydrolase 2, cytoplasmic | −1.739 |
| F2 | coagulation factor II (thrombin) | −1.822 |
| FABP1 | fatty acid binding protein 1, liver | −2.549 |
| FABP4 | fatty acid binding protein 4, adipocyte | −6.313 |
| FCGR2A | Fc fragment of IgG, low affinity IIa, receptor (CD32) | −1.642 |
| Fcrls | Fc receptor-like S, scavenger receptor | 1.506 |
| FGF9 | fibroblast growth factor 9 (glia-activating factor) | 1.603 |
| FOXO4 | forkhead box O4 | 1.565 |
| FST | follistatin | −38.105 |
| G6PC | glucose-6-phosphatase, catalytic subunit | −1.576 |
| GFRA2 | GDNF family receptor alpha 2 | −1.793 |
| GPD1 | glycerol-3-phosphate dehydrogenase 1 (soluble) | −3.453 |
| HP | haptoglobin | −10.126 |
| HPGD | hydroxyprostaglandin dehydrogenase 15-(NAD) | −1.740 |
| HPX | hemopexin | −2.628 |
| HSD3B2 | hydroxy-delta-5-steroid dehydrogenase, 3 beta- and steroid delta-isomerase 2 | −1.693 |
| IL1R1 | interleukin 1 receptor, type I | −1.629 |
| KITLG | KIT ligand | −2.049 |
| KLF2 | Kruppel-like factor 2 (lung) | 1.518 |
| LECT1 | leukocyte cell derived chemotaxin 1 | −3.351 |
| LIPE | lipase, hormone-sensitive | −2.595 |
| LIPH | lipase, member H | −1.642 |
| LPL | lipoprotein lipase | −2.548 |
| MGST2 | microsomal glutathione S-transferase 2 | −1.793 |
| MLXIPL | MLX interacting protein-like | −1.915 |
| MTMR7 | myotubularin related protein 7 | 1.624 |
| Mup1 (includes others) | major urinary protein 1 | −3.963 |
| NAMPT | nicotinamide phosphoribosyltransferase | −1.576 |
| NPPA | natriuretic peptide A | 3.233 |
| Nppb | natriuretic peptide type B | 1.520 |
| NUDT7 | nudix (nucleoside diphosphate linked moiety X)-type motif 7 | −1.522 |
| PCK1 | phosphoenolpyruvate carboxykinase 1 (soluble) | −2.481 |
| PCSK9 | proprotein convertase subtilisin/kexin type 9 | −1.543 |
| PDE8B | phosphodiesterase 8B | 1.592 |

TABLE 2-continued

| Symbol | Entrez Gene Name | Fold Change |
|---|---|---|
| PDPN | podoplanin | 1.868 |
| PLA1A | phospholipase A1 member A | −1.824 |
| PLA2G16 | phospholipase A2, group XVI | −1.964 |
| PLG | plasminogan | −4.777 |
| PLIN2 | perilipin 2 | −1.578 |
| PNPLA2 | patatin-like phospholipase domain containing 2 | −2.022 |
| PNPLA3 | patatin-like phospholipase domain containing 3 | −2.172 |
| PPARG | peroxisome proliferator-activated receptor gamma | −4.698 |
| PPARGC1A | peroxisome proliferator-activated receptor gamma, coactivator 1 alpha | −2.164 |
| PPARGC1B | peroxisome proliferator-activated receptor gamma, coactivator 1 beta | −1.702 |
| PPBP | pro-platelet basic protein (chemokine (C—X—C motif) ligand 7) | 1.557 |
| PRKAR2B | protein kinase, cAMP-dependent, regulatory, type II, beta | −1.709 |
| PRLR | prolactin receptor | −2.029 |
| PTGDS | prostaglandin D2 synthase 21 kDa (brain) | −1.914 |
| PTGIS | prostaglandin I2 (prostacyclin) synthase | 1.506 |
| RARRES2 | retinoic acid receptor responder (tazarotene induced) 2 | −2.419 |
| RBP4 | retinol binding protein 4, plasma | −2.658 |
| RDH12 | retinol dehydrogenase 12 (all-trans/9-cis/11-cis) | −2.360 |
| RETN | resistin | −1.784 |
| SAA1 | serum amyloid A1 | −4.073 |
| SCAP | SREBF chaperone | 1.500 |
| SCD | stearoyl-CoA desaturase (delta-9-desaturase) | −1.773 |
| SCHIP1 | schwannomin interacting protein 1 | 1.671 |
| SERINC2 | serine incorporator 2 | 2.085 |
| SERPINA1 | serpin peptidase inhibitor, clade A (alpha-1 antiproteinase, antitrypsin), member 1 | −3.585 |
| SERPINA6 | serpin peptidase inhibitor, clade A (alpha-1 antiproteinase, antitrypsin), member 6 | −1.790 |
| SLPI | secretory leukocyte peptidase inhibitor | −1.824 |
| SNCA | synuclein, alpha (non A4 component of amyloid precursor) | 1.595 |
| STAR | steroidogenic acute regulatory protein | −1.808 |
| STARD4 | StAR-related lipid transfer (START) domain containing 4 | −1.567 |
| SULT1A1 | sulfotransferase family, cytosolic, 1A, phenol-preferring, member 1 | −1.627 |
| THRSP | thyroid hormone responsive | −11.672 |
| TLR4 | toll-like receptor 4 | −1.546 |
| TNXB | tenascin XB | −1.936 |
| TTPA | tocopherol (alpha) transfer protein | −2.235 |
| TTR | transthyretin | −2.060 |
| UCP1 | uncoupling protein 1 (mitochondrial, proton carrier) | −2.850 |
| UCP2 | uncoupling protein 2 (mitochondrial, proton carrier) | −2.255 |
| UGT1A1 | UDP glucuronosyltransferase 1 family, polypeptide A1 | −1.555 |
| UGT2B10 | UDP glucuronosyltransferase 2 family, polypeptide B10 | −1.730 |
| VTN | vitronectin | −2.332 |
| XDH | xanthine dehydrogenase | −2.285 |

Table 3 provides accession numbers identifying the genes (e.g., GenBank accession numbers) involved in lipid metabolism demonstrating down-regulation in Fst KO MEFs undergoing brown fat differentiation for 48 hours.

TABLE 3

Changes in genes involved in lipid metabolism by Follistatin

| Symbol | RefSeq (mRNA) ID | Entrez Gene Name | Fold Change (WT vs. KO) |
|---|---|---|---|
| ABCB1 |  | ATP-binding cassette, sub-family B (MDR/TAP), member 1 | −1.588 |
| ABCD2 | NM_011994 | ATP-binding cassette, sub-family D (ALD), member 2 | −1.916 |
| ABHD5 | NM_026179 | abhydrolase domain containing 5 | −1.556 |
| ACE | NM_009598 | angiotensin I converting enzyme (peptidyl-dipeptidase A) 1 | −1.697 |
| ACLY | NM_134037 | ATP citrate lyase | 1.529 |
| ACSL1 | NM_007981 | acyl-CoA synthetase long-chain family member 1 | −9.019 |
| ADH7 | NM_009626 | alcohol dehydrogenase 7 (class IV), mu or sigma polypeptide | −1.876 |
| ADH1C | NM_007409 | alcohol dehydrogenase 1C (class I), gamma polypeptide | −1.807 |
| ADIPOQ | NM_009605 | adiponectin, C1Q and collagen domain containing | −36.754 |
| ADRA2A | NM_007417 | adrenergic, alpha-2A-, receptor | 1.614 |
| AFP | NM_007423 | alpha-fetoprotein | −2.829 |
| AGPAT2 | NM_026212 | 1-acylglycerol-3-phosphate O-acyltransferase 2 (lysophosphatidic acid acyltransferase, beta) | −2.327 |

TABLE 3-continued

Changes in genes involved in lipid metabolism by Follistatin

| Symbol | RefSeq (mRNA) ID | Entrez Gene Name | Fold Change (WT vs. KO) |
|---|---|---|---|
| AGPAT9 | NM_172715 | 1-acylglycerol-3-phosphate O-acyltransferase 9 | −4.863 |
| AGT | NM_007428 | angiotensinogen (serpin peptidase inhibitor, clade A, member 8) | −2.597 |
| ALB | NM_009654 | albumin | −2.854 |
| AMBP | NM_007443 | alpha-1-microglobulin/bikunin precursor | −2.955 |
| ANG | NM_001161731 | angiogenin, ribonuclease, RNase A family, 5 | 3.004 |
| ANGPTL4 | NM_020581 | angiopoietin-like 4 | −2.405 |
| APOA1 | NM_009692 | apolipoprotein A-I | −3.189 |
| APOA2 | NM_013474 | apolipoprotein A-II | −2.810 |
| APOC1 | NM_001110009 | apolipoprotein C-I | −3.153 |
| APOC2 | NM_009695 | apolipoprotein C-II | −4.251 |
| APOD | NM_007470 | apolipoprotein D | −1.715 |
| APOE | NM_009696 | apolipoprotein E | −1.671 |
| APOH | NM_013475 | apolipoprotein H (beta-2-glycoprotein I) | −1.971 |
| ASPG | NM_001081169 | asparaginase homolog (S. cerevisiae) | −1.682 |
| ATP1A2 | NM_178405 | ATPase, Na+/K+ transporting, alpha 2 polypeptide | −4.170 |
| C3 | NM_009778 | complement component 3 | −3.743 |
| CAV2 | NM_016900 | caveolin 2 | −1.584 |
| CCL2 | NM_011333 | chemokine (C—C motif) ligand 2 | −1.503 |
| CCL11 | NM_011330 | chemokine (C—C motif) ligand 11 | −2.725 |
| CD7 | NM_009854 | CD7 molecule | 1.540 |
| CD14 | NM_009841 | CD14 molecule | −1.535 |
| CD36 | NM_001159555 | CD36 molecule (thrombospondin receptor) | −3.897 |
| CEBPA | NM_007678 | CCAAT/enhancer binding protein (C/EBP), alpha | −2.151 |
| CIDEA | NM_007702 | cell death-inducing DFFA-like effector a | −2.615 |
| CIDEC | NM_178373 | cell death-inducing DFFA-like effector c | −2.418 |
| CLEC11A | NM_009131 | C-type lectin domain family 11, member A | 1.697 |
| CPS1 | NM_001080809 | carbamoyl-phosphate synthase 1, mitochondrial | −4.028 |
| CSF1R | NM_001037859 | colony stimulating factor 1 receptor | −1.520 |
| CYB5A | NM_001190807 | cytochrome b5 type A (microsomal) | −1.601 |
| CYP11B1 | NM_001033229 | cytochrome P450, family 11, subfamily B, polypeptide 1 | −1.621 |
| CYP2J2 | NM_000775 | cytochrome P450, family 2, subfamily J, polypeptide 2 | −1.563 |
| CYP3A4 | NM_017460 | cytochrome P450, family 3, subfamily A, polypeptide 4 | −3.377 |
| CYP3A43 | NM_022820 | cytochrome P450, family 3, subfamily A, polypeptide 43 | −2.888 |
| CYP7B1 | NM_007825 | cytochrome P450, family 7, subfamily B, polypeptide 1 | −1.798 |
| DCC | NM_007831 | deleted in colorectal carcinoma | 1.504 |
| DGAT2 | NM_026384 | diacylglycerol O-acyltransferase 2 | −2.645 |
| DKK1 | NM_010051 | dickkopf homolog 1 (Xenopus laevis) | 1.541 |
| DRD1 | NM_010076 | dopamine receptor D1 | −1.597 |
| DSP | NM_023842 | desmoplakin | 1.519 |
| EDNRB | NM_001136061 | endothelin receptor type B | −1.791 |
| ELOVL2 | NM_019423 | ELOVL fatty acid elongase 2 | −2.693 |
| ENPP2 | NM_001136077 | ectonucleotide pyrophosphatase/phosphodiesterase 2 | −1.549 |
| EPAS1 | NM_010137 | endothelial PAS domain protein 1 | −1.615 |
| EPHX1 | NM_010145 | epoxide hydrolase 1, microsomal (xenobiotic) | 1.512 |
| EPHX2 | NM_007940 | epoxide hydrolase 2, cytoplasmic | −1.739 |
| F2 | NM_010168 | coagulation factor II (thrombin) | −1.822 |
| FABP1 | NM_017399 | fatty acid binding protein 1, liver | −2.549 |
| FABP4 | NM_024406 | fatty acid binding protein 4, adipocyte | −6.313 |
| FCGR2A | NM_001136219 | Fc fragment of IgG, low affinity IIa, receptor (CD32) | −1.642 |
| Fcrls | NM_030707 | Fc receptor-like S, scavenger receptor | 1.506 |
| FGF9 | NM_013518 | fibroblast growth factor 9 (glia-activating factor) | 1.603 |
| FOXO4 | NM_018789 | forkhead box O4 | 1.565 |
| FST | NM_008046 | follistatin | −38.105 |
| G6PC | NM_008061 | glucose-6-phosphatase, catalytic subunit | −1.576 |
| GFRA2 | NM_008115 | GDNF family receptor alpha 2 | −1.793 |
| GPD1 | NM_010271 | glycerol-3-phosphate dehydrogenase 1 (soluble) | −3.453 |
| HP | NM_017370 | haptoglobin | −10.126 |
| HPGD | NM_008278 | hydroxyprostaglandin dehydrogenase 15-(NAD) | −1.740 |
| HPX | NM_017371 | hemopexin | −2.628 |
| HSD3B2 | NM_153193 | hydroxy-delta-5-steroid dehydrogenase, 3 beta- and steroid delta-isomerase 2 | −1.693 |
| IL1R1 | NM_001123382 | interleukin 1 receptor, type I | −1.629 |
| KITLG | NM_013598 | KIT ligand | −2.049 |
| KLF2 | NM_008452 | Kruppel-like factor 2 (lung) | 1.518 |
| LECT1 | NM_010701 | leukocyte cell derived chemotaxin 1 | −3.351 |
| LIPE | NM_001039507 | lipase, hormone-sensitive | −2.595 |
| LIPH | NM_001083894 | lipase, member H | −1.642 |
| LPL | NM_008509 | lipoprotein lipase | −2.548 |

TABLE 3-continued

Changes in genes involved in lipid metabolism by Follistatin

| Symbol | RefSeq (mRNA) ID | Entrez Gene Name | Fold Change (WT vs. KO) |
|---|---|---|---|
| MGST2 | NM_174995 | microsomal glutathione S-transferase 2 | −1.793 |
| MLXIPL | NM_021455 | MLX interacting protein-like | −1.915 |
| MTMR7 | NM_001040699 | myotubularin related protein 7 | 1.624 |
| Mup1 | NM_001045550 | major urinary protein 1 | −3.963 |
| NAMPT | NM_021524 | nicotinamide phosphoribosyltransferase | −1.576 |
| NPPA | NM_008725 | natriuretic peptide A | 3.233 |
| Nppb | NM_008726 | natriuretic peptide type B | 1.520 |
| NUDT7 | NM_024437 | nudix (nucleoside diphosphate linked moiety X)-type motif 7 | −1.522 |
| PCK1 | NM_011044 | phosphoenolpyruvate carboxykinase 1 (soluble) | −2.481 |
| PCSK9 | NM_153565 | proprotein convertase subtilisin/kexin type 9 | −1.543 |
| PDE8B | NM_172263 | phosphodiesterase 8B | 1.592 |
| PDPN | NM_010329 | podoplanin | 1.868 |
| PLA1A | NM_134102 | phospholipase A1 member A | −1.824 |
| PLA2G16 | NM_139269 | phospholipase A2, group XVI | −1.964 |
| PLG | NM_008877 | plasminogen | −4.777 |
| PLIN2 | NM_007408 | perilipin 2 | −1.578 |
| PNPLA2 | NM_001163689 | patatin-like phospholipase domain containing 2 | −2.022 |
| PNPLA3 | NM_054088 | patatin-like phospholipase domain containing 3 | −2.172 |
| PPARG | NM_001127330 | peroxisome proliferator-activated receptor gamma | −4.698 |
| PPARGC1A | NM_008904 | peroxisome proliferator-activated receptor gamma, coactivator 1 alpha | −2.164 |
| PPARGC1B | NM_133249 | peroxisome proliferator-activated receptor gamma, coactivator 1 beta | −1.702 |
| PPBP | NM_023785 | pro-platelet basic protein (chemokine (C—X—C motif) ligand 7) | 1.557 |
| PRKAR2B | NM_011158 | protein kinase, cAMP-dependent, regulatory, type II, beta | −1.709 |
| PRLR | NM_011169 | prolactin receptor | −2.029 |
| PTGDS | NM_008963 | prostaglandin D2 synthase 21 kDa (brain) | −1.914 |
| PTGIS | NM_008968 | prostaglandin I2 (prostacyclin) synthase | 1.506 |
| RARRES2 | NM_027852 | retinoic acid receptor responder (tazarotene induced) 2 | −2.419 |
| RBP4 | NM_001159487 | retinol binding protein 4, plasma | −2.658 |
| RDH12 | NM_030017 | retinol dehydrogenase 12 (all-trans/9-cis/11-cis) | −2.360 |
| RETN | NM_022984 | resistin | −1.784 |
| SAA1 | NM_009117 | serum amyloid A1 | −4.073 |
| SCAP | NM_001001144 | SREBF chaperone | 1.500 |
| SCD | NM_009128 | stearoyl-CoA desaturase (delta-9-desaturase) | −1.773 |
| SCHIP1 | NM_001113419 | schwannomin interacting protein 1 | 1.671 |
| SERINC2 | NM_172702 | serine incorporator 2 | 2.085 |
| SERPINA1 | NM_009243 | serpin peptidase inhibitor, clade A (alpha-1 antiproteinase, antitrypsin), member 1 | −3.585 |
| SERPINA6 | NM_007618 | serpin peptidase inhibitor, clade A (alpha-1 antiproteinase, antitrypsin), member 6 | −1.790 |
| SLPI | NM_011414 | secretory leukocyte peptidase inhibitor | −1.824 |
| SNCA | NM_001042451 | synuclein, alpha (non A4 component of amyloid precursor) | 1.595 |
| STAR | NM_011485 | steroidogenic acute regulatory protein | −1.808 |
| STARD4 | NM_133774 | StAR-related lipid transfer (START) domain containing 4 | −1.567 |
| SULT1A1 | NM_133670 | sulfotransferase family, cytosolic, 1A, phenol-preferring, member 1 | −1.627 |
| THRSP | NM_009381 | thyroid hormone responsive | −11.672 |
| TLR4 | NM_021297 | toll-like receptor 4 | −1.546 |
| TNXB | NM_031176 | tenascin XB | −1.936 |
| TTPA | NM_015767 | tocopherol (alpha) transfer protein | −2.235 |
| TTR | NM_013697 | transthyretin | −2.060 |
| UCP1 | NM_009463 | uncoupling protein 1 (mitochondrial, proton carrier) | −2.850 |
| UCP2 | NM_011671 | uncoupling protein 2 (mitochondrial, proton carrier) | −2.255 |
| UGT1A1 | NM_013701 | UDP glucuronosyltransferase 1 family, polypeptide A1 | −1.555 |
| UGT2B10 | NM_001075 | UDP glucuronosyltransferase 2 family, polypeptide B10 | −1.730 |
| VTN | NM_011707 | vitronectin | −2.332 |
| XDH | NM_011723 | xanthine dehydrogenase | −2.285 |

Validation of Gene Expression Analysis.
 i. Real Time Quantitative PCR

Figure 3:
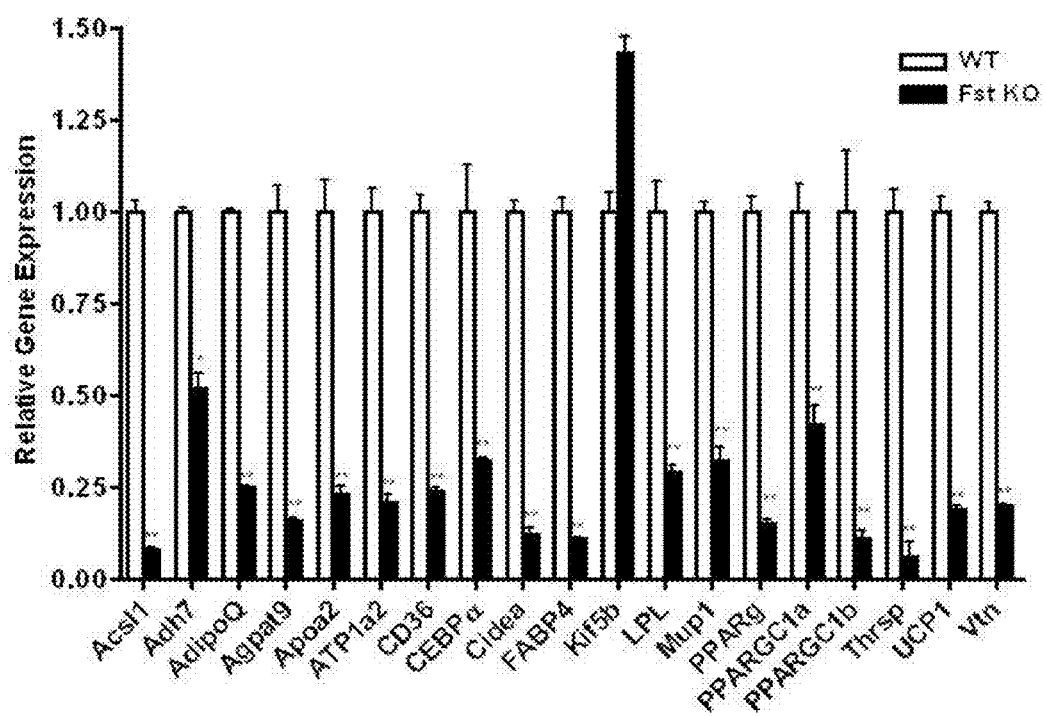
FIG. 3 shows the validation of Affymetrix gene expression analysis by real time quantitative PCR.

Affymetrix gene expression analysis was validated by real time quantitative PCR. (FIG. 3) Total RNA was extracted by using Trizol reagent, and equal amounts (2 µg) of RNA were reverse transcribed using RNA High Capacity cDNA kit (Applied Bio systems, Foster City, Calif.). The Power Sybr Green PCR master mix was used with 7500 fast real-time PCR system (Applied Biosystems). The primer pairs used are shown below.

TABLE 4

(SEQ ID NOs: 2-39)

| Primer | Forward | Reverse |
|---|---|---|
| Acsl1 | 5'-CTGATTGACATTCGGCAGTACG-3' (SEQ ID NO: 2) | 5'-CCCCATGAGGGTGTTGGTTG-3' (SEQ ID NO: 3) |
| Adh7 | 5'-GCAAAGCGGCTGTCCTATG-3' (SEQ ID NO: 4) | 5'-GCCAAAATCTTAACACGGACTTC-3' (SEQ ID NO: 5) |
| AdipoQ | 5'-CGCCGCCTTCTTCTACCTG-3' (SEQ ID NO: 6) | 5'-CGAAGCCATAGTAGCTGATGGAA-3' (SEQ ID NO: 7) |
| Agpat9 | 5'-CGGATTATCCCTGGGTATCTCG-3' (SEQ ID NO: 8) | 5'-CGAAGTCCCTTCCTCGAAGAC-3' (SEQ ID NO: 9) |
| Apoa2 | 5'-GCAGACGGACCGGATATGC-3' (SEQ ID NO: 10) | 5'-GCTGCTCGTGTGTCTTCTCA-3' (SEQ ID NO: 11) |
| Atp1a2 | 5'-TGAGCTGGGCCGAAAATACC-3' (SEQ ID NO: 12) | 5'-GGGTCCATCTCTAGCCAGAAT-3' (SEQ ID NO: 13) |
| CD36 | 5'-ATGGGCTGTGATCGGAACTG-3' (SEQ ID NO: 14) | 5'-AGCCAGGACTGCACCAATAAC-3' (SEQ ID NO: 15) |
| Cebp-α | 5'-GCGGGAACGCAACAACATC-3 (SEQ ID NO: 16) | 5'-GTCACTGGTCAACTCCAGCAC (SEQ ID NO: 17) |
| Cidea | 5'-TGACATTCATGGGATTGCAGAC-3' (SEQ ID NO: 18) | 5'-CGAGCTGGATGTATGAGGGG-3' (SEQ ID NO: 19) |
| Fabp4 | 5'-ATCAGCGTAAATGGGGATTTGG-3' (SEQ ID NO: 20) | 5'-GTCTGCGGTGATTTCATCGAA-3' (SEQ ID NO: 21) |
| Kif5b | 5'-GCGGAGTGCAACATCAAAGTG-3' (SEQ ID NO: 22) | 5'-GATTCGTTGAGAGGTCTGAAGC-3' (SEQ ID NO: 23) |
| Lpl | 5'-TTGCCCTAAGGACCCCTGAA-3' (SEQ ID NO: 24) | 5'-ACAGAGTCTGCTAATCCAGGAAT-3' (SEQ ID NO: 25) |
| MUP1 | 5'-GAAGCTAGTTCTACGGGAAGGA-3' (SEQ ID NO: 26) | 5'-AGGCCAGGATAATAGTATGCCA-3' (SEQ ID NO: 27) |
| PPARγ | 5'-TCAGCTCTGTGGACCTCTCC-3' (SEQ ID NO: 28) | 5'-ACCCTTGCATCCTTCACAAG-3' (SEQ ID NO: [[31]]29) |
| PPARGC1α | 5'-GTCAACAGCAAAAGCCACAA-3' (SEQ ID NO: 30) | 5'-TCTGGGGTCAGAGGAAGAGA-3' (SEQ ID NO: 31) |
| PPARGC1α | 5'-TGACGTGGACGAGCTTTCAC-3' (SEQ ID NO: 32) | 5'-GGGTCTTCTTATCCTGGGTGC-3' (SEQ ID NO: 33) |
| Thrsp | 5'-ATGCAAGTGCTAACGAAACGC-3' (SEQ ID NO: 34) | 5'-AGTACCGATCCATGACTGTCAG-3' (SEQ ID NO: 35) |
| UCP1 | 5'-GGCATCCAGAGGCAAATCAG-3' (SEQ ID NO: 36) | 5'-GCATTGTAGGTCCCCGTGTA-3' (SEQ ID NO: 37) |
| Vtn | 5'-AGGCCCTTTTTCATACTAGCCC (SEQ ID NO: 38)' | 5'-AAGCTCGTCACACTGACACTT-3' (SEQ ID NO: 39) |

Samples of 25 ng cDNA were analyzed in quadruplicate in parallel with GAPDH controls. The experimental mRNA starting quantities were calculated from the standard curves and averaged using 7500 software v1.4. Experiments were performed at least three times. (*, $p\leq0.05$; **, $p\leq0.01$).

TABLE 5

| | |
|---|---|
| Acsl1- | acyl-CoA synthetase long-chain family member 1 |
| Adh7- | alcohol dehydrogenase 7 (class IV), mu or sigma polypeptide |
| AdipoQ- | adiponectin, C1Q and collagen domain containing |
| Agpat9- | 1-acylglycerol-3-phosphate O-acyltransferase 9 |
| Apoa2- | apolipoprotein A-II |
| Atp1a2- | ATPase, Na+/K+ transporting, alpha 2 polypeptide |
| CD36- | CD36 molecule (thrombospondin receptor) |
| Cebp-α- | CCAAT/enhancer binding protein (C/EBP), alpha |
| Cidea- | cell death-inducing DFFA-like effector a |
| Fabp4- | fatty acid binding protein 4, adipocyte |
| Kif5b- | kinesin family member 5B |
| Lpl- | lipase, hormone-sensitive |
| MUP1- | major urinary protein 1 |
| PPARγ- | peroxisome proliferator-activated receptor gamma |
| PPARGC1α- | peroxisome proliferator-activated receptor gamma, coactivator 1 alpha |
| PPARGC1β- | peroxisome proliferator-activated receptor gamma, coactivator 1 beta |
| Thrsp- | thyroid hormone responsive |
| UCP1- | uncoupling protein 1 (mitochondrial, proton carrier) |
| Vtn- | vitronectin | ii. Ingenuity Systems

Figure 4:
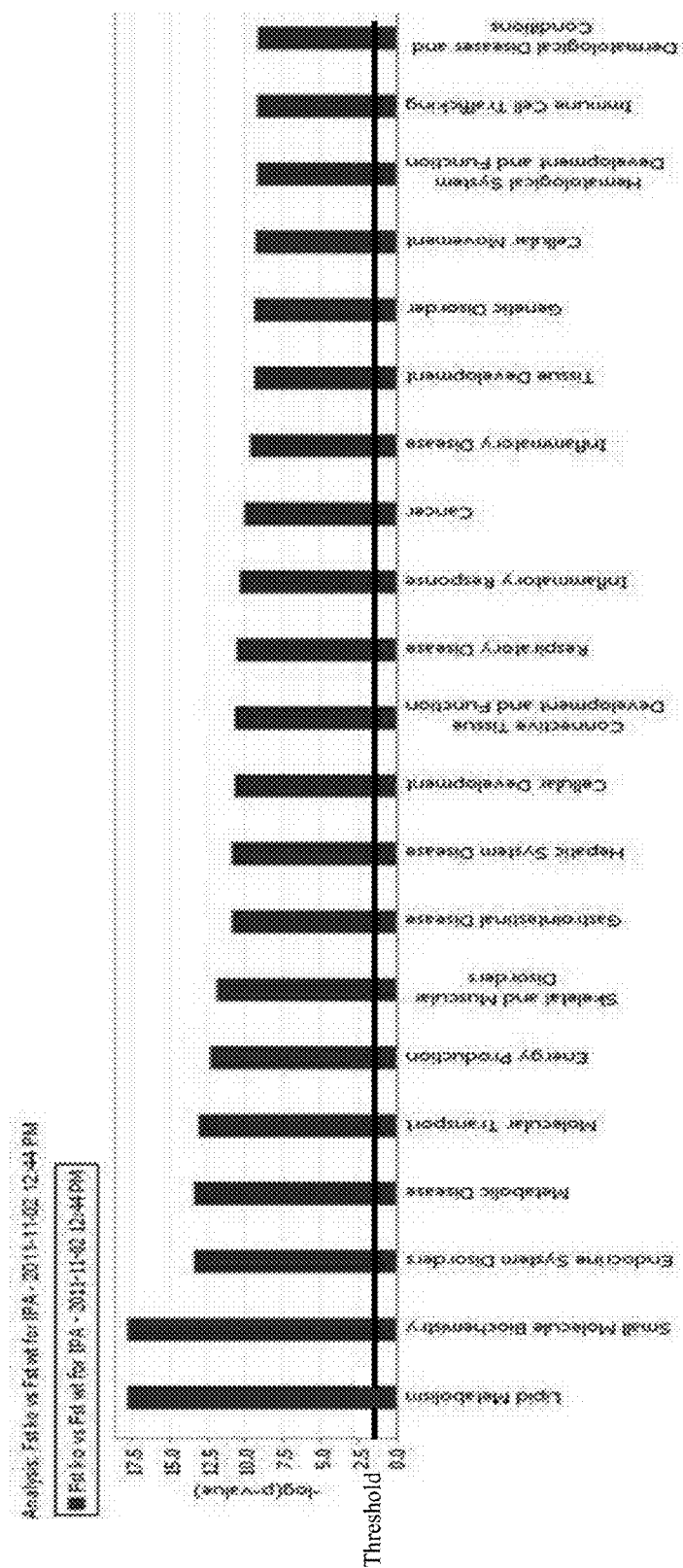
FIG. 4 shows the biological functions associated with absence of Fst as analyzed by Ingenuity Systems.

The biological functions associated with the absence of Fst were also analyzed using Ingenuity Systems. The significance of each pathway is determined based upon the p values determined using right tailed Fisher exact test and with a threshold less than 0.05. Top possible pathways of the genes regulated by Fst are shown. The ratio of number of genes in a given pathway satisfying the cutoff and total number of genes present in that pathway was determined by IPA. (FIG. 4)

iii. Immunohistochemical Analysis

Figure 5:
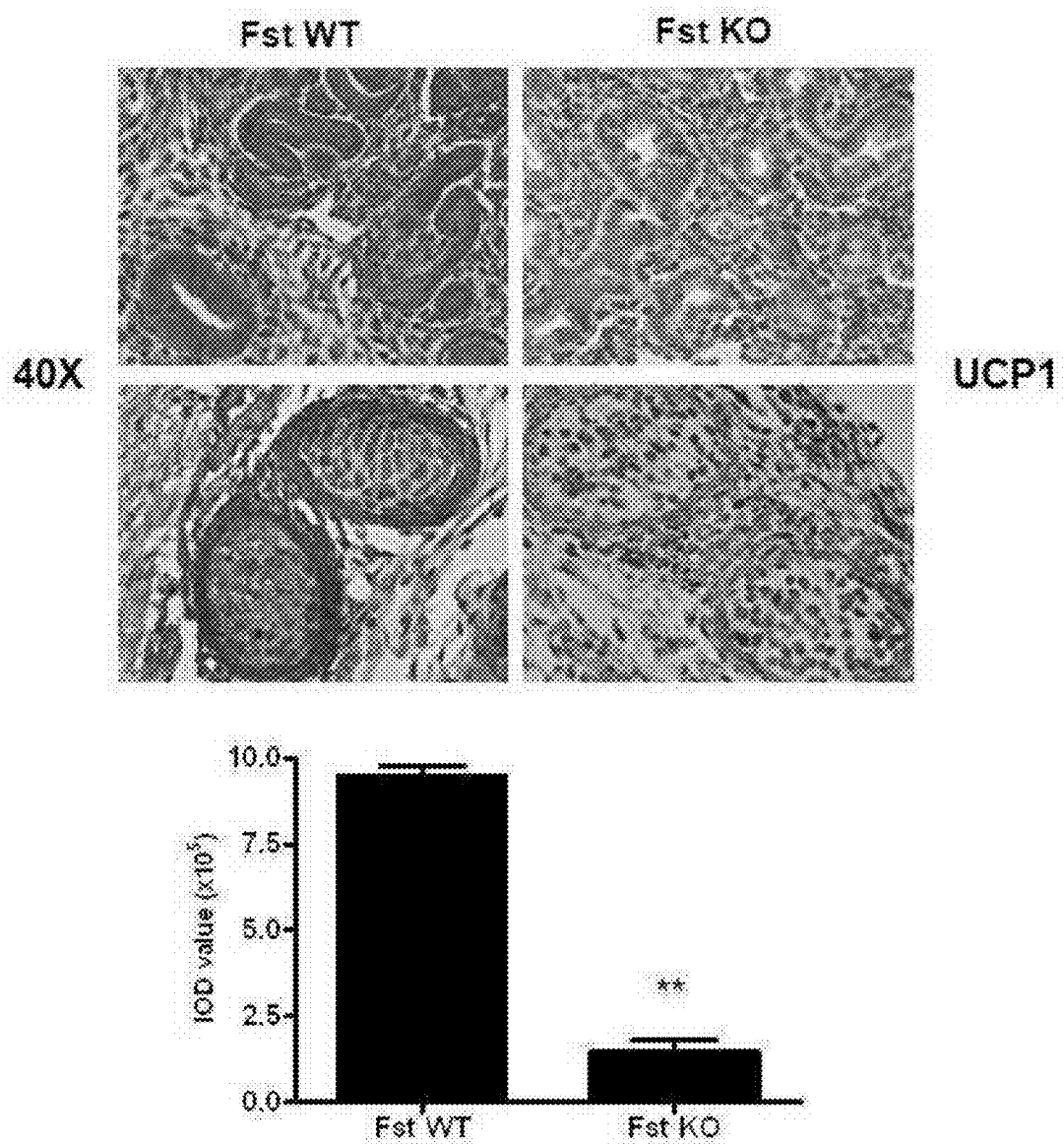
FIG. 5 shows the immunohistochemical analysis demonstrating down-regulation of UCP1 protein expression in Fst KO embryos (E13.5).

Tissue sections from formaldehyde fixed embryos (E13.5) collected from both Fst WT and Fst KO embryos were stained with anti-UCP1 antibody using standard immunohistochemical procedure. Immunostained sections were analyzed for UCP-1 immunoreactivity and quantitative analysis of represented after image analysis of 6 six different embryo sections (20 pictures each). Immunohistochemical analysis demonstrated down-regulation of UCP1 protein expression in Fst KO embryos (E13.5). (FIG. 5; **, represents $p\leq0.01$)

iv. Western Blot Analysis

Figure 6:
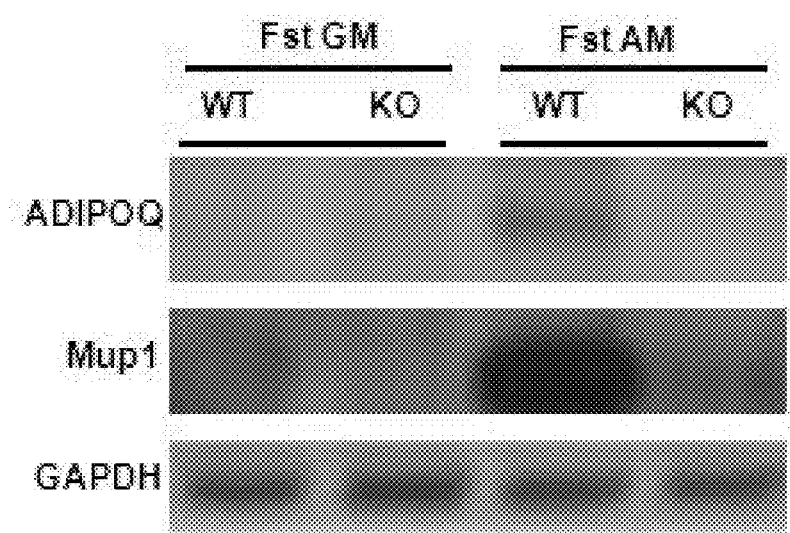
FIG. 6 shows western blot analysis demonstrating significant down-regulation of adiponectin (ADIPOQ) protein in Fst KO MEF culture undergoing adipogenic differentiation for 5 days.

Western blot analysis demonstrated significant down-regulation of adiponectin (ADIPOQ) (adipose specific gene that increases insulin sensitivity, reduces plasma free fatty acid and reported to have increased level in BAT, deregulated in obesity) and Mup1 (increases energy expenditure and improves glucose intolerance) protein in Fst KO MEF culture undergoing adipogenic differentiation for 5 days. (FIG. 6)

Recombinant Human Fst Protein Administration.

Figure 7:
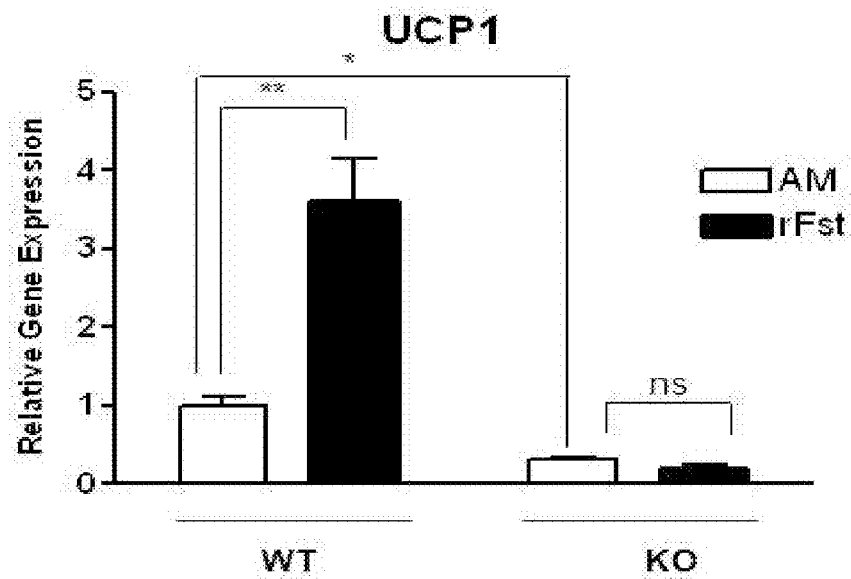
FIG. 7 shows the effect of recombinant Fst protein (0.5 µg/ml) administration on UCP-1 gene expression in MEF primary cultures from Fst WT and KO embryos undergoing adipogenic differentiation for 5 days.

Effect of recombinant Fst protein (0.5 µg/ml) administration on UCP-1 gene expression was determined in MEF primary cultures from Fst WT and KO embryos undergoing adipogenic differentiation for 5 days. Total cellular RNA obtained after treatment with recombinant Fst in both Fst WT and Fst KO groups were analyzed by quantitative real-time PCR analysis using mouse Fst and β-actin primers. Normalized data is presented in the FIG. 7. A significant difference in UCP-1 expression was observed in WT versus KO groups (* $p\leq0.05$). Also, recombinant Fst treatment significantly induced UCP-1 expression (** $p\leq0.01$) in WT, but not in Fst KO group (ns, not significant).

Figure 8:
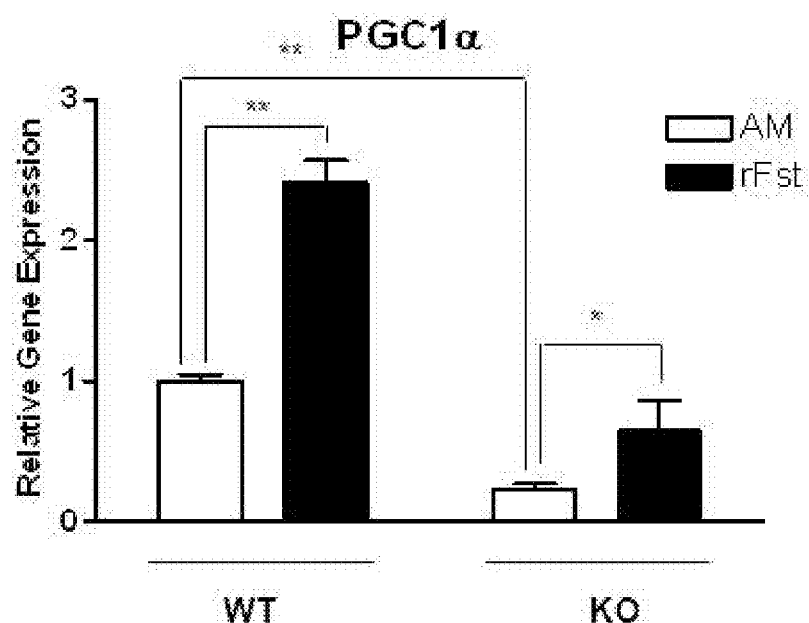
FIG. 8 shows the effect of recombinant human Fst protein (0.5 µg/ml) administration on peroxisome proliferator-activated receptor gamma, coactivator 1 alpha (PGC1-α) gene expression in MEF primary cultures from Fst WT and KO embryos undergoing adipogenic differentiation for 5 days.

The effect of recombinant human Fst protein (0.5 µg/ml) administration was also determined for peroxisome proliferator-activated receptor gamma, coactivator 1 alpha (PGC1-α) gene expression in MEF primary cultures from Fst WT and KO embryos undergoing adipogenic differentiation for 5 days. A significant difference was observed in PGC1-α expression in basal as well as Fst treated groups. (FIG. 8) Total cellular RNA obtained after treatment with recombinant Fst in both Fst WT and Fst KO groups were analyzed by quantitative real-time PCR analysis using mouse PGC1α and β-actin primers. Normalized data is presented in the FIG. 8. A significant difference was observed in PGC1α expression in WT versus KO groups ( $p\leq0.01$). Also, recombinant Fst treatment significantly induced PGC1α expression ( $p\leq0.01$) in WT, as well as in Fst KO group (* $p\leq0.05$).

Characterization of Fst KO MEFs Undergoing BAT Differentiation.

i. Oxygen Consumption Rate

Figure 9:
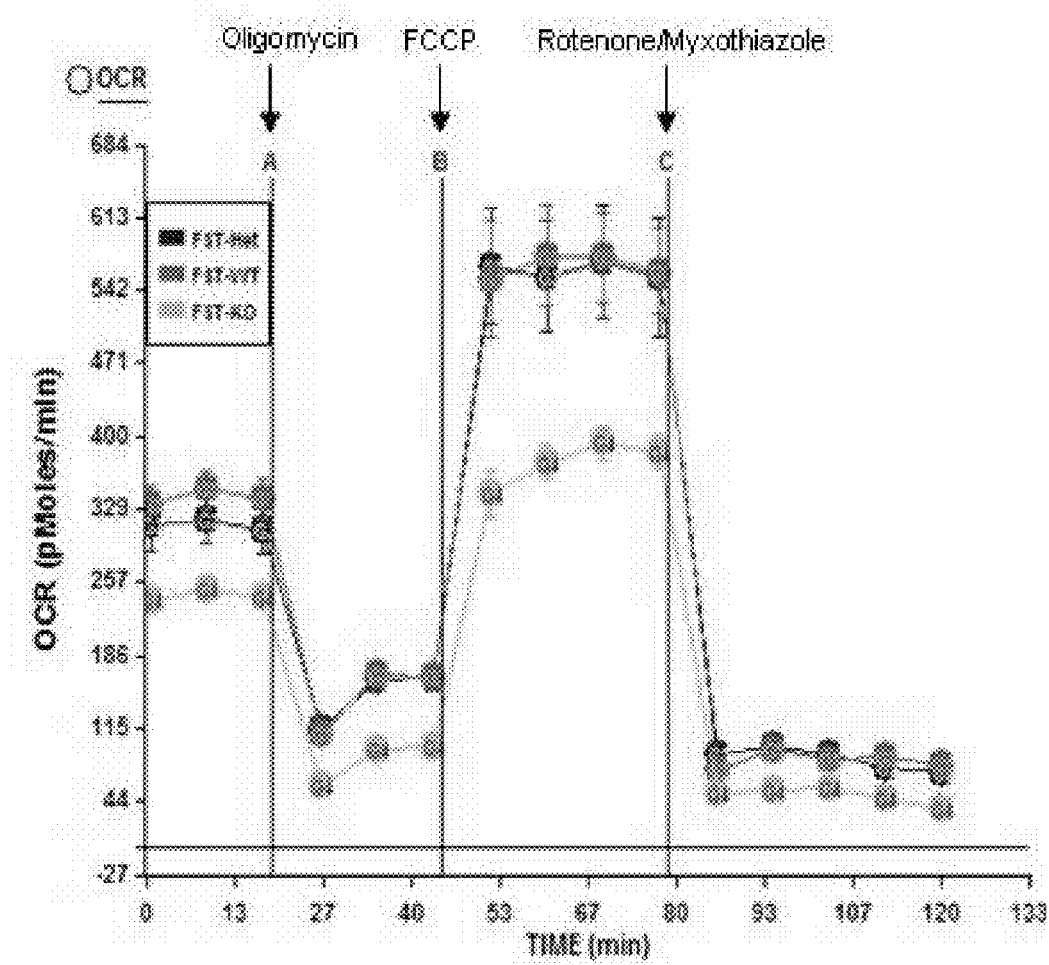
FIG. 9 shows the decrease in Oxygen consumption rate (OCR) in Fst KO MEFs undergoing BAT differentiation.

Oxygen consumption rate (OCR) in Fst KO MEFs undergoing BAT differentiation. Fst wild type (WT) (pink), heterozygote (Het) (blue), and knock out (KO) (green) MEFs undergoing BAT differentiation for 3 days were seeded on plates and allowed to further differentiate for another 24 hrs. (FIG. 9) OCR was measured using XF24 Extracellular Flux Analyzer. During experiment, 1 µM oligomycin (ATP synthase inhibitor), 1 µM carbonyl cyanide-p-trifluoromethoxy-phenylhydrazone (FCCP) (uncoupler), and a mixture of rotenone/myxothiazole (0.75 µM) (complex I and complex III inhibitor) were each subsequently injected and the response was monitored. Respiration due to oxidative phosphorylation is a measure of response to oligomycin. Maximum mitochondrial respiratory capacity is deduced from the response to FCCP treatment. A decrease in Oxygen consumption rate (OCR) was observed in Fst KO MEFs compared to Fst WT/Fst Het MEFs undergoing BAT differentiation. (FIG. 9)

ii. Induction of UCP-1 and Fst

Figure 10:
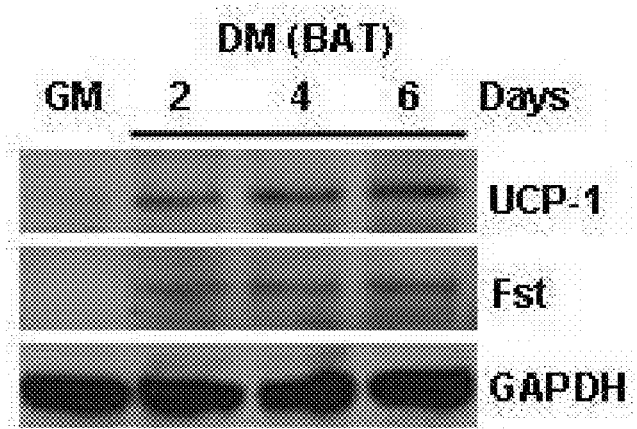
FIG. 10 shows the simultaneous induction of UCP-1 and Fst in differentiating mouse brown adipocyte cell line.

Simultaneous induction of UCP-1 and Fst was observed in a differentiating mouse brown adipocyte cell line (obtained from Dr. Bruce Spiegelman, Harvard Medical School, Boston). (FIG. 10) Adipocyte differentiation was induced by treating cells for 48 hours in medium containing 10% FBS, 0.5 mM isobuylmethylxanthine (IBMX), 125 nM indomethacin, 1 µM dexamethosone, 850 nM insulin, 1 nM T3 with 1 µM rosiglitazone (Alexis Biochemicals). After 48 hours, cells were switched to medium containing 10% FBS, 850 nM insulin, 1 nM T3 with 1 M rosiglitazone and allowed to further differentiate for additional 4 days. Cell lysates were analyzed for UCP-1 and Fst protein expression using anti-UCP-1 (Chemicon) or anti-Fst (R&D System) antibody.

Example 2—Novel Role of Follistatin in Brown Fat Differentiation and Energy Metabolism Methods Animals Male and female Fst heterozygotes (Fst+/−) mice were obtained as a kind gift from Dr. Martin Matzuk (Baylor College of Medicine). Methods for producing KO mice are disclosed, for example, in U.S. Pat. No. 6,548,738. Mice were allowed to breed and embryos from 13-13.5 day pregnant female mice were genotyped to identify Fst WT (Fst$^{+/+}$) and Fst KO (Fst$^{−/−}$) embryos for isolation of mouse embryonic fibroblast (MEF) cultures. Male Fst-Tg mice ( )

were obtained from Dr. Se-Jin Lee (Department of Molecular Biology and Genetics, Johns Hopkins Medical Center, Baltimore, Md.). Fst-Tg and WT (C57BL6J) male mice were fed either standard normal chow or high-fat chow (45 kcal % fat, Research Diets, Inc.) for 4 weeks. Muscle (levator ani and gastrocnemius), white adipose (WAT) (subcutaneous and epididymal) and interscapular BAT (iBAT) tissues were excised from 21 day old WT (Fst$^{+/+}$) and Fst-Tg male mice for analysis. All mice were housed at constant temperature (68° F.) under artificial light/dark cycle (12/12 h) and allowed to have free access to water and food. Animal experiments were approved by the Institutional Animal Care and Use and Committee (IACUC).

MEF Culture, Differentiation, and Treatment

MEFs were generated from 13.5 day post-coitum mouse embryos as described before (Braga et al. Obesity, 2012 doi: 10.1038/oby.20117). Embryos were harvested, the head, limbs, and the internal organs were removed from the embryos, and the carcasses were rinsed with 1×PBS and minced. Minced carcasses were suspended with 3 ml 0.025% trypsin/EDTA (Invitrogen) and incubated at 37° C. for 20 min. The trypsin was neutralized, after two trypsinization cycles, by adding the equal volume of cell culture media (DMEM supplemented with 10% fetal bovine serum, 20 mM glutamine, and penicillin/streptomycin). Cell suspensions were centrifuged and resuspended with cell culture media and plated out to three T-75 flasks per embryo and cultured at 37° C. with 95% air and 5% $CO_2$. When the cells are confluent, entire cells were split into four to five 100 mm dishes and cultured until confluent. For differentiation, 1-day post confluent cells (designated day 0) were treated with adipogenic differentiation medium (DM) containing 1 µM dexamethasone (Sigma Chemicals), 0.5 mM methylisobutylxanthene, 5 µg insulin/ml and 0.5 µM rosiglitazone (Sigma Chemicals) for 48 h. After 48 h, the medium was changed to maintenance medium (MM) containing 5 µg insulin/ml and 0.5 µM rosiglitazone and was changed every other day for up to day 6. MEFs isolated from Fst KO embryos were also treated with recombinant mouse Fst (0.5 µg/ml) (R&D Systems, Minneapolis, Minn.) and medium was changed every alternate day. Early passage MEFs (p≤3) was used for each experiment in order to avoid senescence.

Genotyping

Genomic DNA was isolated from the heads harvested from each embryo using Direct Lysis Reagent (Viagen Biotech, CA). Genotypes of embryos were confirmed by PCR using following primer sets—
1. 5'-ATCTATCGCCCTTGGGTCTT-3' (SEQ ID NO:40) and 5' AAAACCTACCGCAACGAATG-3' (SEQ ID NO:41), which amplifies a 152 bp fragment in WT (Fst$^{+/+}$) and heterozygous (Fst$^{+/-}$) littermates and
2. 5'-GGTGGGAAATGTCACCTGAT-3' (SEQ ID NO:42) and 5'-CGGTGGATGTGGAATGTGT-3' (SEQ ID NO:43), which amplifies a 262 bp fragment in Fst KO (Fst$^{-/-}$; WT, +/+) and heterozygous (Fst$^{+/-}$) littermates.

Genotyping of Mst embryos were performed essentially as described before (Braga et al. Obesity, 2012 doi: 10.1038/oby.20117). PCR cycle profile and the sequence of primers used for genotyping were as follows: 94° C. 1 min, 94° C. 30 sec/68° C. 30 sec-2 min for 15 times with −0.5° C. per cycle, 94° C. 30 sec and 60° C. 30 sec for 20 times (Braga et al. Obesity, 2012 doi: 10.1038/oby.20117).

Real-Time Quantitative PCR Analysis

Total RNA was extracted by using Trizol reagent, and equal amounts (2 µg) of RNA were reverse transcribed using RNA High Capacity cDNA kit (Applied Bio systems, Foster City, Calif.). The Power Sybr Green PCR master mix was used with 7500 fast real-time PCR system (Applied BioSystems). The primer pairs used are shown in Table 4 of Example 1 above. Samples of 25 ng cDNA were analyzed in quadruplicate in parallel with GAPDH controls. The experimental mRNA starting quantities were calculated from the standard curves and averaged using 7500 software v1.4 (Braga et al. Obesity, 2012 doi: 10.1038/oby.20117; Singh et al. Endocrinology. 2009; 150(3):1259-68).

Immunoblot Analysis

Proteins were resolved on 10-12% SDS-PAGE gels and then electro transferred and analyzed for protein expression using the following antibodies-anti-UCP1 (1:1000 dilution, Abcam, Mass.); anti-UCP2 (1:1000 dilution, Millipore, Mass.); anti-UCP3 (1:1000 dilution, Abcam, Mass.); anti-PRDM16 (1:300 dilution, Santa Cruz Biotechnology, CA), anti-PGC-1α and anti-Mup1 (1:1000 dilution, Santa Cruz Biotech, Calif.); anti-AP2 (FABP4) (1:500 dilution, Santa Cruz Biotechnology, CA); anti-AdipoQ (1:1000 dilutions, Millipore); anti-AMPK/anti-pAMPK (1:1000 dilutions, Cell Signaling, MA) or anti-GAPDH antibody (1:5,000 dilutions, Chemicon International, Temecula, Calif.) with appropriate HRP-linked to secondary antibodies (1:1000 dilution) (Cell Signaling, MA). Immuno-reactive bands were visualized, scanned and analyzed by Image Quant software (Braga et al. Obesity, 2012 doi: 10.1038/oby.20117; Singh et al. Endocrinology. 2009; 150(3):1259-68).

Immunohistochemical Analysis

Embryo and tissue sections were fixed overnight in formalin, embedded with paraffin blocks and sectioned. Tissue sections were stained with hematoxilin/eosin or with anti-UCP1 antibody following standard procedures. Quantitative image analysis (QIA) was performed by computerized densitometry using the ImagePro 4.01 program (Media Cybernetics, Silver Spring, Md., USA), coupled to an Leica B microscope equipped with an Spot RT digital camera (Diagnostic Instruments, Portland, Oreg., USA) (Braga et al. Obesity, 2012 doi: 10.1038/oby.20117; Singh et al. Endocrinology. 2009; 150(3): 1259-68).

Affymetrix Analysis

Global gene expression microarray studies utilizing Affymetrix U133 Plus 2.0 array (Affymetrix, Santa Clara, Calif.) was performed in collaboration with the UCLA Clinical Microarray Core. Total RNA was extracted from Fst WT and Fst KO MEFs differentiating under BAT conditions using TRIzol (Life Technologies, NY, USA) followed by Qiagen column purification (Qiagen, Valencia, Calif., USA). RNA integrity was evaluated by an Agilent 2100 Bioanalyzer (Agilent Technologies; Palo Alto, Calif.) and purity and concentration were determined by NanoDrop 8000 (NanoDrop, Wilmington, Del., USA). Subsequent data analyses were performed using Partek Genomics Suite with the CEL files obtained from GCOS. The data was normalized using RMA algorism. Changes in gene expression (>=3.5 fold) of key genes involved in lipid and energy metabolism were further validated with quantitative real-time PCR analysis (Koh et al. Mod Pathol. 2012 Mar. 9. doi: 10.1038/modpathol; Donahue et al. Clin Cancer Res. 2012; 18(5):1352-63).

Analysis of Cellular Oxygen Consumption

Oxygen consumption rates (OCR) of differentiating MEFs were measured in a Seahorse Bioscience XF24 Extracellular Flux Analyzer (North Billerica, Mass., USA) (Vergnes et al. J Biol Chem. 2011; 286(1):380-90; Chao et al. Diabetes. 2009; 58(12):2788-96). Undifferentiated MEFs were seeded with 4×10$^4$ cells per well in DMEM containing 10% FBS and incubated overnight at 37° C. with 5% $CO_2$.

MEF differentiation was performed for 2 days. Medium was replaced by DMEM supplemented with 25 mM glucose, 2 mM L-glutamine and 2% FBS and cells were incubated at 37° C. in a $CO_2$-free incubator for 1 hr. Oxygen consumption was recorded for 25 min. During this experiment, 1 µM oligomycin, 0.5 µM carbonyl cyanide-p-trifluoromethoxyphenylhydrazone (FCCP), and a mixture of 100 nM rotenone and myxothiazol each was sequentially injected and the response was monitored. Basal mitochondrial respiration was calculated by subtracting the respiration after rotenone/myxothiazol (complex I and complex III inhibitor) injection from the levels observed before any chemical treatments. Respiration due to oxidative phosphorylation was calculated as the response to oligomycin (ATP synthase inhibitor). Maximal mitochondrial respiratory capacity was deduced from the response to treatment with FCCP (mitochondrial uncoupler) (Vergnes et al. J Biol Chem. 2011; 286(1):380-90; Chao et al. Diabetes. 2009; 58(12):2788-96).

CT Scan

Mice received isoflurane (2% by inhalation) anesthesia before imaging in a MicroCAT II small animal CT system (Siemens Preclinical Solutions, Knoxville, Tenn., USA), as described previously (Suckow et al. Mol Imaging Biol. 2009; 11(2):100-6; Suckow et al. Mol Imaging Biol. 2008; 10(2):114-20). A heated anesthesia chamber was used to maintain body temperature and mice were positioned in the center of the field of view. Exposure settings were 70 kVp, 500 mAs, 500 ms exposure time, and 360° rotation in 1° steps with 2.0 mm aluminum filtration. Images were reconstructed using a modified Feldkamp process to a cubic voxel size of 0.20 mm in a 256×256×496 matrix. CT values were converted into Hounsfield units using the formula: $HU = (\mu_t - \mu_w)/(\mu_w - \mu_a) \times 1000$ where $\mu_w$ and $\mu_a$ are the linear attenuation coefficients of water and air, respectively, and $\mu_t$ is the linear attenuation coefficient of tissue. Using the freely available software AMIDE (http://amide.sourceforge.net/), images were analyzed to separate fat (low density) from other soft tissues based on Hounsfield units. The imaging chamber was removed from the CT images using elliptic cylinder region of interest (ROI). The mouse abdominal region was selected from the liver/lung interface to the top of the pelvic horn. An isocontour value selection above −350 Hounsfield units was used to determine the region volume. Adipose tissue volume was selected using isocontour value selection between −268 and −48. Separation of visceral and subcutaneous fat was performed in draw mode by editing the adipose region to contain only one fat type. ROI volumes were calculated using AMIDE and converted to mass assuming an average density of 1.0 g/cm$^3$.

Glucose Tolerance Test

Four weeks old male WT and Fst-Tg mice were allowed to fast overnight and anesthetized with an intraperitoneal (ip) injection of sodium pentobarbitone (100 mg/kg). A silastic catheter filled with heparinized saline (20 u/ml) was inserted into left carotid artery. A bolus of glucose (2 mg/g body weight) was injected into the intraperitoneal cavity. 200 µl of blood was collected at 0, 30, 60, 120, 180, and 240 minutes for plasma glucose (Glucometer Elite; Bayer Diagnostics) analysis (Ortega-Molina et al. Cell Metab. 2012; 15(3):382-94; Morgantini et al. Diabetes. 2010; 59(12): 3223-8; Imaizumi et al. Mol Genet Metab. 2010; 101(1): 66-75).

Serum Analysis

Serum levels of triglycerides (TG), free fatty acid (FFA), total cholesterol, HDL and insulin were analyzed by ELISA (Mercodia, Alpco and Invitrogen) (Morgantini et al. Diabetes. 2010; 59(12):3223-8; Imaizumi et al. Mol Genet Metab. 2010; 101(1):66-75).

Statistical Analysis

Data are presented as mean+/−SD, and between group differences were analyzed by ANOVA using GraphPad Prism Version 5.3 (GraphPad Software, San Diego, Calif.). If the overall ANOVA revealed significant differences, then pair-wise comparisons between groups were performed by Newman-Keuls multiple group test. All comparisons were two-tailed and p values ≤0.05 were considered statistically significant. The experiments were repeated at least three times, and data from representative experiments are shown.

Results

Figure 11A:
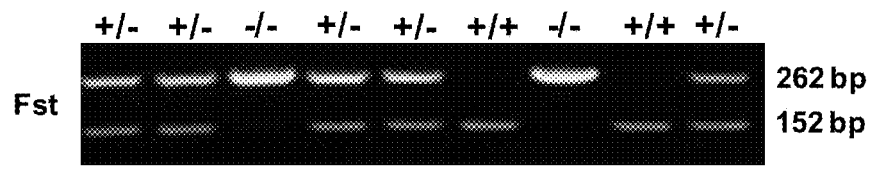
FIG. 11 shows the inhibition of key BAT differentiation markers in differentiating Fst KO MEF cultures compared to the Fst WT group. (A) Genotypic isolation of Fst WT (+/+), and Fst KO (−/−) embryos from day 14 pregnant mice. (B) Real-time qPCR analysis confirming the absence of Fst expression in primary culture of Fst KO MEFs. (C-D) Western blot and densitometric analysis of key proteins expressed in BAT (E) IHC staining (left panel) and quantitative image analysis (right panel) of Fst WT and Fst KO embryo (day 14) sections using UCP1 antibody. IOD, integrated optical density. Experiments were conducted in triplicate. Data are expressed as mean±SD. *, $p \leq 0.05$, **, $p \leq 0.01$.
Figure 11B:
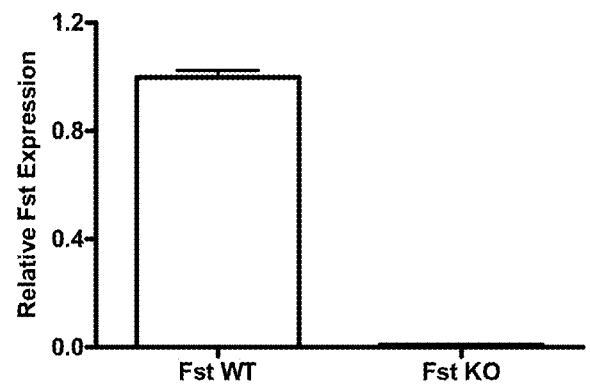
Figure 11C:
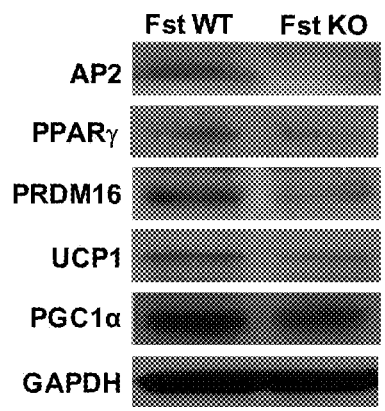
Figure 11D:
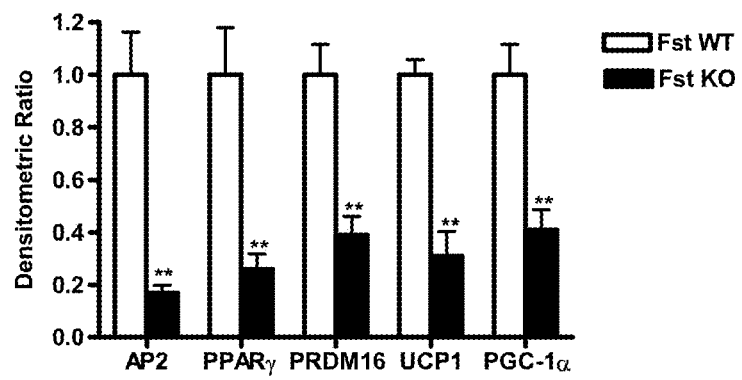
Figure 11E:
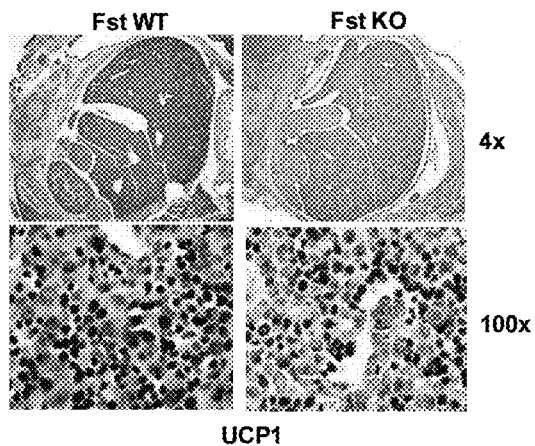
Figure 11E:
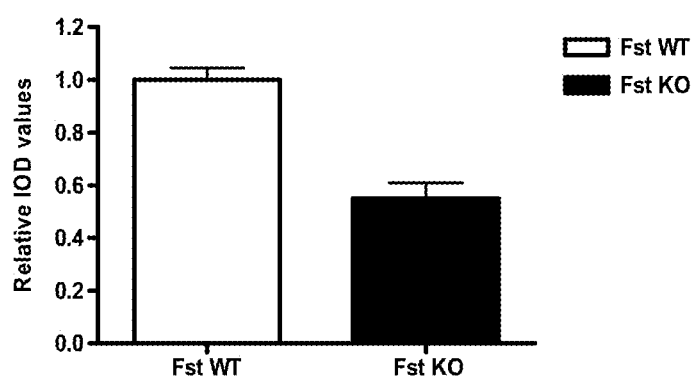

Loss of Fst in Fst KO MEFs and Embryos Results in Significant Down-Regulation of Brown-Fat Markers Compared to the Fst WT MEFs Since Fst KO pups die just after birth, we utilized MEF-based approach to identify Fst KO (−/−) and Fst WT (+/+) embryos to study the specific role of Fst during BAT differentiation and regulation of thermogenic program. Fst WT and Fst KO embryos were separated after genotyping from day 14 pregnant Fst heterozygous (+/−) female mice mated with Fst heterozygous (+/−) male mice (FIG. 11A). Absence of Fst mRNA expression in Fst KO embryos was confirmed by quantitative real-time PCR (FIG. 11B). Analysis of adipose-specific proteins in differentiating Fst KO MEFs suggest a significant down-regulation of fatty acid binding protein 2 (FABP2 or AP2) (83.3±4.1%) and PPARγ (74.6±8.2%) proteins compared to the Fst WT MEFs. These proteins are expressed in both WAT and BAT. We also found significant down-regulation of key BAT-specific proteins PRDM16 (61.3±11.2%); UCP1 (69.2±10.7%); and PGC-1α (59.5±8.5%) in Fst KO MEFs compared to the Fst WT MEFs (FIG. 11C-D). Further analysis of UCP1 expression in day 14 pregnant embryos by quantitative immunohistochemistry (IHC) demonstrated immuno-positive cells at various parts of the embryos at different levels. We focused our analysis at section, where UCP1 expression was prominent in Fst WT embryos. Overall UCP1 expression in Fst KO embryos was significantly lower (45.4±6.7%) compared to the Fst WT embryos (FIG. 11E).

Figure 12A:
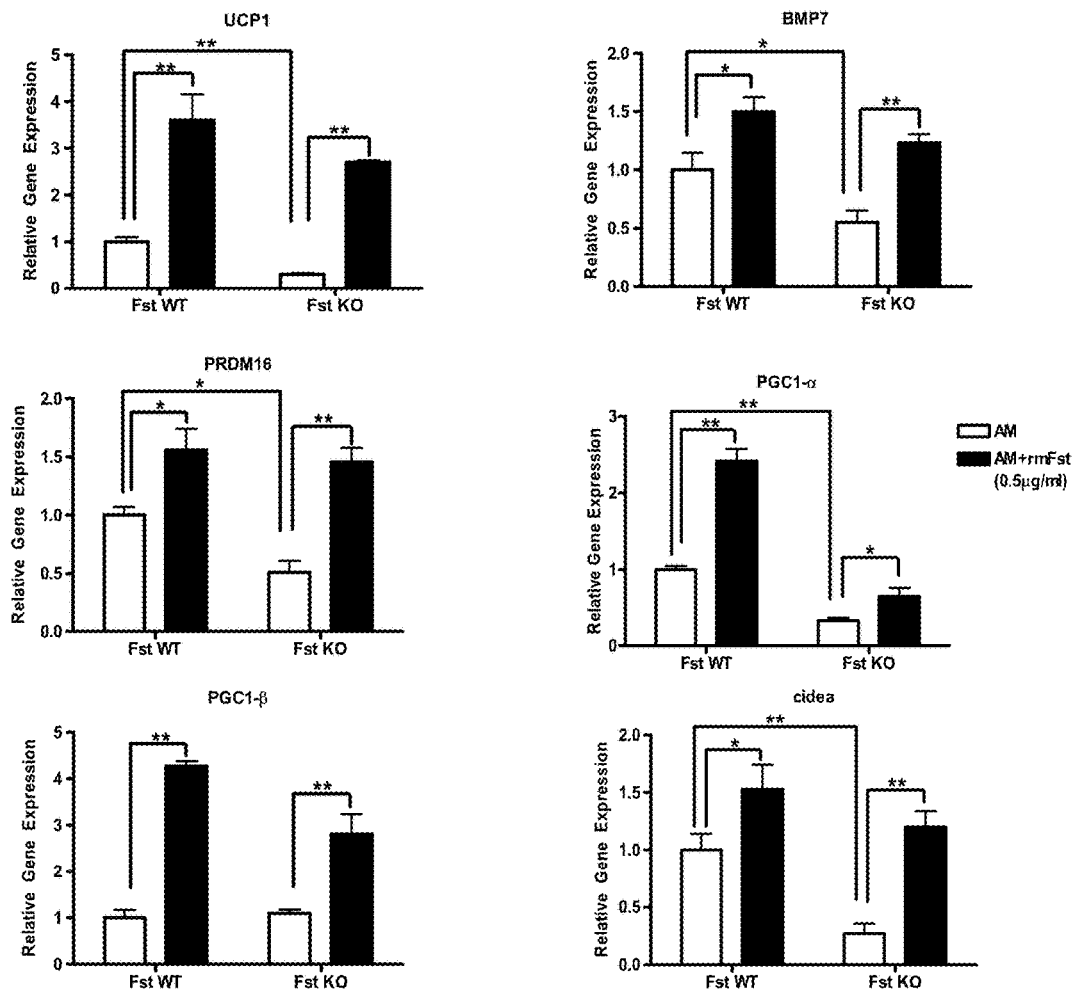
FIG. 12 shows the induction of key BAT-specific genes and proteins in differentiating Fst WT and Fst KO MEF cultures by recombinant Fst. (A) Real-time qPCR analysis in MEF cultures after treatment with recombinant Fst (0.5 µg/ml) protein after 4 days. (B-C) Western blot and densitometric analysis of PRDM16, UCP1 and PGC-1α proteins in differentiating MEF cultures from Fst WT and Fst KO groups. Experiments were conducted in triplicate. Data are expressed as mean±SD. *, $p \leq 0.05$, **, $p \leq 0.01$. (D) Ingenuity pathway analysis (IPA) demonstrating lipid metabolism as the most significantly altered pathway between Fst WT vs. Fst KO groups.
Figure 12B:
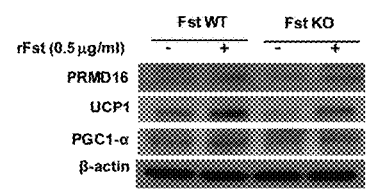
Figure 12C:
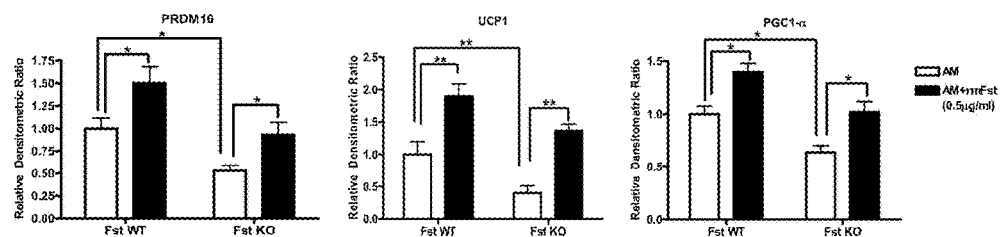

Recombinant Fst Treatment Significantly Upregulated BAT-Specific Genes and Proteins in Both Fst WT and Fst KO MEF Cultures We analyzed the expression profile of several key BAT-specific genes and proteins in both Fst WT and Fst KO cultures after treatment with recombinant Fst (0.5 µg/ml) proteins for 4 days. We found that Fst treatment led to significant increase in several BAT-specific genes including UCP1 (WT: 3.6±1.1 fold; KO:8.6±0.5 fold); PRDM16 (WT: 1.46±0.36 fold; KO:2.8±0.13 fold); PGC-13 (4.27±0.21 fold; KO: 2.57±0.64 fold); BMP7 (WT:1.5±0.24 fold; KO: 2.24±0.16 fold); PGC-1α (WT: 4.27±0.21 fold; KO:2.6±0.15 fold); and cidea (WT:1.53±0.37 fold; KO: 1.7±0.18 fold) (FIG. 12A). We also found a significant induction of protein expression of PRDM16 (WT: 1.5±0.32 fold; KO: 1.75±0.24 fold); UCP1 (WT: 1.9±0.33 fold; KO: 3.4±0.17 fold) and PGC-1a (WT: 1.4±0.14 fold; KO: 1.59±0.17 fold) after treatment of differentiating MEFs with recombinant Fst (0.5 µg/ml) for 4 days (FIG. 12B-C).

Figure 12D:
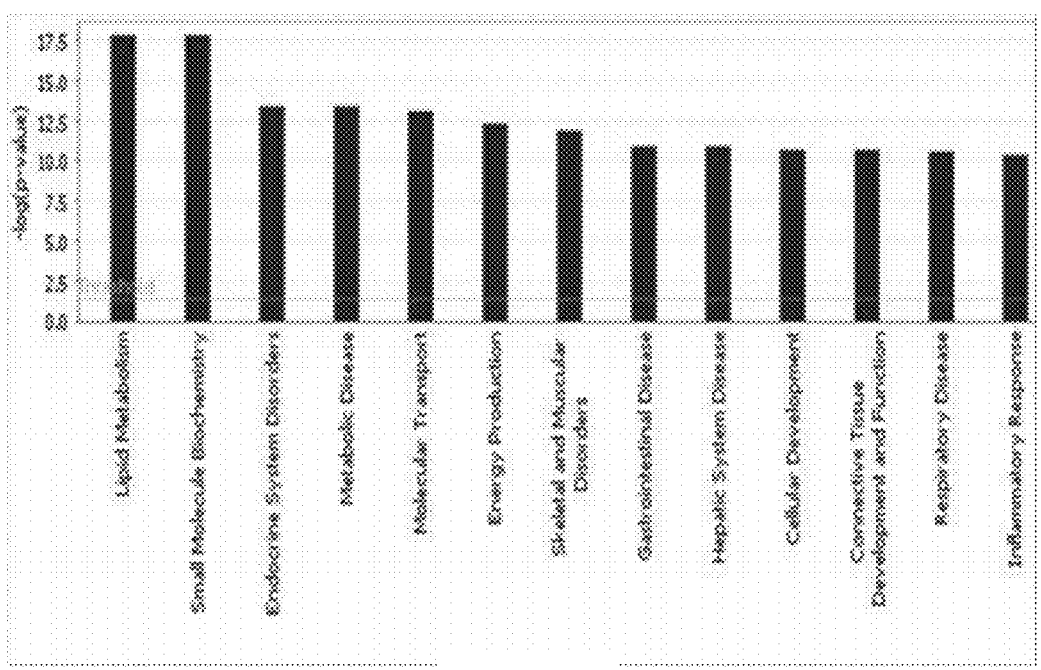
Figure 13A:
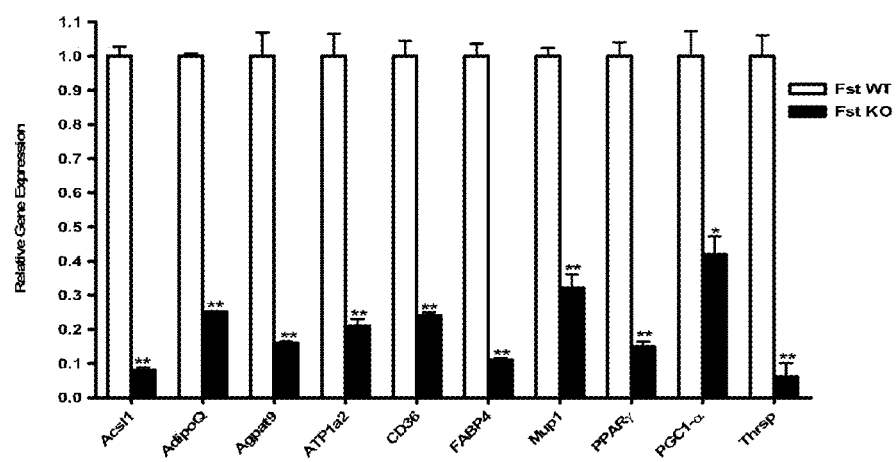
FIG. 13 shows the validation of Affymetrix gene expression analysis by (A) qPCR using gene-specific primers and (B) Western blot analysis of Mup1 and adiponectin (AdipoQ) in primary cultures of MEFs allowed to grow either under normal growth condition in GM (growth medium) or under BAT-specific differentiation condition in BAT DM (differentiation medium). Experiments were conducted in triplicate. Data are expressed as mean±SD. *, $p \leq 0.05$, **, $p \leq 0.01$.

Global Gene Expression Profiling Displays a Significant Inhibition of Key Genes Involved in Overall Lipid and Energy Metabolism in Fst KO MEFs Compared to the Fst WT MEF Cultures Based on our initial findings that Fst loss-of function results in down-regulation of key BAT-specific genes and proteins, we performed Affymetrix global gene expression profiling of Fst WT and Fst KO MEFs differentiating under BAT-specific conditions for 48 hrs. The most prominent changes between the groups as suggested by Ingenuity Pathway Analysis (IPA) were found to be the lipid and energy production pathways (FIG. 12D). We validated the findings from Affymetrix analysis (Table 6) by performing quantitative real-time PCR analysis using gene specific primers (FIG. 13A).

TABLE 6

Down-regulation of energy production and lipid metabolism genes in Fst KO MEFs

| Symbol | Entrez Gene Name | Fst KO vs. Fst WT (fold change) |
| --- | --- | --- |
| ACSL1 | acyl-CoA synthetase long-chain family member 1 | −9.0 |
| ADIPOQ | adiponectin, C1Q and collagen domain containing | −36.7 |
| AGPAT9 | 1-acylglycerol-3-phosphate O-acyltransferase 9 | −4.8 |
| APOC2 | apolipoprotein C-II | −4.2 |
| ATP1A2 | ATPase, Na+/K+ transporting, alpha 2 polypeptide | −4.2 |
| CD36 | CD36 molecule (thrombospondin receptor) | −3.9 |
| CPS1 | carbamoyl-phosphate synthase 1, mitochondrial | −4.0 |
| FABP4 | fatty acid binding protein 4, adipocyte | −6.3 |
| HP | haptoglobin | −10.1 |
| MUP1 | major urinary protein 1 | −3.9 |
| PLG | plasminogen | −4.8 |
| PPARG | peroxisome proliferator-activated receptor gamma | −4.7 |
| SAA1 | Serum amyloid A1 | −4.1 |
| SERPINA1 | serpin peptidase inhibitor, clade A (alpha-1 antiproteinase, antitrypsin), member 1 | −3.6 |
| THRSP | thyroid hormone responsive | −11.7 |

Table 6 demonstrates the down-regulation of energy production and lipid metabolism related genes in differentiating Fst KO MEF cultures compared to the Fst WT group. Cells were allowed to differentiate under BAT-specific condition as described in Material and Methods and Affymetrix gene expression analysis was performed. Changes in energy production and lipid metabolism specific genes that were above 3.5 fold were selected. We found significant down-regulation of Acsl1 (12.5±0.7 fold); adiponectin (AdioQ) (4.0±0.2 fold); Agpat9 (6.25±0.2 fold); CD36 (4.17±0.21 fold); FABP4 (9.1±0.2 fold); Mup1 (3.12±0.32 fold); PPARγ (6.67±0.38 fold) and Thrsp (16.6±1.7 fold) along with several other relevant genes in Fst KO compared to Fst WT MEF cultures (FIG. 13A). Several other differentially expressed genes involved in lipid and energy metabolism between the groups (with changes less than 3.5 fold but higher than 1.5 fold) are shown in Table 7.

TABLE 7

| Symbol | LIPID METABOLISM AND ENERGY PRODUCTION Entrez Gene Name | Fst KO vs Fst WT Fold Change |
| --- | --- | --- |
| A130040M12Rik | RIKEN cDNA A130040M12 gene | −1.861 |
| ABCB1 | ATP-binding cassette, sub-family B (MDR/TAP), member 1 | −1.588 |
| ABCD2 | ATP-binding cassette, sub-family D (ALD), member 2 | −1.916 |
| ABHD5 | abhydrolase domain containing 5 | −1.556 |
| ACE | angiotensin I converting enzyme (peptidyl-dipeptidase A) 1 | −1.697 |
| ACLY | ATP citrate lyase | 1.529 |
| ADH7 | alcohol dehydrogenase 7 (class IV), mu or sigma polypeptide | −1.876 |
| ADH1C | alcohol dehydrogenase 1C (class I), gamma polypeptide | −1.807 |
| AFP | alpha-fetoprotein | −2.829 |
| AGPAT2 | 1-acylglycerol-3-phosphate O-acyltransferase 2 (lysophosphatidic acid acyltransferase, beta) | −2.327 |
| AGT | angiotensinogen (serpin peptidase inhibitor, clade A, member 8) | −2.597 |
| ALDOB | aldolase B, fructose-bisphosphate | −1.634 |
| ALB | albumin | −2.854 |
| AMBP | alpha-1-microglobulin/bikunin precursor | −2.955 |
| ANG | angiogenin, ribonuclease, RNase A family, 5 | 3.004 |
| ANGPTL4 | angiopoietin-like 4 | −2.405 |

TABLE 7-continued

| Symbol | LIPID METABOLISM AND ENERGY PRODUCTION Entrez Gene Name | Fst KO vs Fst WT Fold Change |
|---|---|---|
| APOA1 | apolipoprotein A-I | −3.189 |
| APOA2 | apolipoprotein A-II | −2.810 |
| APOC1 | apolipoprotein C-I | −3.153 |
| APOD | apolipoprotein D | −1.715 |
| APOE | apolipoprotein E | −1.671 |
| APOH | apolipoprotein H (beta-2-glycoprotein I) | −1.971 |
| ASPG | asparaginase homolog (S. cerevisiae) | −1.682 |
| C3 | complement component 3 | −3.743 |
| CAV2 | caveolin 2 | −1.584 |
| CCL2 | chemokine (C—C motif) ligand 2 | −1.503 |
| CCL11 | chemokine (C—C motif) ligand 11 | −2.725 |
| CD7 | CD7 molecule | 1.540 |
| CD14 | CD14 molecule | −1.535 |
| CEBPA | CCAAT/enhancer binding protein (C/EBP), alpha | −2.151 |
| CIDEA | cell death-inducing DFFA-like effector a | −2.615 |
| CIDEC | cell death-inducing DFFA-like effector c | −2.418 |
| CLEC11A | C-type lectin domain family 11, member A | 1.697 |
| CP | ceruloplasmin (ferroxidase) | −2.269 |
| CSF1R | colony stimulating factor 1 receptor | −1.520 |
| CYB5A | cytochrome b5 type A (microsomal) | −1.601 |
| CYP11B1 | cytochrome P450, family 11, subfamily B, polypeptide 1 | −1.621 |
| CYP2F1 | cytochrome P450, family 2, subfamily F, polypeptide 1 | −1.545 |
| CYP2J2 | cytochrome P450, family 2, subfamily J, polypeptide 2 | −1.563 |
| CYP3A4 | cytochrome P450, family 3, subfamily A, polypeptide 4 | −3.377 |
| CYP3A43 | cytochrome P450, family 3, subfamily A, polypeptide 43 | −2.888 |
| CYP7B1 | cytochrome P450, family 7, subfamily B, polypeptide 1 | −1.798 |
| DGAT2 | diacylglycerol O-acyltransferase 2 | −2.645 |
| DKK1 | dickkopf homolog 1 (Xenopus laevis) | 1.541 |
| DRD1 | dopamine receptor D1 | −1.597 |
| DSP | desmoplakin | 1.519 |
| ELOVL2 | ELOVL fatty acid elongase 2 | −2.693 |
| ENPP2 | ectonucleotide pyrophosphatase/phosphodiesterase 2 | −1.549 |
| EPAS1 | endothelial PAS domain protein 1 | −1.615 |
| EPHX2 | epoxide hydrolase 2, cytoplasmic | −1.739 |
| F2 | coagulation factor II (thrombin) | −1.822 |
| FABP1 | fatty acid binding protein 1, liver | −2.549 |
| FCGR2A | Fc fragment of IgG, low affinity IIa, receptor (CD32) | −1.642 |
| Fcrls | Fc receptor-like S, scavenger receptor | 1.506 |
| FGF9 | fibroblast growth factor 9 (glia-activating factor) | 1.603 |
| FOXO4 | forkhead box O4 | 1.565 |
| FMO1 | flavin containing monooxygenase 1 | −1.581 |
| FMO2 | flavin containing monooxygenase 2 (non-functional) | −1.635 |
| G6PC | glucose-6-phosphatase, catalytic subunit | −1.576 |
| GFRA2 | GDNF family receptor alpha 2 | −1.793 |
| GPD1 | glycerol-3-phosphate dehydrogenase 1 (soluble) | −3.453 |
| HPGD | hydroxyprostaglandin dehydrogenase 15-(NAD) | −1.740 |
| HPX | hemopexin | −2.628 |
| HSD3B2 | hydroxy-delta-5-steroid dehydrogenase, 3 beta- and steroid delta-isomerase 2 | −1.693 |
| IL1R1 | interleukin 1 receptor, type I | −1.629 |
| KITLG | KIT ligand | −2.049 |
| KLF2 | Kruppel-like factor 2 (lung) | 1.518 |
| LECT1 | leukocyte cell derived chemotaxin 1 | −3.351 |
| LIPE | lipase, hormone-sensitive | −2.595 |
| LIPH | lipase, member H | −1.642 |
| LPL | lipoprotein lipase | −2.548 |
| MAOB | monoamine oxidase B | −1.517 |
| MGST2 | microsomal glutathione S-transferase 2 | −1.793 |
| MLXIPL | MLX interacting protein-like | −1.915 |
| MTMR7 | myotubularin related protein 7 | 1.624 |
| NAMPT | nicotinamide phosphoribosyltransferase | −1.576 |
| NPPA | natriuretic peptide A | 3.233 |
| Nppb | natriuretic peptide type B | 1.520 |
| NUDT7 | nudix (nucleoside diphosphate linked moiety X)-type motif 7 | −1.522 |
| PCK1 | phosphoenolpyruvate carboxykinase 1 (soluble) | −2.481 |
| PCSK9 | proprotein convertase subtilisin/kexin type 9 | −1.543 |
| PDE8B | phosphodiesterase 8B | 1.592 |
| PDPN | podoplanin | 1.868 |
| PLA1A | phospholipase A1 member A | −1.824 |
| PLA2G16 | phospholipase A2, group XVI | −1.964 |
| PLIN2 | perilipin 2 | −1.578 |
| PNPLA2 | patatin-like phospholipase domain containing 2 | −2.022 |
| PNPLA3 | patatin-like phospholipase domain containing 3 | −2.172 |
| PPARGC1A | peroxisome proliferator-activated receptor gamma, coactivator 1 alpha | −2.164 |
| PPARGC1B | peroxisome proliferator-activated receptor gamma, coactivator 1 beta | −1.702 |
| PRKAR2B | protein kinase, cAMP-dependent, regulatory, type II, beta | −1.709 |

TABLE 7-continued

| Symbol | LIPID METABOLISM AND ENERGY PRODUCTION Entrez Gene Name | Fst KO vs Fst WT Fold Change |
|---|---|---|
| PRLR | prolactin receptor | −2.029 |
| PTGDS | prostaglandin D2 synthase 21 kDa (brain) | −1.914 |
| PTGIS | prostaglandin I2 (prostacyclin) synthase | 1.506 |
| RARRES2 | retinoic acid receptor responder (tazarotene induced) 2 | −2.419 |
| RDH12 | retinol dehydrogenase 12 (all-trans/9-cis/11-cis) | −2.360 |
| RETN | resistin | −1.784 |
| SCAP | SREBF chaperone | 1.500 |
| SCD | stearoyl-CoA desaturase (delta-9-desaturase) | −1.773 |
| SCHIP1 | schwannomin interacting protein 1 | 1.671 |
| SERINC2 | serine incorporator 2 | 2.085 |
| SERPINA6 | serpin peptidase inhibitor, clade A (alpha-1 antiproteinase, antitrypsin), member 6 | −1.790 |
| SLPI | secretory leukocyte peptidase inhibitor | −1.824 |
| SNCA | synuclein, alpha (non A4 component of amyloid precursor) | 1.595 |
| STAR | steroidogenic acute regulatory protein | −1.808 |
| STARD4 | StAR-related lipid transfer (START) domain containing 4 | −1.567 |
| SULT1A1 | sulfotransferase family, cytosolic, 1A, phenol-preferring, member 1 | −1.627 |
| TLR4 | toll-like receptor 4 | −1.546 |
| TNXB | tenascin XB | −1.936 |
| TTPA | tocopherol (alpha) transfer protein | −2.235 |
| TTR | transthyretin | −2.060 |
| UCP1 | uncoupling protein 1 (mitochondrial, proton carrier) | −2.850 |
| UCP2 | uncoupling protein 2 (mitochondrial, proton carrier) | −2.255 |
| UGT1A1 | UDP glucuronosyltransferase 1 family, polypeptide A1 | −1.555 |
| UGT2B10 | UDP glucuronosyltransferase 2 family, polypeptide B10 | −1.730 |
| VTN | vitronectin | −2.332 |
| XDH | xanthine dehydrogenase | −2.285 |

Figure 13B:
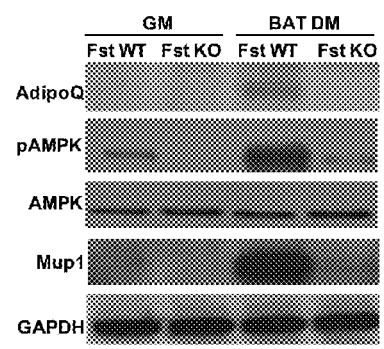

Table 7 demonstrates the down-regulation of energy production and lipid metabolism related genes in differentiating Fst KO MEF cultures compared to the Fst WT group. Cells were allowed to differentiate under BAT-specific condition as described in Material and Methods and Affymetrix gene expression analysis was performed. Changes in energy production and lipid metabolism specific genes that were above 1.5 fold were selected. We also simultaneously analyzed the protein expression of AdipoQ, AMPK/pAMPK and Mup1 in Fst WT and Fst KO MEF cultures under both growth (GM) and BAT-specific differentiation (BAT DM) conditions. While AdipoQ and Mup1 protein expression in both Fst WT and Fst KO cultures were barely detectable under growth conditions, we found a clear inhibition of their expression in Fst KO cultures relative to WT under BAT-specific differentiation conditions (FIG. 13B). Differentiating Fst KO MEFs also had down-regulation of pAMPK expression compared to the Fst WT MEFs (FIG. 13B).

Figure 14A:
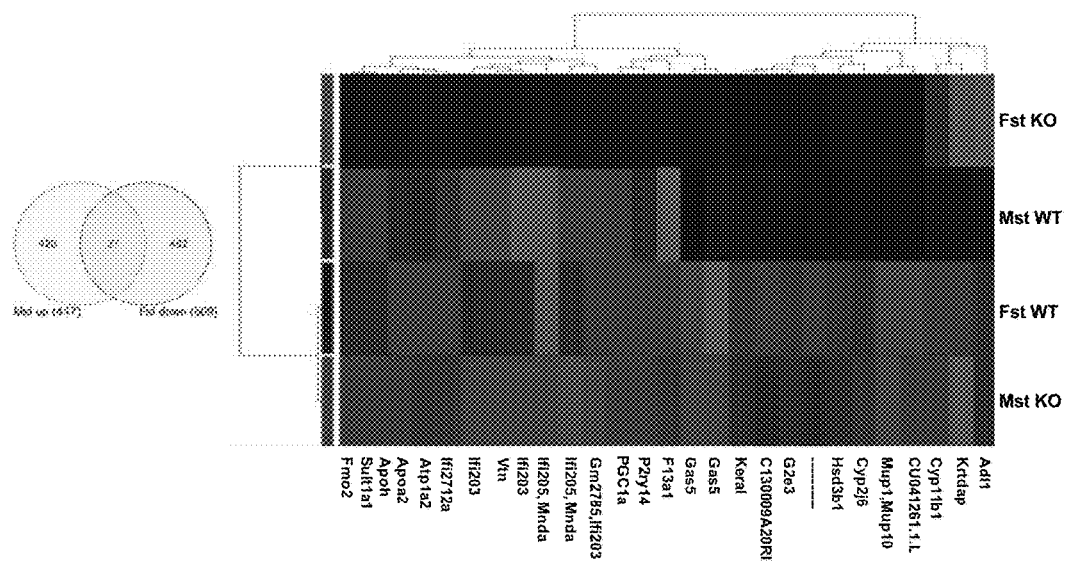
FIG. 14 shows the opposite effects of Fst and Mst on gene expression profiles involved in lipid and energy metabolism in differentiating MEF cultures after 2 days. (A) Left panel, Venn diagram showing 27 common genes that were regulated when Mst levels were high and Fst levels were low. Right panel, Affymetrix and heat-map analysis demonstrating common genes. (B) Left panel, Venn diagram showing 16 common genes that were regulated when Mst levels were low but Fst levels were high. Right panel, Affymetrix and heat-map analysis demonstrating common genes. (C-D) Validation of Affymetrix data by qPCR using gene-specific primers. Experiments were conducted in triplicate. Data are expressed as mean±SD. *, p≤0.05, **, p≤0.01.
Figure 14B:
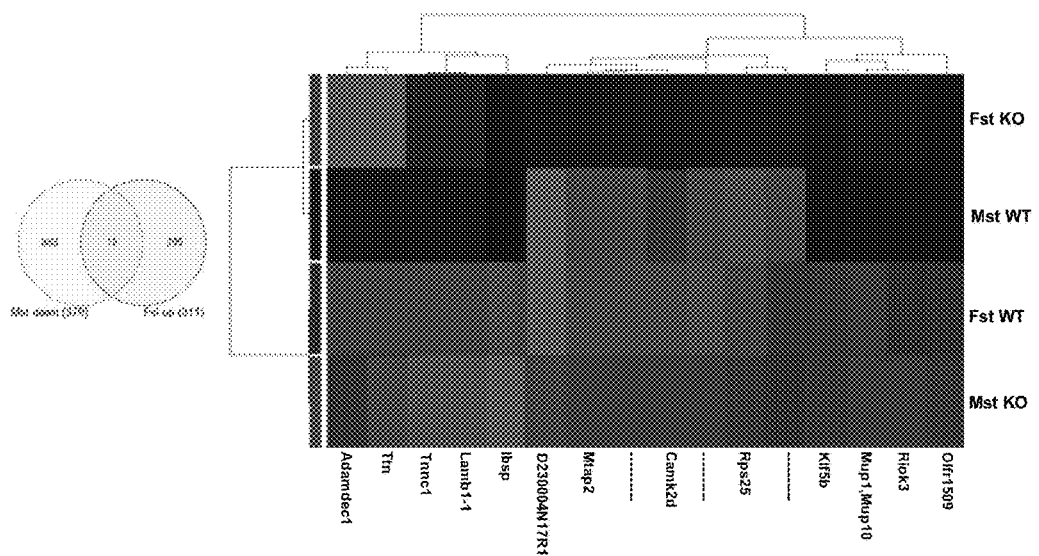
Figure 14C:
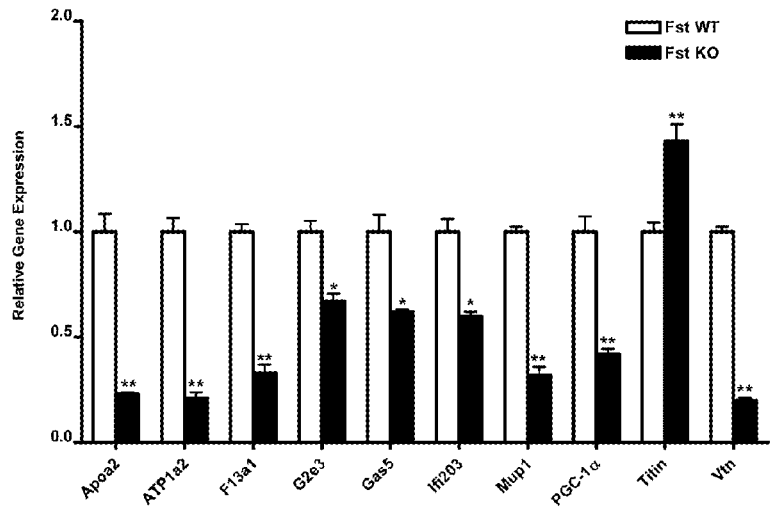
Figure 14D:
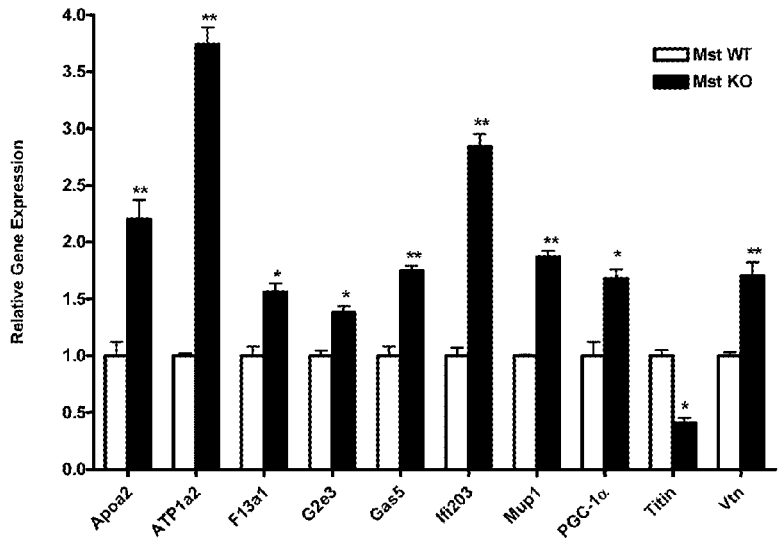

Opposing Effects of Fst and Myostatin (Mst) Expression on Key Metabolic Genes in Differentiating MEFs We and others have recently demonstrated that Mst, a member of the transforming growth factor-beta (TGF-β) superfamily inhibits BAT differentiation program both in vitro and in vivo. Since Fst is known to bind and antagonize Mst action in a variety of conditions, we argued that at least part of the effects of Fst on BAT differentiation may be due to its effect on Mst and therefore, we would be able to identify a common subset of genes that are reciprocally regulated via Fst/Mst axis. Accordingly, we performed Affymetrix analysis using MEFs from both Fst and Mst WT and KO cultures. We identified 27 common genes that were reciprocally regulated when Mst was up but was down (FIG. 14A). Similarly, we also found 16 common genes that were reciprocally regulated when Mst was down but Fst was up (FIG. 14B). We performed qPCR to validate the data from the Affymetrix analysis using gene specific primers. While Fst KO cultures had significant down-regulation of Apoa2 (77.2±1.8%); ATPa2 (79.2±5.1%); F13a1 (67.2±5.5%); G2e3 (33.4±3.9%); Gas (38.2±1.6%); Ifi203 (40.4±2.1%); Mup1 (68.4±5.3%); PGC-1α (58.6±2.9%); and Vtn (78.4±1.8%) gene expression compared to the Fst WT cultures (FIG. 14C). On the other hand, we found a completely opposite trend within the Mst WT and Mst KO cultures. Mst KO cultures had significant induction of Apoa2 (1.38±0.3 fold); ATPa2 (3.74±0.37 fold); F13a1 (1.56±0.19 fold); G2e3 (1.38±0.14 fold); Gas (1.75±0.14 fold); Ifi203 (2.84±0.27 fold); Mup1 (1.87±0.13 fold); PGC-1α (1.68±0.2 fold); and Vtn (1.7±0.3 fold) gene expression compared to the Mst WT cultures (FIG. 14D).

Opposing Effects of Fst and Mst on Cellular Oxygen Consumption

Figure 15A:
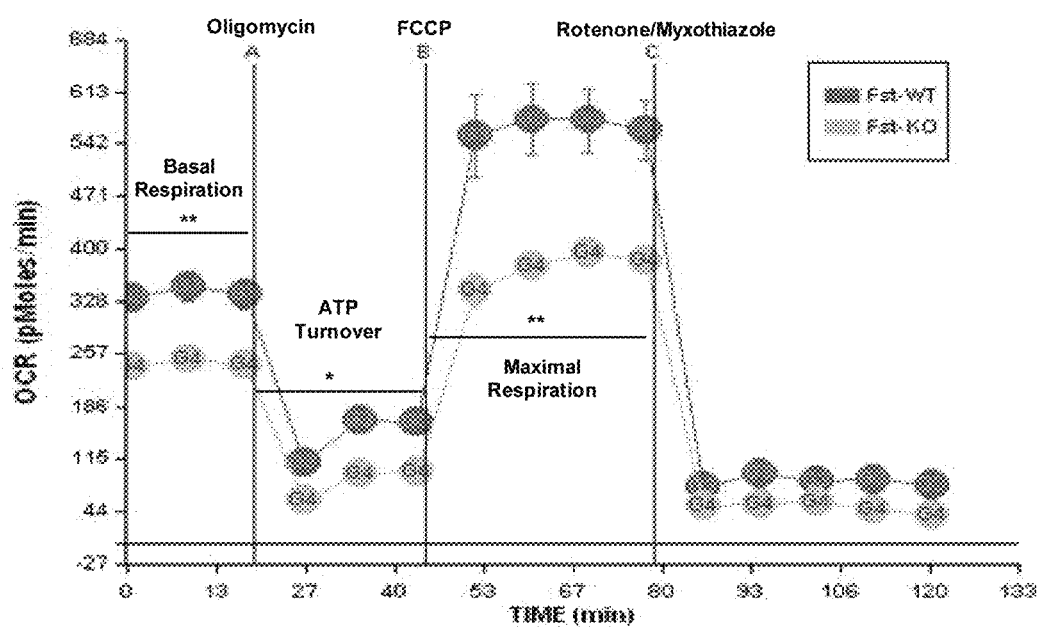
FIG. 15 shows the analysis of oxygen consumption (OCR) rate in differentiating MEF cultures. (A-B) OCR was measured in Fst WT and Fst KO as well as Mst WT and Mst KO cultures using XF24 Extracellular Flux Analyzer. During this experiment, 1 μM oligomycin, 0.5 μM FCCP, and a mixture of 100 nM rotenone and myxothiazol were sequentially added, and the response was monitored as described in Materials and Methods. Experiments were conducted in triplicate. Data are expressed as mean±SD. *, p≤0.05, **, p≤0.01.
Figure 15B:
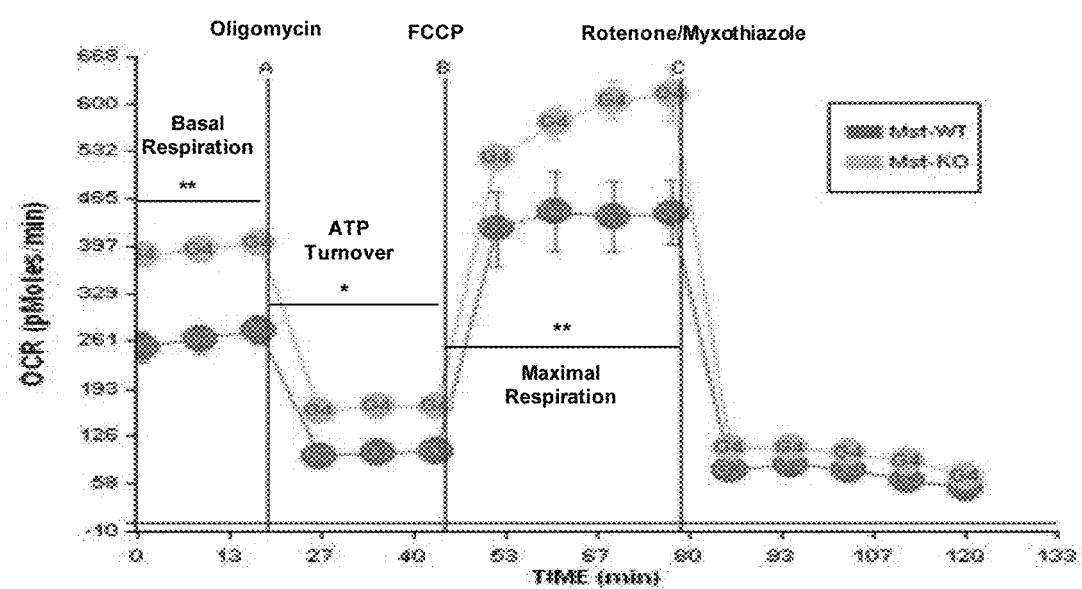

We next evaluated the level of oxygen consumption in Fst WT and Fst KO as well as Mst WT and Mst KO MEFs differentiating under BAT-specific conditions for 2 days (see "Materials and Methods"). As shown in FIG. 15A, Fst KO cultures showed significantly lower levels of basal mitochondrial oxygen consumption (WT: 316±6.7 vs. KO: 275±6.0, p≤0.001); and maximal respiration after addition of 0.5 μM carbonyl cyanide-p-trifluromethylhydrazine (FCCP) (WT: 526±10 vs. KO: 454±10.3, p≤0.001) compared to the Fst WT culture. On the other hand, we find a completely opposite trend on cellular oxygen consumption rate in Mst KO cultures compared to the Mst WT cultures (FIG. 15B). Mst KO cultures had significantly higher basal mitochondrial oxygen consumption (WT: 246±11 vs. KO: 402±14.3, p≤0.001), ATP turnover, as measured by the response to oligomycin (WT: 94±4.5 vs. KO: 167±11.3, p≤0.001), and maximal respiration (WT: 407±10.7 vs. KO: 567±54.9, p≤0.001) compared to the Mst WT cultures (FIG. 15B).

Figure 16A:
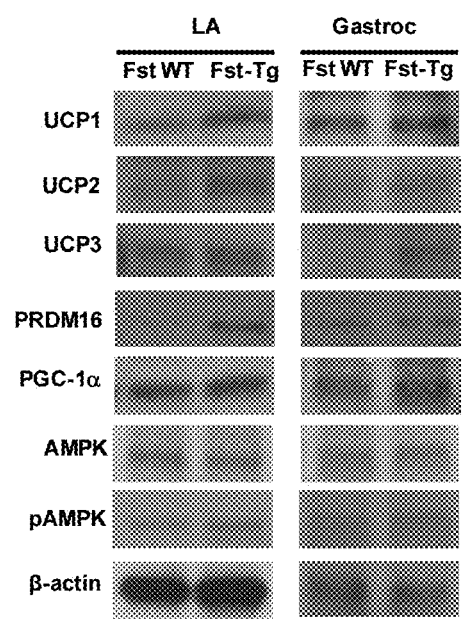
FIG. 16 shows the induction of BAT-specific proteins in skeletal muscle and WAT in Fst-Tg mice. (A) Analysis of key BAT-specific proteins from levator ani (LA) and gastrocnemius (Gastroc) muscle tissues isolated from Fst WT and Fst-Tg mice. (B) Top panel, IHC staining of muscle tissues using anti-UCP1 antibody. Bottom panel, quantitative image analysis. (C) Analysis of key BAT-specific proteins from Epi and SC adipose tissues isolated from Fst WT and Fst-Tg mice. (D) Top panel, IHC staining of muscle tissues using anti-UCP1 antibody. Bottom panel, quantitative image analysis. Experiments were conducted in triplicate. Data are expressed as mean±SD. *, p≤0.05, **, p≤0.01.
Figure 16B:
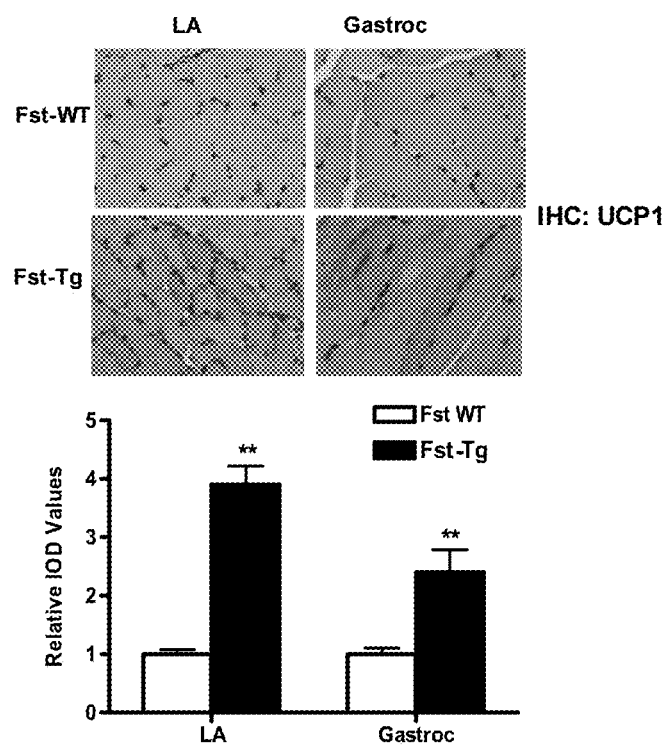
Figure 16C:
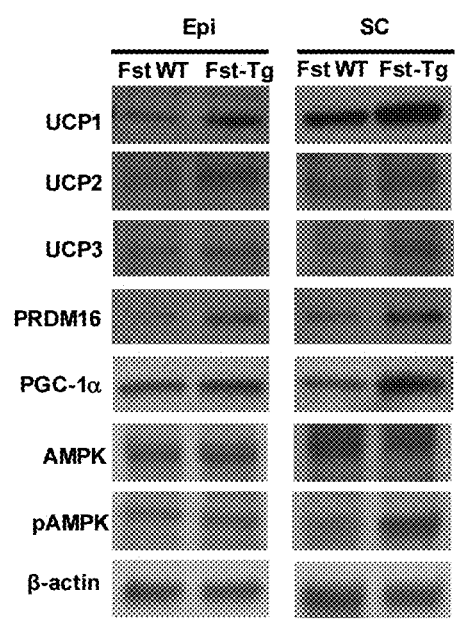
Figure 16D:
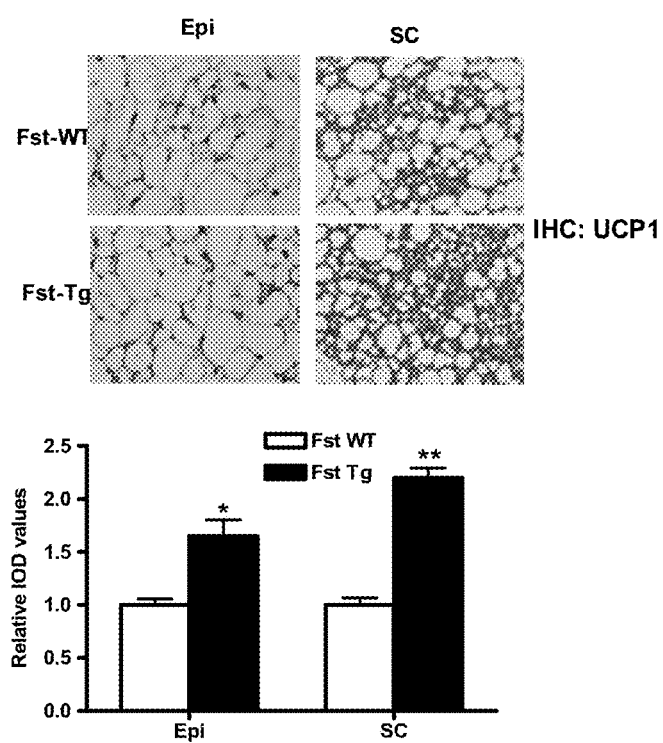

Upregulation of BAT-Specific Proteins in Skeletal Muscle and Adipose Tissues in Fst-Transgenic (Fst-Tg) Mice Compared to the Age-Matched WT Mice We analyzed protein expression of an array of markers implicated in BAT-differentiation and energy expenditure, using skeletal (levator ani, LA and gastrocnemius, Gastroc)

muscle as well as adipose (epididymal, Epi and subcutaneous, SC) tissues from WT and Fst-Tg mice. We found that a majority of these proteins (UCP1, UCP2, PRDM16, and PGC-1α) were upregulated in both skeletal muscle (FIG. 16A-B) and adipose tissues (FIG. 16C-D) obtained from 3 weeks old Fst-Tg male mice compared to the WT mice. Quantitative immunohistochemical (IHC) staining and image analysis of both muscle and adipose tissue sections with anti-UCP1 antibody further confirmed induction of UCP1 expression in LA (3.9±0.24 fold); Gastroc (2.4±0.4 fold); Epi (1.65±0.2 fold); and SC (2.2±0.3 fold) sections (FIG. 16B, D). Although the basal levels of several of these proteins were found to be relatively higher in SC tissues compared to the Epi adipose tissues, this difference was not as apparent in Epi adipose tissues between WT and Fst-Tg mice (FIG. 16A, C).

Figure 17A:
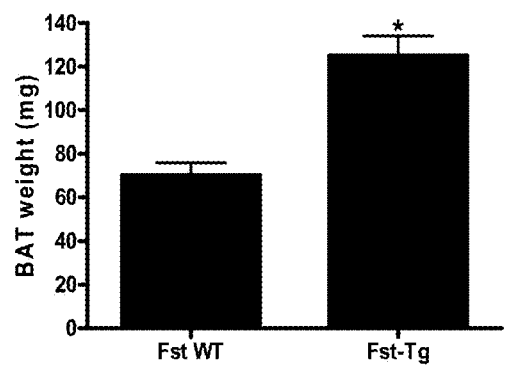
FIG. 17 shows the increased BAT weight and upregulation of BAT-specific proteins in interscapular BAT (iBAT) in Fst-Tg mice. (A) Comparison of iBAT weights from Fst WT and Fst-Tg mice. (B) Analysis of BAT-specific proteins by western blot analysis. Analysis of Fst gene (C) and protein (D) expression in iBAT tissues isolated from Fst WT and Fst-Tg mice. *, p≤0.05, **, p≤0.01.
Figure 17B:
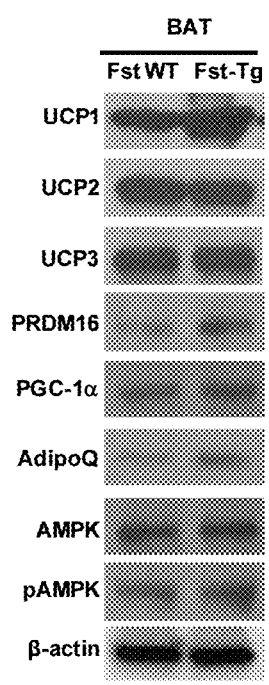
Figure 17C:
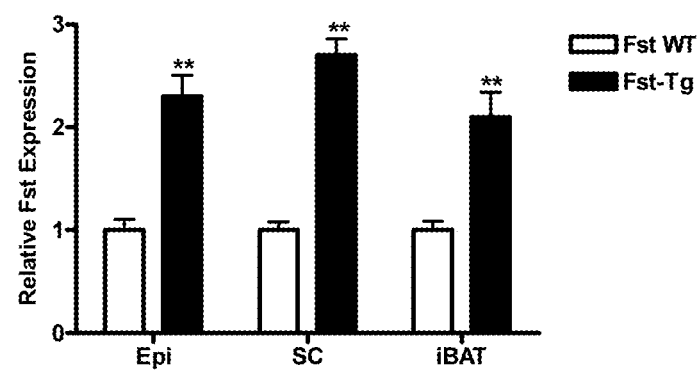
Figure 17D:
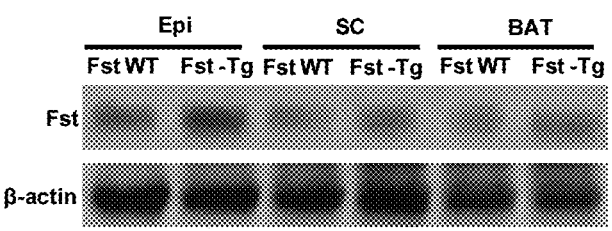

Induction of BAT Mass and Upregulation of BAT Expression in Fst-Tg Mice Compared to the Age-Matched WT Mice We analyzed the interscapular BAT (iBAT) mass in 5 weeks old Fst WT and Fst-Tg male mice. We found a significant increase in iBAT mass in Fst-Tg (1.72±0.44 fold) even after normalizing their total body weight (FIG. 17A). We next analyzed the expression of key BAT markers in iBAT tissues isolated from both groups. Although the basal levels of UCPs in iBATs were clearly higher compared to other muscle or adipose tissues from both groups (data not shown) as expected, Fst-Tg group had induced expression levels of UCP1 (but not UCP2 and UCP3), PRDM16, PGC-1α, pAMPK as well as adipoQ compared to the Fst WT (FIG. 17B). Since Fst transgene in Fst-Tg mice was driven by muscle specific promoter, we analyzed Fst gene and protein expression in all three adipose tissues including WAT (Epi and SC) and iBATs isolated from 5 weeks old Fst WT and Fst-Tg male mice. We found a significant increase in Fst gene expression in Epi (2.3±0.21 fold); SC (2.7±0.16 fold); and iBAT (2.1±0.17 fold) tissues from Fst-Tg mice compared to Fst WT mice (FIG. 17C). The fold difference between skeletal muscle Gastroc muscle was more pronounced (8.7±1.4 fold) in Fst-Tg compared to Fst WT group (data not shown).

Induction of Liver Mup1 Expression in Fst-Tg Mice

Figure 18A:
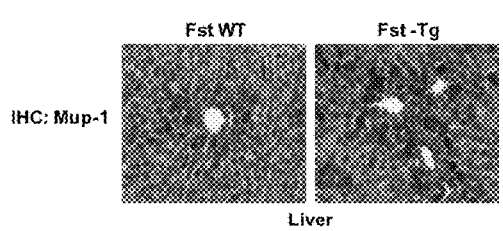
FIG. 18 shows the increased expression of Mup-1 in liver tissues isolated from Fst-Tg mice. (A) IHC analysis of Mup-1 expression in liver sections from Fst WT and Fst-Tg mice. (B) Quantitative image analysis of Mup-1 protein expression. (C) Analysis of Mup-1 gene expression. Experiments were conducted in triplicate. Data are expressed as mean±SD. *, p≤0.05, **, p≤0.01.
Figure 18B:
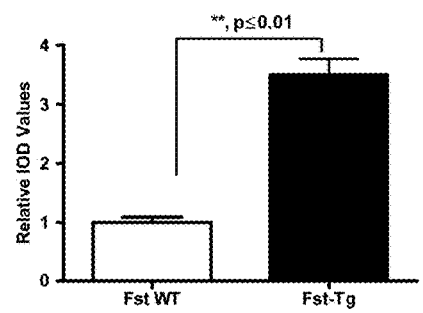
Figure 18C:
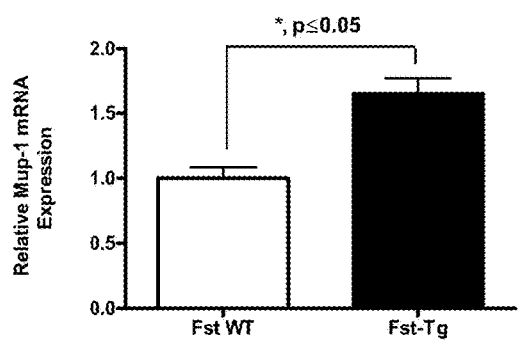

Based on our in vitro findings, we explored the expression of Mup1 in liver tissue sections from both Fst WT and Fst-Tg mice. Our IHC staining and quantitative image analysis data indicates a significant (3.5±0.4 fold) increase in Mup1 protein expression in Fst-Tg liver tissues (FIG. 18A-B). We also performed qPCR analysis of liver RNA samples from both groups. We found a relatively small (1.65±0.21 fold) but significant (p≤0.05) increase in Mup1 gene expression in Fst-Tg group compared to the Fst WT group (FIG. 18C).

Figure 19A:
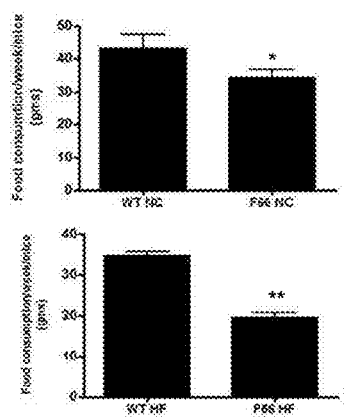
FIG. 19 shows the effect of high fat diet on body weight and abdominal fat volume in Fst WT and Fst-Tg mice. 5 weeks old male mice were fed either regular chow (RC) or high fat (HF) diet for a period of 4 weeks. (A) Analysis of food consumption. (B) Body weight. (C-D) CT-scan and analysis of abdominal fat volume (n=5 per group). Data are expressed as mean±SD. *, p≤0.05, **, p≤0.01.

Decreased Food Intake and Resistance to Diet-Induced Increase in Body Weight and Abdominal Fat Volume in Fst-Tg Mice 5 weeks old Fst WT and Fst-Tg male mice were fed normal chow (NC) and high fat chow (HF) for a period of 4 weeks and their food consumption was monitored. We found that Fst-Tg mice consumed less food compared to the Fst WT mice. While the difference in the consumption of NC between the Fst-WT and Fst-Tg was relatively small (19.4±2.8%, *, p≤0.05); Fst-Tg consumed significantly less HF chow (45.7±4.3%, **, p≤0.01) compared to the Fst WT mice (FIG. 19A). Therefore, Fst-Tg mice showed a selective reduction in predilection for consuming high fat chow.

Figure 19B:
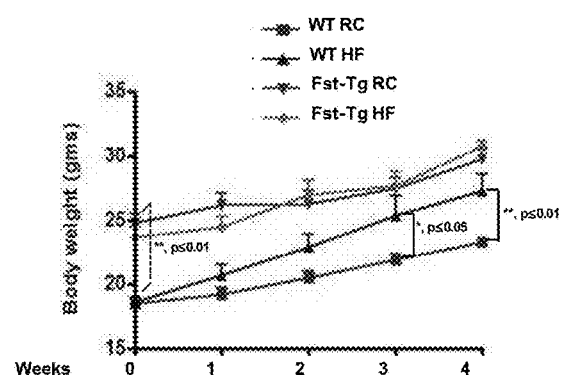

Analysis of initial body weight (5 weeks) showed a significant increase (25.4±0.8%, p≤0.01) in Fst-Tg (24.8±1.7 gms) mice compared to the Fst WT (18.5±1.1 gms) (FIG. 19B). Fst WT mice gained 17.9±0.5% and 42.54±1.3% increase in their initial body weights after feeding NC or HF chow after 4 weeks respectively (FIG. 19B). On the other hand, Fst-Tg mice gained 10.8±0.4% and 28.8±0.4% increase in their initial body weights after feeding NC or HF chow after 4 weeks respectively (FIG. 19B). While there was a significant increase (21.1±0.8%, p≤0.01) in the body weight of Fst WT mice on HF chow diet compared to the mice on NC diet (HF: 26.4±2.4 gms vs. NC: 21.8±1.2 gms); there was no significant increase in the body weights of Fst-Tg mice on HF chow diet compared to the mice on NC diet (HF: 29.4±1.3 gms vs. NC: 28.8±0.4 gms) after 4 weeks (FIG. 19B).

Figure 19C:
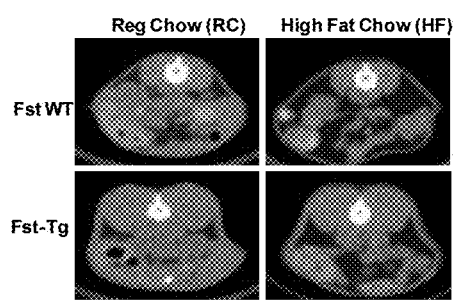
Figure 19D:
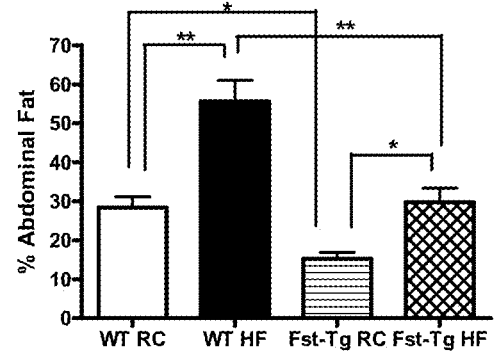

We further analyzed the effects of NC and HF chow diets on Fst WT and Fst-Tg on their abdominal fat content by CT scans. The basal level of abdominal fat was significantly lower (46.4±1.4%, p≤0.05) in Fst-Tg (15.2±3.6%) mice compared to the Fst WT (28.4±6.2%) mice (FIG. 19 C-D). After 4 weeks of HF chow diet feeding, the abdominal fat volume increased to 55.6±12.2% in the Fst WT mice; while it increased only to 29.8±8.1% in Fst-Tg mice (FIG. 19C-D).

Increased Glucose Clearance in Fst-Tg Mice

Figure 20:
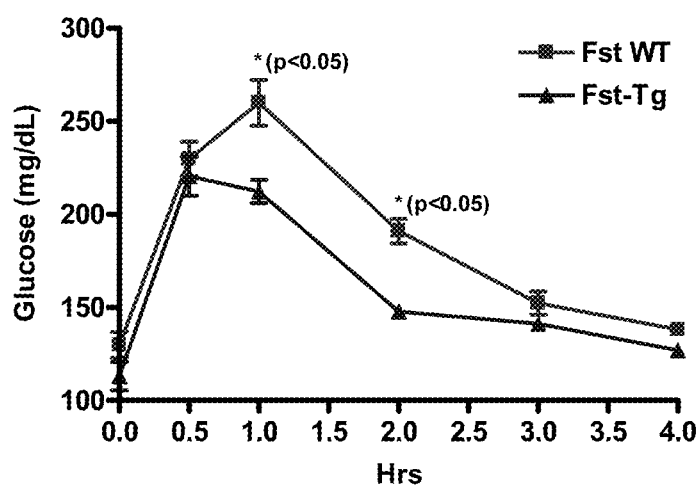
FIG. 20 shows the results of the glucose tolerance test (GTT) in Fst WT and Fst-Tg mice. 5 weeks old male mice were fasted overnight and given D-glucose (1 g/kg) by intraperitonial injection. Blood glucose was measured at different time points (n=10 per group). Data are expressed as mean±SD. *, p≤0.05, **, p≤0.01.

To further analyze the effect of Fst on glucose metabolism, we performed GTT in fasting Fst WT and Fst-Tg mice (16 hrs) after intraperitoneal injection of glucose (1 g/kg). Fst-Tg mice (113±24 mg/dl) had lower basal levels of plasma glucose compared to the Fst WT mice (129.8±16.2) (FIG. 20). There was a significant difference (p≤0.05) in glucose levels between the groups at 1 hr (Fst WT: 260±34 vs. Fst-Tg: 212±23) and 2 hrs (Fst WT: 191±18 vs. Fst-Tg: 147±8) following glucose injection, suggesting that Fst-Tg had increased ability for glucose clearance (FIG. 20). Analysis of glucose levels at subsequent time points (3-4 hrs) showed no significant difference between the two groups.

Biochemical Analysis of Plasma in Fst WT and Fst-Tg Mice

Both Fst WT and Fst-Tg mice were fed on two different diet regimens as described in FIG. 19A-D. Analysis of plasma biochemical was performed to compare the effect of Fst transgene expression as well as the effect of HF chow (Table 8).

TABLE 8

Serum profiles of Fst WT and Fst-Tg mice fed on regular and high fat chow

| | Regular Chow (NC) (n = 5) | | High Fat Chow (HF) (n = 5) | |
| --- | --- | --- | --- | --- |
| | Fst WT | Fst-Tg | Fst WT | Fst-Tg |
| TG | 105.7 ± 26.7 | 51.7 ± 5.5*** | 153.8 ± 3.3 | 41.3 ± 15.2*** |
| Total Cholesterol | 193.2 ± 26.2 | 157.3 ± 17.5** | 246.5 ± 27.3 | 224.8 ± 24.9 |
| HDL | 159.6 ± 13.6 | 133.8 ± 11.1* | 211 ± 18.3 | 188.6 ± 18.7 |

TABLE 8-continued

Serum profiles of Fst WT and Fst-Tg mice fed on regular and high fat chow

|  | Regular Chow (NC) (n = 5) | | High Fat Chow (HF) (n = 5) | |
| --- | --- | --- | --- | --- |
|  | Fst WT | Fst-Tg | Fst WT | Fst-Tg |
| UC  | 46.2 ± 7.9 | 36.6 ± 5.5   | 56.5 ± 3.4 | 50.8 ± 8.3   |
| FFA | 73.5 ± 7.8 | 49.3 ± 8.5*  | 71.3 ± 6.3 | 49.5 ± 1.2*  |

Table 8 illustrates the metabolic parameters in Fst WT and Fst-Tg mice fed either regular chow (RC) or high fat (HF) chow diet for 4 weeks. Serum samples were collected and analyzed for various metabolic parameters (n=5). Data are expressed as mean±SD. *, $p \leq 0.05$, , $p \leq 0.01$, *, $p \leq 0.001$. Fst-Tg mice had significantly decreased levels of plasma TG (WT: 105.7±26.7 vs. Tg: 51.7±5.5, $p \leq 0.001$), total cholesterol (WT: 193.2±26.2 vs. Tg: 157.3±17.5, $p \leq 0.01$) HDL (WT: 159.6±13.6 vs. Tg: 133.8±11.1, $p \leq 0.05$), as well as FFA (WT: 73.5±7.8 vs. Tg: 49.3±8.5, $p \leq 0.05$) levels compared to the Fst WT mice fed on regular chow (Table 8). There was also a significant decrease in plasma TG (WT: 153.8±3.3 vs. Tg: 41±15.2, $p \leq 0.001$) as well as FFA (WT: 71.3±7.8 vs. Tg: 49±1.2, $p \leq 0.05$) levels in Fst-Tg mice compared to the WT of HF chow for 4 weeks (Table 8). There was no difference in total cholesterol, HDL or UC levels between Fst WT and Fst-Tg mice when fed on HF chow.

Discussion

Fst is an extracellular binding protein, which binds activins and Mst with high affinity to inhibit signaling through TGF-β superfamily members, which regulate diverse processes as cell growth and differentiation and secretion of follicle stimulating hormones (Lee et al. Mol Endocrinol. 2010; 24(10): 1998-2008; Schneyer et al. Endocrinology. 2008; 149(9):4589-95; Ying. Endocr Rev. 1988; 9(2):267-93). Fst KO mice die shortly after birth (Matzuk et al. Nature. 1995; 374(6520):360-3.) and therefore, have not been previously studied as an in vivo model to investigate other possible defects that might be critical for their survival. Maintenance of body temperature through activation of thermogenic program by brown adipose tissues (BAT) is a critical requirement for newborn pups, especially during their early hours of life (Cannon et al. Physiol Rev. 2004; 84(1):277-359; Charalambous et al. Cell Metab. 2012; 15(2):209-21). While the role of Fst in promoting skeletal muscle mass is well documented (Singh et al. Endocrinology. 2009; 150(3):1259-68., Braga et al. Mol Cell Endocrinol. 2012; 350(1):39-52; Winbanks et al. J Cell Biol. 2012; 197(7):997-1008; Gilson et al. Am J Physiol Endocrinol Metab. 2009; 297(1):E157-64), its role in the regulation of BAT mass has never been previously investigated. BAT metabolizes excess stored energy in triglyceride depots to generate heat for thermogenic purposes (Nedergaard et al. Cell Metab. 2011; 13(3):238-40). Given the epidemic of obesity in humans, there is alarming critical need to identify novel regulators of BAT expression/activity in order to explore avenues for developing anti-obesity therapies.

Recent data suggest that Mst and related members of TGF-β superfamily inhibit BAT differentiation (Braga et al. Obesity, 2012 doi: 10.1038/oby.20117; Yadav et al. Cell Metab. 2011; 14(1):67-79; Zhang et al. Diabetologia. 2012; 55(1):183-93). Fst is a known antagonist of activins and Mst, and therefore we investigated whether Fst plays an important role in BAT differentiation. Since both skeletal muscle and BAT share common progenitors (Seale et al. Nature. 2008; 454(7207):961-7; Timmons et al. Proc Natl Acad Sci USA. 2007; 104(11):4401-6), in our current study, we tested whether that loss of Fst leads to compromised BAT differentiation and defective thermogenesis at the time of death in newborn Fst KO pups. The systematic approach utilized in this study, using primary cultures of MEFs as well as Fst transgenic mice as our in vitro and in vivo models, have suggested a novel role of Fst during BAT differentiation and lipid metabolism.

Since Fst KO mice are not viable, we initially isolated WT and KO embryos by genotyping and made primary cultures of MEFs to identify differentially expressed proteins and genes involved in lipid and energy metabolism. We demonstrate for the first time that Fst loss-of-function in MEF cultures leads to a significant decreased capability of these cells to express UCP1, PRDM16, PGC-1α and other key brown fat markers when allowed to differentiate under BAT-specific conditions. Recombinant Fst treatment of both WT and KO MEFs led to significant increase in BAT-specific markers, suggesting a novel role of Fst during BAT differentiation. Ingenuity pathway analysis (IPA) of gene expression profiling data obtained from WT and Fst KO MEFs clearly suggest lipid metabolism to be the most significantly affected function between the two groups. Analysis of differentially expressed genes identified several key genes involved in lipid and energy metabolism that were significantly down-regulated in Fst KO groups that included acyl-Co-A synthetase long chain family member 1 (ACSL1), adiponectin (AdipoQ), CD36, PGC-1α, haptoglobin (Hp), fatty acid binding protein 4 (FABP-4), plasminogen (PLG), PPARγ, thyroid hormone responsive (THRSP) and major urinary protein-1 (Mup1) amongst others. ACSL1 is required for cold thermogenesis and directs fatty acid towards β-oxidation (Ellis et al. Cell Metab. 2010; 12(1):53-64). AdipoQ, an adipose specific protein is upregulated in brown adipose tissues (Shetty et al. Endocrinology. 2012; 153(1):113-22.) and plays a significant role in promoting insulin sensitivity and regulation of plasma free fatty acid concentrations (Shetty et al. Endocrinology. 2012; 153(1):113-22; Combs et al. Endocrinology. 2004; 145(1):367-83; Asterholm et al. Am J Pathol. 2010; 176(3): 1364-76). PGC-1α is a key regulator of thermogenic program in brown fat. Transgenic mice over-expressing PGC1-α are reported to be resistant to age-related obesity and diabetes (Liang et al. Am J Physiol Endocrinol Metab. 2009; 296(4):E945-54). CD36, a fatty acid translocase, plays a significant role in lipid metabolism and has been implicated in dietary fat taste perception (Goldberg et al. J Lipid Res. 2009; 50 Suppl:S86-90; Zhang et al. Acta Histochem. 2011; 113(6):663-7). Mup1, a key regulator of glucose and lipid metabolism (Hui et al. J Biol Chem. 2009; 284(21):14050-7; Zhou et al. J Biol Chem. 2009; 284(17): 11152-9.) was significantly down-regulated in Fst KO MEFs undergoing brown fat differentiation compared to the WT, although its expression was undetectable in MEFs from both groups under normal growth conditions. On the other hand, liver tissues isolated from Fst-Tg mice show a clear upregulation of Mup1 gene and protein expression, suggesting that Mup1 expression is clearly regulated by endogenous Fst levels. Fst KO MEFs also had significantly lower levels of phosphorylated AMPK (adenosine monophosphate-activated protein kinase), which acts as a metabolic fuel gauge and plays an important role in regulating cellular energy balance (Cantó et al. Nature. 2009; 458(7241):1056-60). Haptoglobin (Hp) is a hemoglobin (Hb) binding protein that plays a major role in preventing renal damage and Hb loss by renal excretion (Levy et al. Antioxid Redox Signal. 2010; 12(2):293-304), was also found to be significantly down-regulated in Fst KO MEFs. Our global gene profiling data therefore, clearly suggest that Fst is a key modulator of lipid and energy metabolism and Fst loss-of-function results in severe metabolic defects that may be essential for survival.

TGF-β/Mst/Smad 3 signaling has recently been demonstrated to promote transdifferentiation of WAT to BAT and protect mice from diet-induced obesity (Braga et al. Obesity, 2012 doi: 10.1038/oby.20117; Yadav et al. Cell Metab. 2011; 14(1):67-79; Zhang et al. Diabetologia. 2012; 55(1):183-93). Data published from our laboratory and others suggest that Fst antagonize Mst activity as well as inhibit overall TGF-β/Mst signaling in a variety of in vitro models (Singh et al. Endocrinology. 2009; 150(3):1259-68; Braga et al. Mol Cell Endocrinol. 2012; 350(1):39-52; Amthor et al. Dev Biol. 2004; 270(1):19-30). Accordingly, we also analyzed gene expression profiles of differentiating Mst WT and Mst KO MEFs and identified 27 common genes that were upregulated by Mst and reciprocally down-regulated by Fst. Similarly, we also identified 16 common genes that were upregulated by Fst and reciprocally reduced by Mst. This reciprocal effect of Fst and Mst expression was also reflected in their cellular bioenergetics. While Fst KO MEFs had significantly lower OCR, compared to the Fst WT MEFs, this trend was found to be opposite in Mst KO MEFs, which had significantly higher OCR compared to the WT group. Our data therefore, clearly suggest that Fst increases OCR in MEFs and suggest that inhibition of Mst may at least in part be responsible for the BAT-inducing effects of Fst.

In order to get further insight into the role of Fst during BAT differentiation and regulation of BAT mass, we analyzed the expression of BAT-specific proteins in muscle and adipose tissues isolated from both Fst WT and Fst-Tg male mice. Our findings clearly suggest that Fst-Tg mice have significantly increased expression of BAT specific markers in muscle and both adipose tissues compared to the WT mice. It has been demonstrated that ectopic expression of key brown fat marker UCP1 in intramuscular depots in 129 male mice protects them from metabolic disorder and weight gain when challenged with high fat diet as a result of higher basal energy expenditure compared to the WT mice (Almind et al. Proc Natl Acad Sci USA. 2007; 104(7):2366-71). In another study, Li et. al, demonstrated that mice overexpressing UCP1 in skeletal muscle are resistant to obesity, have lower glucose and insulin levels and better glucose tolerance than control mice (Li et al. Nat Med. 2000; 6(10):1115-20).

Our data provides clear evidence that Fst transgenic mouse are resistant to diet-induced weight gain and are at lower risk of developing metabolic syndrome-like state compared to the WT group.

Collectively, our data identifies Fst as a novel mediator of lipid and energy metabolism in vitro and in vivo, and thereby, suggest the therapeutic potential of this novel molecule that has the ability to promote skeletal muscle as well as BAT mass and activity. Our current data suggest that inhibition of Mst/TGF-β signaling in specific cell types is a useful mechanism by which Fst regulates overall lipid and energy metabolism. Fst may also directly regulate Myf5, a common precursor for both skeletal muscle as well as brown adipose tissues through an independent mechanism.

Example 3—Fst Transgenic (Fst-Tg) Muscle and Fat Tissues have Decreased Levels of Branched Chain Amino Acids (BCAAs) and Increased Levels of Omega-3 Polyunsaturated Fatty Acids (ω-3 PUFAs)

Figures 21A, 21B, 21C, 21D, 21E:
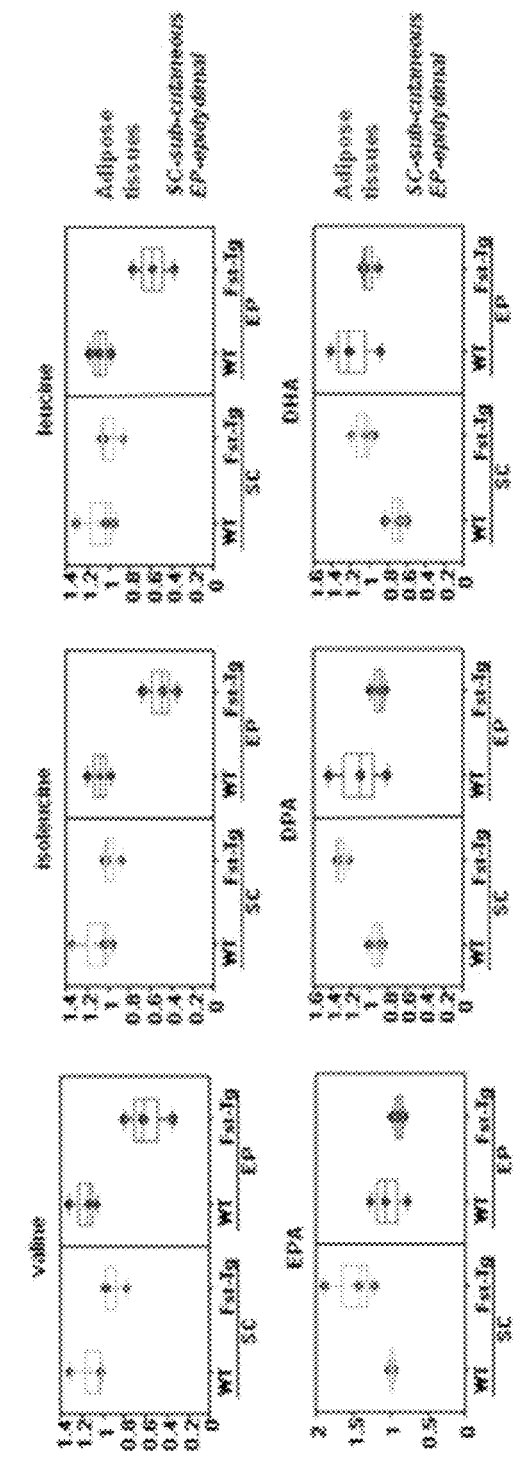
FIG. 21 shows Fst transgenic (Fst-Tg) muscle and fat tissues have decreased levels of branched chain amino acids (BCAAs) and increased levels of omega-3 polyunsaturated fatty acids (ω-3 PUFAs).

Metabolomics and principal component analysis has identified BCAA as the major component that showed strongest difference between obese and lean groups (Newgard et. al. Cell Metabolism 2009; (9)311-326; Nedergard et. al. Cell Metabolism 2012(15)606-614). BCAAs are well known to contribute to the development of obesity-associated insulin resistance and glucose intolerance (Wurtz et. al. Diabetes Care 2012:108; Newgard et. al. Cell Metabolism 2009; (9)311-326). We performed Metabolomic analysis using two skeletal muscle (levator ani and gastrocnemius) and adipose (subcutaneous and epididymal) tissues from WT and Fst-Tg mice to test the effect of Fst transgene expression on BCAA catabolism. We found that gastrocnemius muscle and epididymal fat tissues had significantly lower levels of major BCAAs that include valine, isoleucine and leucine compared to the WT group (FIG. 21), suggesting that Fst-Tg mice have increased insulin sensitivity and glucose tolerance and are less likely to be obese even after consumption of high fat diet rich in BCAAs. On the other hand, ω-3 PUFAs, especially eicosapentaenoic acid (EPA), docosapentaenoic acid (DPA) and docosahexaenoic acid (DHA) are well-known to exert hypolipidemic effects and prevent development of obesity and insulin resistance in animals as well as in humans (Kudo et. al. Diabetologia 2009(52)941-951; Woodman et. al. Am J Clin Nutr 2002(76)1007-10015). We found that the subcutaneous adipose tissues from Fst-Tg mice had significantly increased level of EPA, DPA and DHA compared to the WT tissues. Our data therefore, indicates that Fst treatment can be beneficial and may protect human subjects from obesity and insulin resistance.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of alleviating a metabolic syndrome related disorder in a subject in need thereof, comprising administering to the subject a therapeutically effective amount of a purified full length follistatin polypeptide.

2. The method of claim 1, wherein the metabolic syndrome related disorder is diabetes, insulin-resistance, obesity, hypertension, an insulin resistance disorder, or hepatic steatosis.

3. The method of claim 2, further comprising administering to the subject a second agent that: increases the activity or protein level of adiponectin in a cell; increases the activity or protein level of 5'-AMP-activated protein kinase (AMPK) in a cell; is an anti-diabetic agent; or is an anti-obesity agent.

4. The method of claim 2, further comprising the use of one or more nationally approved drugs in combination with the purified full length follistatin polypeptide.

5. The method of claim 4, wherein the nationally approved drug is selected from a class of drugs consisting of an antihypertensive, anti-glycemic, anti-lipidemic, and cholesterol-lowering drug.

6. The method of claim 2, wherein the subject, after receiving the therapeutically effective amount of the purified full length follistatin polypeptide, exhibits reduced high fat food cravings and consumption.

7. The method of claim 2, wherein the metabolic syndrome related disorder is diabetes, insulin-resistance, obesity, or an insulin resistance disorder.

8. The method of claim 7, wherein the method reduces body weight of the subject or alleviates weight gain.

9. The method of claim 7, wherein the subject receiving treatment exhibits reduced high fat food cravings and consumption.

10. A method of ameliorating obesity in a subject in need thereof, comprising administering to the subject a therapeutically effective amount of a purified full length follistatin polypeptide.

11. A method of suppressing appetite in a human having or suspected of having a metabolic syndrome related disorder selected from the group consisting of diabetes, insulin-resistance, obesity, hypertension, an insulin resistance disorder, and hepatic steatosis, comprising administering to the human a therapeutically effective amount of a purified full length follistatin polypeptide.

12. The method of claim 1, wherein the metabolic syndrome related disorder is hypertension.

13. The method of claim 1, 10, or 11, wherein the purified full length follistatin polypeptide is encoded by the nucleic acid sequence of SEQ ID NO:1.

* * * * *

SEQUENCE LISTING

<160> NUMBER OF SEQ ID NOS: 43

<210> SEQ ID NO 1
<211> LENGTH: 13041
<212> TYPE: DNA

<213> ORGANISM: Homo sapiens

<400> SEQUENCE: 1

| | | | | |
|---|---|---|---|---|
| accagaaaat | aaaacatacc | aaagtaacta | cagcatgcta | ctcaccttca | 50 |
| gccaatgaat | aatccaggaa | ggtggctctt | actttgattg | acacgttgtt | 100 |
| tccaacataa | agtaggggaa | actgaacagc | aaatcctagt | ttgccctcct | 150 |
| cacaccttct | atgcagttga | aagtgtaaat | ggaatcaggg | ttaaaagtgc | 200 |
| taaaggtcac | acacagatat | tttcagtcat | atccaaatat | atgaatcatt | 250 |
| tatgttgtca | aagcgaccta | aaatacttta | gaattttcta | ttaatccaat | 300 |
| gtaacatccc | cattctaagg | cataatttga | attatttact | aagatttatt | 350 |
| ttaactactt | aattatgttg | aacttgaata | tattaatatg | gctagtttaa | 400 |
| gtgactatgt | gacaactagc | ttagctgact | tctggaaacc | caaaatatt | 450 |
| tctaaaatta | aaggggaaag | caaggcaata | aaaatgttac | acagaaacaa | 500 |
| gtagtatcaa | aaggaagag | ctatccatga | ttgatcagct | ctgtataaca | 550 |
| ccaaagcaac | actgaaaaga | gaaaagttca | agtaatccgt | tgttttctca | 600 |
| gttatatata | tatatatata | tatatattac | ataaaacata | tttttctaat | 650 |
| gatttttta | aaccttaatt | gaccggtagt | ttggatatct | tgggtaaaca | 700 |
| ttgcttctac | gtactcacat | ttcttaactt | tttagttctg | taatgattca | 750 |
| accaatacag | aactactgcc | cccatccccc | tactcaaatc | cttatgctag | 800 |
| cctatgaagt | tgcataatgc | caaagactat | gacacattaa | gtaactgttt | 850 |
| tgtacctaga | ataaaatctg | attttaaaat | cattttagcc | tattttcaa | 900 |
| atgcttaact | tttgttgttt | aatcaagatt | gattatttgc | acttgaaaat | 950 |
| gtattcattt | tgcaaaacac | ctaacttcaa | aaaaagcttg | acatttaatc | 1000 |
| ttaaggcaaa | aaaaaaaaaa | aagctactca | gttcatgact | ttcaaatagt | 1050 |
| ctctacataa | cctcacccca | ctccctccat | attctctttt | taggtactga | 1100 |
| aatttaacca | ggtcagttct | ggtctcaaat | aacaatgtca | tatgagttta | 1150 |
| aatagctatc | tagggagtta | gattgaatca | tttgctaaac | tctaatattt | 1200 |
| taaatttata | aacttcagaa | ggaagacagc | ttttgaagct | gacaaaagac | 1250 |
| caatcagaaa | acagtagtct | ttttgtgtgc | tgcccagaaa | ttcagctaca | 1300 |
| aagtggtcct | attgtgtttc | tcataattta | cattttatt | tggcagagca | 1350 |
| gaaaggaaaa | ataagaagtc | aaacttggag | gcatacaaca | aaaatgaaag | 1400 |
| gcgacatttt | tattttaaaa | tgtccccttg | acatttagat | atctacaaac | 1450 |
| ccaatattta | acatttacag | gcgatataac | agtaaaagaa | atagcagctg | 1500 |
| tttttctgtg | atgtcactga | acaggtgtgg | taccatttca | taccacagaa | 1550 |
| atgggatgga | tctcttgctg | atgcccacag | aaagcctata | aggaaccagt | 1600 |
| attgacctgt | gtctcatttc | ctcagttatg | atctgaaaat | aaccctagat | 1650 |
| ggcaagagtc | atggtgactg | atctgtgctg | atttggagca | gacattctcc | 1700 |
| caaacagatc | aatactatcc | aaggtgcagc | tgaaaaacag | gatgagcttg | 1750 |
| tatcactaaa | caaacaccaa | gctgcttatt | caaaagggca | aaagcaaacac | 1800 |
| agcacttatg | ttttccacag | tgtgtttgcc | agtgacctca | accctgacct | 1850 |
| gcagggtcac | cttctctggg | acgagaagta | atcctgtgtt | gggtcaccct | 1900 |

```
ctggtactga gggactccta tttgtggtgc catttttttac aatgagagct      1950 actgtgtctg ctttggctta gccaagacaa ttacatgatg ccaaaacaac      2000
tagtcaaggc agtcaattta gtcaaatgac tggtctgagc atttggcatt      2050
acatagacaa aaaatgaaat agaaatgaaa tttttacttt tacccaatca      2100
tactggaatt gtgaggatac aacttaaatt aatttagaaa gttttgtga       2150 catcagttgt ttctatatac ataaactaaa ataagtatct ggacaaacta      2200
aatagttttg ctcaaacatg gaaaattttt tgactagccc ctccaaattg      2250
cttctattct aatcttcatt tagctacaca gaccttcccc caaaaaggta      2300
atctttgtgt atacttgtat gaccctttta catcaacatg ttatatgtac      2350
atataggaat gaacaaaatt aaaatctaat aagaacatac aagttatatc      2400
actattctcc ttgctatacg gttataaaat atgatgagat tatgaacttt      2450
aaaacaatct tcccaaagat attgagaaaa taaatatgga ttaaaacgtg      2500
attctatatt tctccaggca agatgacttc atatacaact aggcatataa      2550
gtaaaattta aatattttgt atagtcctag ggtggaaagt ctaagaaaaa      2600
gaccccagtt tccagaggct actggccaat tcaggaccaa taaatatatt      2650
taaactggag acaaatataa aatcatgtaa ttatgtatga tcattgatag      2700
cattgctgta agatccagtt acttaccatc tgagatcttt tatgcatttg      2750
gaatgtttat ttttcaacct tggatatacg gtttgatacc tctaccttaa      2800
aaagaagctg tgtctcttgc tgccattaaa agacagggta gggggaaaag      2850
tcaagtaaca atacttgtta gcttctcttt cctttaactt atccctgggc      2900
aggggtgggg gaacctttaa gcagagaaaa caaactttcc ctccagcaca      2950
tcattgtata aggactatac catttctctg aataaagaag aaataaattc      3000
agctttggaa ctctgccatt gagtggcggc tcctgcaaag gggacagttt      3050
gctattaatt gttaatgtcg tctgccatta gagggcacta aacaactcta      3100
cattaatgag ttggagggaa gagagaaaag gagactggaa agaaagaga       3150 gggagaaaag ggagggagag tacgggtaga gtctgggtag agggagggaa      3200
ggagagaaga gggaaggag  tagggaaag agagcagagg gaatgagttg       3250
gaggactgga gggaaaggga gaaggggaga gagacagcga gacagaaaca      3300
gacagaatga ttctggaaag attaagaagg atgtggagcc cccacagccg      3350
tctgaagtga gcaaaatcca gtctcccccg ggccgcccga gcccctcccc      3400
tcccgtcctc atgacggtaa ttataaagcg aaaagcggcg gcgaggtcac      3450
ccgcttttac cagcctgctg caccgaatgc gcgcggtgca ggtgcggcgg      3500
ccgcggggct ttgtgattca tgcccacttt caaggggggg cttgggcccg      3550
tctgagaggc acccaaacaa ctgtcttcta atattagcac ggctgtattt      3600
cgggatctat tatagtctgt ccagacagat cccattgtaa tgggatcttt      3650
tattaaaaga ttagcactat ctcctgcagt tggtggaaaa aaatctgtta      3700
tcactgagtt atttgcagtt gtggaggggg gaaggttgac ggaagatggg      3750
gggtgggagg gctagaggag gactggggga gggtctggcg gggggagggc      3800
agttgcaggg ggggaagaag ggcagatttg aaattcgtag aacaaatccc      3850
```

```
agtgacctgc gaatgtccaa gaattttgtc tgcatacttc gctatctgtt      3900
gtccttcggg cttcagatgc gaaaagaaca aatttaaaag gcagctttgg      3950
aataaacaat atagcatttt ccgtgaagta atcgttttat ataaaaggaa      4000
atatcgcctc ctcagtttca ttcagcggtg ccaaaaatgt tataaatgag      4050
agacccgcca actttcagcg aagaatgcca ggcactgtac ttaataaact      4100
gaggctacag aagttcatta tggatgttgc aatcttttt attccgcgaa        4150
aagagagaag acgagacaga aagagagaga gattggagcc gaggagactg      4200
agagacagac agaggcacac aggacagaaa ctggggagtc tccaggcggg      4250
agaggaaggg ggggccagac cgcctacgtc ggcgcccccg ctccgggctc      4300
cgactccaga cgccgcgaag tgaaggggga gaaagaaag ggagagggcg       4350
aggctgtgcc gcggggagac cgggcctgag gtgttaaaca tttttgtttg      4400
cttccgacta gtccgacga agggccgcgt ctcggtagcg ctctgccagg       4450
gtggaaggtg ccggggccgg ggttcctagc aacacctctg ggctgggggt      4500
ggctgcaaag tcaggcactc acagacccag acacaaaacc tcgcgggtcc      4550
cgcgcccagg ctgcgggtgc ccggaaccgc cgcgaggccg cgcgctccg       4600
acccgacccg gggcgggata tttgggcagc ccggggctct tcggccgttt     4650
gcaaaagtct ctttggagcg gaggagaggc agcacgagag caaactcccg      4700
ggttcccccc gccaccgcct ccagcgcccc caccgcgccc tccctctcac      4750
actcgcgcgc gcgcgcacac acactcacac acacactcac acacacaccc      4800
gccaccccgg gcgcgccggc gctgccggcg agcggcggcg agcaggactt       4850
gaagtgggtg ttcttcccca ctccccaccc ccgacgcgta gccccaacc        4900
cccgccccgg tcgccttccc cctccctctc gctcctacgc aaataagaac      4950
tcgacgattc ccttccagcc gttttgattt cgggcacctc cgaaagataa      5000
ttgggaaggg tttccagaag gtgggaaatg tcacctgatt cacactgaac      5050
ttttgaaagc tccccacccc caaggagccg cgcacaccct cgctcgcggc      5100
cgccctccca cagccccaca cactgggaga ccgcccaccg caaaccgcgg      5150
agaccccgt ctagatttaa agcgcggctg cgcccggctt ctgacgtcca        5200
ttgaatcgcg cgggcggccg gcggcgagcg cggggctgcg ccgggatcgc      5250
tgcgccctcc gccgctggcc tctgcgacgc gcgccgctcg cccgagccac      5300
ccgccgccgc gccggctccc cgcgccgctg cgctcctcgc cccgcgcctg      5350
cccccaggat ggtccgcgcg aggcaccagc cgggtgggct ttgcctcctg      5400
ctgctgctgc tctgccagtt catggaggac cgcagtgccc agggtaagcg      5450
agtggggatg cgctggggag gcttggctga ggacagggg gtcgactttt       5500
ctgtggtctc cacttggtct gttctgagca acgctgctct cggaagatgt      5550
tgaaccaact tggggactcc gggatggaga ggagtgggaa aattgtaggc      5600
aatgacactt taggactggg aactgagttt ggagctcggt tatcttgaaa      5650
aaggaaaggg agcgagctgg ggtcttagta gttagggtta aatgctccaa      5700
gttctggcca tgataacttt agatgtgatc tcctctgttt ggctctgaag      5750
aagggaacaa gtatcagtag tagcctggag atttcagtcg acccatttgc      5800
agtctcatct ctctcccctcc cacatctttt ggatacttaa aaaaaaaaaa     5850
```

| | |
|---|---|
| ggaaagaaag aaaagaaaac ctgggggttt gggggagaga tactgaattt | 5900 |
| tatttggtgg ctgggggacg tggtttcaga aactttgccc aaacttggaa | 5950 |
| atgtgggtgc tgaagatttt caagggaagt agctttctgc ctagtggatg | 6000 |
| cttcttccaa ccccatcccc cattctcgca aaaaaaaaa aaaaaaaaaa | 6050 |
| aaagccaaat tattacccca aagtgctttg agcactttac agtttttttc | 6100 |
| ccctctgcct cattcttctt tctgacccct agctttctgt aaaacagtga | 6150 |
| gcagcccata actgacttaa attctgaaat gggttaagag caaatttctg | 6200 |
| aagcttgcct tttaaaaata gatttgttta tttcaattag tctttgggca | 6250 |
| gaatgtttaa aataataata gcagcttgcg atccaatgat tgttaaagtc | 6300 |
| atattggtga ttcatgagaa gtcttctcga cccaaatccg aacattaaaa | 6350 |
| agggggaaga gggagaaatc acttgcaaat atttcttgct aggtatgaga | 6400 |
| taggtactta taaccgtgaa atggtaggaa gactcccccc tccccccacc | 6450 |
| ttaaggcatt actttccctg cttcagcgtt aacattttaa gtatgttgta | 6500 |
| aactgccctc ctgggcactg cccctcgccg tctgcatggc actgcgctgg | 6550 |
| gttgcccgcc tttagaggag aggctctgcc tggtgcccgg acgtgggcgc | 6600 |
| ggaggaaagc agccctcgga gatttcgaaa gatcgcggtg gccgcgggcg | 6650 |
| tgctccggtc tggcggattg caaaacgggc ccgtcgggct ggctgcgcct | 6700 |
| ggaggccgcg cggggtagct ccgggctggg ccgggttgct tttttgcttt | 6750 |
| cattttcag aagtgccttt tgcttgatct gtttctctct ctctctcttt | 6800 |
| cttttctttc ttcctctctc tcttttctttc ttcctttttt tctttctttc | 6850 |
| tcttctcttt cttctttct cttctttctt ttctttcttt cttctctctt | 6900 |
| ccttctccct ctctctcccc tccatctctc ctctctcctc tctctcgttc | 6950 |
| tcttactttc ttaaccctg tcacaaataa ttcctgtacc cgcctacatg | 7000 |
| aaaccagcat gtaaaaacat ccgtcgcatc ctgttttgt caggttcttt | 7050 |
| aatctgctct tcgagtctct gcaggttatg aaatgggacg aataaaagta | 7100 |
| aacagtctag taaaagtcaa tgcaagctgc acgtgttgtg tctgggtcac | 7150 |
| tggtaactga cattgatatg gctggggcgc cctgtcttct ccctctctcc | 7200 |
| ctcccctccct ctcgcccacc tcccatctct gtgatcaggg cttccccctc | 7250 |
| cactgccttc ttttttccacc cctccacccc tttcgattta ttcctactt | 7300 |
| ttctcccgcg tctctctcac ttcccctcct ccacgctcac ccctccca | 7350 |
| tccccgccgg gtcccttcg ctagccacct cgctctccct gccctgccac | 7400 |
| cgctcactgc tcactcaccc acctccccac ccttgtctct tcacagctgg | 7450 |
| gaactgctgg ctccgtcaag cgaagaacg ccgctgccag gtcctgtaca | 7500 |
| agaccgaact gagcaaggag gagtgctgca gcaccggccg gctgagcacc | 7550 |
| tcgtggaccg aggaggacgt gaatgacaac acactcttca gtggatgat | 7600 |
| tttcaacggg ggcgccccca actgcatccc ctgtaaaggt aggactcctt | 7650 |
| cttcccaact tgcaggccct cagtagaggg cgtcttaccc ttagcttccc | 7700 |
| cactacctga ctgggttttg ggagtaggag agctttgttc ctgggcttcc | 7750 |
| ccttcctgtc ccttgccctg gtaagccgtg cagactctaa ttctgcctgt | 7800 |

```
tacaggctgt agggaataca cgccagactt cttagccaag tgtggtggtg         7850
aaacccacca acctgtgctc cttaatgaga gagatctggg tgtggggcac         7900
agcccaaggt ccacactctt tcaccaactc caatattcc aggagagagc          7950 ctggggcccc tccagcgcaa actcagggct gcatgattgc gcaaggcacc         8000
cgaagccctc ctggctgacc tgcagactgc ctggctctgg tttttaatcca        8050 tgcctgtttc taactcacag aaacgtgtga gaacgtggac tgtggacctg        8100
ggaaaaaatg ccgaatgaac aagaagaaca aaccccgctg cgtctgcgcc        8150
ccggattgtt ccaacatcac ctggaagggg ccagtctgcg ggctggatgg        8200
gaaaacctac cgcaatgaat gtgcactcct aaaggcaaga tgtaaagagc        8250
agccagaact ggaagtccag taccaaggca gatgtaaaag taggtcctac        8300
cctgttgagc aagactggat ctgtcccctc ctccagcttt gtacctaaag        8350
tagaccctct agaagaccct tggggatgg tgtagtccgc agtaagagcc         8400
tgataatagt aatactgaaa ccaaataaag gagtccttt ctaacctcta         8450 gagattcatt aagaacactg aggggaccaa cctagtcata gattctctct        8500
tgaaaactac agggctccct aagtgccttt tgaaagctgg atgcttcagt        8550
gtcatgattt ccttggtaac ttcaagtgct cactccctaa ggactagaag        8600
gtacctattc atgtgtgttt ccttcttgt tccagagact tgtcgggatg         8650
ttttctgtcc aggcagctcc acatgtgtgg tggaccagac caataatgcc        8700
tactgtgtga cctgtaatcg gatttgccca gagcctgctt cctctgagca        8750
atatctctgt gggaatgatg gagtcaccta ctccagtgcc tgccacctga        8800
gaaaggctac ctgcctgctg ggcagatcta ttggattagc ctatgaggga        8850
aagtgtatca gtaggtattc tggattgagg aaggaaaaag agaaaacagg        8900
ctagttctat tattaaactg tggggttaac taataagtaa agcccaaggc        8950
gtccccaaac accataggga gaaatacgct gcaatttggg gaaagtgttg        9000
tgaccacagt attcctcatg gaaaccattg tcttctggag gcattgacac        9050
atatattcaa atgccagcag gaagcaagga acagtattcc gtcttagaaa        9100
acttagaact tactcaattt tacacatttt tttaagtgcc agacttgctg        9150
gaagcgaaaa ataattactt agcagttcca gaaatctgtt gtcagattct        9200
agtaattaat ggaattcttt cttttgtaaa agatcccact tgtgggaaat        9250
aataagatac atatttaact tgagaatatt gtaaaatcct gttcttaaaa        9300 aaatacccctt ttaatgcact aatgtagtat gtaagaaact gcagggggttt     9350 tgtgcgtgtg tatgtgtgtg tgcatttgag tttcagtttt attatccagc        9400 attttttgcat aatatctcca ttaccccat tagtaatagg ctattactat        9450
tatgtttata taaaataaat tatgtttata tttattgata gaggactaga        9500
gaaagggaga aaaggggat atggggaaat cagtttactc atcacagatg         9550
tattatatcc tagaagcaaa gtcctgtgaa gatatccagt gcactggtgg        9600
gaaaaaatgt ttatgggatt tcaaggttgg gagaggccgg tgttccctct        9650
gtgatgagct gtgccctgac agtaagtcgg atgagcctgt ctgtgccagt        9700
gacaatgcca cttatgccag cgagtgtgcc atgaaggaag ctgcctgctc        9750
ctcaggtgtg ctactggaag taaagcactc cggatcttgc aactgtaagt        9800
```

```
gcgatttta accttgctgc catttaaggc tttcccaggc aatccctagg        9850
gaatggacac ttacaaagca cgcagatctc ccataaatcc atttctgttc        9900
aaattaggta gctgctaagt atcaccagca attcataatt ccacagaaaa        9950
ttctctgcga tgtttcttgg cttttaggac ttatctggtg atcatcaatg       10000
gggttgcctc tagaaatcta tttccagttg ttttcccta tttcttgtgt         10050 tttggtagtg tgctttgctg tttgctttat aacatttga gtctaaacta         10100 actgcttcaa aagttttttt tttttttttc caacgacagc ttcatattat       10150
cacacatggg ctgctgcttt ttgcagttgc ctctactaac tctgaattaa       10200
ggacccaaag cagttatacc tagaacacaa gagcgctttt tatctaattt       10250
caggaatctg cccgtaaaac ctgagccatt gattcttcag aactttctgc       10300 agttttgac ttcatagatt atgctttaaa aaaatttttt taacttattg         10350
cataacagca gatgccaaaa acaaaaaaag catctcactg caagtcacat       10400
aaaaatgcaa cgctgtaata tggctgtatc agagggcttt gaaaacatac       10450
actgagctgc ttctgcgctg ttgttgtccg tatttaaaca acagctcccc       10500
tgtattcccc catctagcca tttcggaaga caccgaggaa gaggaggaag       10550
atgaagacca ggactacagc tttcctatat cttctattct agagtggtaa       10600
actctctata agtgttcagt gttgacatag cctttgtgca aaaaaaaaa        10650 aaaaaaaaaa gaaaagaaa aaagaaaaa tatattgtcc atactgtaaa         10700
taagtgtatg cttatttatt tgggggaaa actatacatt aaaggacctt        10750
tgtcctaaag ctctctccca ggccaccttg ttactcattg gacacggaga       10800
ggcattcatt gtgaggtcta ctggatgagg cccatagttg agacttgtag       10850
acatttattt atactgtgtc atgttttata atttatacat aaaatgtctg       10900
gttgactgta taccttgttt tgaagaaat ttattcgtga aaggaagagc        10950
agttgttatt tattgtgagg tctcttgctt gtaaagtaaa agctttttt        11000 ccttgtaaac catttaagtc cattccttac tattcactca ctcatctgtc       11050
tcccttcatt tcactgttag actcttttcc actttcaaca aacttgcatg       11100
tcagtttctg tcatgtttat ttattggatt ctctgctgcc tgatctgtac       11150
atacatgatc cctcgggttt tgtttacaag gaaccttgac tgaccaaaag       11200
gcattataac tctgactcaa atacaaggta cagaagataa gcatctttga       11250
ggaaactcct acttcagttc ttttgttatg atgaagacat tgtgagaga        11300 ggagatgatt agaattctag taatgtactt ttaagatgtt acagatacaa       11350
agaaatgatg tgggtgtcag gagactaaag gatgttgaag gctacacatt       11400
caaccttttg ttaggtgttt cctttaagct actcagctgt accttttaaa       11450
ttagttcttt ttcaaccagt atatcactaa aagttatatc aaagctttat       11500
cagttcaagt ttcttgcttt tcataatact ttttctgat gcaattttat        11550 attttcaaac atggcaagtt aaaatataaa ttcatttaaa tatatagttt       11600 tgtactttc taccatgtaa atgtgcaatg tatataaaag ttataatgtg        11650
tatttgtaaa taaatgatga gtgaaaaaat aaaaaatttt taaaaagcca       11700
atggtttcaa ttcctgatga tgcaaagaag ttatttggac ttttgagtaa       11750
```

| | |
|---|---|
| aaatgtgtat gataccttttg ctgaggaatg tagctatctc tgaaattaca | 11800 |
| tggccagggc agtacagatc acttcactgg agtttgaaag ataaagggat | 11850 |
| ctgaggtcca gcaaccccac tgtaggagtg gcatatacct gtcactaacc | 11900 |
| acagaaggaa cagactgtag atgtgggttc tttcctgcaa tatgccaagg | 11950 |
| ctaatatttc ctcttttaaaa acaccatcgt tttagctgtc cttgttgcaa | 12000 |
| gctcatcacc atagccaggg acacgcttca tcttactttc ccataaatcc | 12050 |
| agtgcagttt cagtctttta aaaaacaaca cacatcacaa ggaaagctga | 12100 |
| caacagatat aatatttgac aaacacattc tagaaatcag aatatcagct | 12150 |
| gcagaagtag acattatagt gttggaatgc tagggacttg atgaggtgag | 12200 |
| gatggggtgg aggtgaattt ccacaatgat gtccatggtt agggatcaaa | 12250 |
| taatgtcact cattgtaaga ggaagtgtat caatatttca cagtttacac | 12300 |
| tagacactat tagagcttca gaatggtgtt taggacatca gtcaatggtc | 12350 |
| cctgtaatac ataggaatac ataactagat cataaacata agtttccaat | 12400 |
| tcattgtgtg ctacatactc aaagcctaaa tatattaaaa atatcaaaga | 12450 |
| agtacaagat gcaagcctca gattggcatt tgggccatca ttcactagtc | 12500 |
| cctgtaatat aatgcatagg aatatataac tggagcatca acacaagttt | 12550 |
| ctgattcaat tccaattcca attatgtact tacatattca aagcctaatt | 12600 |
| atatttaaaa tatcagaaat tcaagatgta agaagtatc aggactgtgg | 12650 |
| gagggaaaga gcaaagtata gtcaatatta ccagcatcgc taaacaataa | 12700 |
| taaacatatc atttctttca aacaccatga cccaagttct tcttaaaagt | 12750 |
| ttatcccttt tgtaaaaagc ctctttaata tgaatagtta ttcaaaattg | 12800 |
| ttgccagaga ctgttggctc tcaactgtgg ccacctaatg agaaatttgg | 12850 |
| tggaggtaga gggaccctctt cagtagacag tttatataat gattagagcc | 12900 |
| ctgttggatc ttgttacctt tcagccctgt gttccccaaa aggaaaagag | 12950 |
| aggtgcagaa acaaacagg ctgccattaa ctgcaaaaga caagggtcgt | 13000 |
| aacttctccg gtgtagatta gctactggct tgccactaga g | 13041 |

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 2
ctgattgaca ttcggcagta cg                                           22

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 3
ccccatgagg gtgttggttg                                              20

```
<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcaaagcggc tgtcctatg                                                   19

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gccaaaatct taacacggac ttc                                              23

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgccgccttc ttctacctg                                                   19

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgaagccata gtagctgatg gaa                                              23

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cggattatcc ctgggtatct cg                                               22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgaagtccct tcctcgaaga c                                                21

<210> SEQ ID NO 10
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcagacggac cggatatgc                                                       19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gctgctcgtg tgtcttctca                                                      20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgagctgggc cgaaaatacc                                                      20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gggtccatct ctagccagaa t                                                    21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atgggctgtg atcggaactg                                                      20

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agccaggact gcaccaataa c                                                    21

<210> SEQ ID NO 16
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcgggaacgc aacaacatc                                                     19

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtcactggtc aactccagca c                                                  21

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tgacattcat gggattgcag ac                                                 22

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgagctggat gtatgagggg                                                    20

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atcagcgtaa atggggattt gg                                                 22

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtctgcggtg atttcatcga a                                                  21

<210> SEQ ID NO 22
<211> LENGTH: 21
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 22
gcggagtgca acatcaaagt g                                              21

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gattcgttga gaggtctgaa gc                                             22

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ttgccctaag gacccctgaa                                                20

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acagagtctg ctaatccagg aat                                            23

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gaagctagtt ctacgggaag ga                                             22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aggccaggat aatagtatgc ca                                             22

<210> SEQ ID NO 28
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 28
tcagctctgt ggacctctcc                                                     20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
acccttgcat ccttcacaag                                                     20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gtcaacagca aaagccacaa                                                     20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tctggggtca gaggaagaga                                                     20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tgacgtggac gagctttcac                                                     20

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gggtcttctt atcctgggtg c                                                   21

<210> SEQ ID NO 34
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 34
atgcaagtgc taacgaaacg c                                              21

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
agtaccgatc catgactgtc ag                                             22

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggcatccaga ggcaaatcag                                                20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gcattgtagg tccccgtgta                                                20

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aggccctttt tcatactagc cc                                             22

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aagctcgtca cactgacact t                                              21

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
                            primer

<400> SEQUENCE: 40
atctatcgcc cttgggtctt                                              20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aaaacctacc gcaacgaatg                                              20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggtgggaaat gtcacctgat                                              20

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cggtggatgt ggaatgtgt                                               19
```